US007838553B2

(12) United States Patent
Zhang et al.

(10) Patent No.: US 7,838,553 B2
(45) Date of Patent: Nov. 23, 2010

(54) BENZOPYRAN DERIVATIVES AS POTASSIUM CHANNEL OPENERS

(75) Inventors: Xuqing Zhang, Exton, PA (US); Xiaojie Li, Raritan, NJ (US); Zhihua Sui, Exton, PA (US)

(73) Assignee: Janssen Pharmaceutica NV (BE)

( * ) Notice: Subject to any disclaimer, the term of this patent is extended or adjusted under 35 U.S.C. 154(b) by 1120 days.

(21) Appl. No.: 11/468,325

(22) Filed: Aug. 30, 2006

(65) Prior Publication Data
US 2007/0049556 A1    Mar. 1, 2007

Related U.S. Application Data

(60) Provisional application No. 60/713,323, filed on Sep. 1, 2005.

(51) Int. Cl.
*A61K 31/353*    (2006.01)
(52) U.S. Cl. .................. 514/456; 549/399; 549/400; 549/401; 549/403; 549/404
(58) Field of Classification Search .......... 549/399, 549/400, 403, 404, 401; 514/456
See application file for complete search history.

(56) References Cited

U.S. PATENT DOCUMENTS

| | | | |
|---|---|---|---|
| 4,210,591 A | 7/1980 | Burri | |
| 4,631,282 A | 12/1986 | Cassidy | |
| 4,812,459 A | 3/1989 | Evans et al. | |
| 4,931,454 A | 6/1990 | Baumgarth et al. | |
| 4,971,982 A | 11/1990 | Attwood et al. | |
| 4,983,612 A | 1/1991 | Quagliato et al. | |
| 4,987,138 A | 1/1991 | Cassidy et al. | |
| 5,028,711 A | 7/1991 | Stenzel et al. | |
| 5,096,914 A | 3/1992 | Stenzel et al. | |
| 5,112,839 A | 5/1992 | Gericke et al. | |
| 5,118,694 A | 6/1992 | Attwood et al. | |
| 5,171,857 A | 12/1992 | Quagliato | |
| 5,206,252 A | 4/1993 | Butera et al. | |
| 5,225,566 A | 7/1993 | Butera et al. | |
| 5,236,935 A | 8/1993 | Yoo et al. | |
| 5,254,555 A | 10/1993 | Stemp et al. | |
| 5,254,557 A | 10/1993 | Buckle et al. | |
| 5,254,578 A | 10/1993 | Hashimoto et al. | |
| 5,284,838 A | 2/1994 | Garcia et al. | |
| 5,310,932 A | 5/1994 | Atwal et al. | |
| 5,387,587 A | 2/1995 | Hausler et al. | |
| 5,470,872 A | 11/1995 | Buckle et al. | |
| 6,153,627 A | 11/2000 | Hausler et al. | |
| 2007/0072832 A1 | 3/2007 | Zhang et al. | |

FOREIGN PATENT DOCUMENTS

| | | | |
|---|---|---|---|
| EP | 0172352 A2 | 2/1986 | |
| EP | 0205292 A2 | 12/1986 | |
| EP | 0273262 A2 | 7/1988 | |
| EP | 0298452 A2 | 1/1989 | |
| EP | 0308792 A2 | 3/1989 | |
| EP | 0350805 A1 | 1/1990 | |
| EP | 0406656 A1 | 1/1991 | |
| EP | 0413438 A | 2/1991 | |
| GB | 2242628 A | 10/1991 | |
| WO | WO 93/23393 A | 11/1993 | |
| WO | WO 2005/033073 A2 | 4/2005 | |

OTHER PUBLICATIONS

Aguilar-Bryan et al.: "Toward Understanding the Assembly and Structure of $K_{ATP}$ Channels"; Physiological Reviews vol. 78(1) Jan. 1998; 227-245.

Ashwood, V.A. et al.: "Synthesis and Antihypertensive Activity of Pyran Oxygen and Amide Nitrogen Replacement Analogues of the Potassium Channel Activator Cromakalim", Journal of Medicinal Chemistry, American Chemical Society, Washington, U.S., vol. 34, No. 11, Nov. 1991, pp. 3261-3267, XP002034759.

Ashwood, V.A. et al.: Synthesis and Antihypertensive Activity of 4-(Cyclic Amido)-2H-1-Benzopyrans:, Journal of Medicinal Chemistry, American Chemical Society. Washington, US, vol. 29, 1986, pp. 2194-2201, XP008050667.

Atwal, K.S. et al.: "Cardioselective Anti-Ischemic ATP-Sensitive Potassium Channel Openers. 3. Structure-Activity Studies of Benzopyranyl Cyanoguanidines", Journal of Medicinal Chemistry, American Chemical Society, Washington, US, vol. 38, No. 17, 1995, pp. 3236-3245, XP009030005.

Attwood, M.R. et al.: Tetrahedron Letters, Elsevier, Amsterdam, NL, vol. 32, No. 6, 1991, pp. 811-814, XP002082330.

Bergmann, R. et al.: Synthesis and antihypertensive activity of 4-(1,2-dihydro-2-oxo-1-pyridyl)-2H-1-benzoyrans and related compounds, new potassium channel activators:, Journal of Medicinal Chemistry, Feb. 1990, vol. 33, No. 2, pp. 492-504, XP002418874.

Bergmann, R. et al.: "4-Heterocyclyloxy02H-1-Benzopyran Potassium Channel Activators", Journal of Medicinal Chemistry, American Chemical Society, Washington, US, vol. 33, No. 10, Oct. 1, 1990, pp. 2759-2767, XP000566902.

Buckle, D.R. et al.: "Relaxant Activity of 4-amido-3, 4-dihyro-2H-1-benzopyran-3-ols and 4-amido-2H-1-benzopyrans on guinea pig. isolated trachealis", Journal of Medicinal Chemistry, Nov. 1990, vol. 33(11) pp. 3028-3034, XP002418873.

Burrell, G. et al.: "Variation in the aromatic ring of cromakalim: antihypertensive activity of pyranopyridines and 6-alkyl-2H-1-benzopyrans", Journal of Medicinal Chemistry, Nov. 1990, vol. 33, No. 11, pp. 3023-3027, XP002418872.

Edwards, G. et al.: "Structure-Activity Relationships of K+ Channel Openers".Trends in Pharmacological Sciences, Elsevier, Hayworth, GB, vol. 11, No. 10, Oct. 1990, pp. 417-422, XP002034758.

(Continued)

*Primary Examiner*—Janet L Andres
*Assistant Examiner*—David E Gallis
(74) *Attorney, Agent, or Firm*—Jeremy K. McKown

(57) ABSTRACT

The present invention is directed to novel benzopyran derivatives, pharmaceutical compositions containing them and their use in the treatment of disorders related to potassium channel.

4 Claims, No Drawings

OTHER PUBLICATIONS

Gabbutt, et al.: "Reactions of Some 2H-Chromenes and 2H-Thiochromenes with Triazolinediones", Tetrahedron, Elsevier Science Publishers, Amsterdam, NL, vol. 51, No. 48, Nov. 1995, pp. 13277-13290, XP005249958.

Kabbe, H.J. et al.: "Synthesen und Umsetzungen von-4-Chromanonen", Angewandte Chemie, VCH Verlagsgesellschaft, Weinheim, DE, vol. 94, 1982, pp. 254-262, XP002418875.

Mannhold, R. et al.: "6-Substituted benzopyrans as potassium channel activators: synthesis, vasodilator properties, and multivariate analysis", Journal of Medicinal Chemistry, Mar. 25, 1999, vol. 42, No. 6, pp. 981-991, XP002418870.

Robertson, D.W. et al: "Potassium Channel Modulators: Scientific Applications and Therapeutic Promise", Journal of Medicinal Chemistry, American Chemical Society, Washington, U.S., vol. 33, No. 6, Jun. 1990, pp. 1529-1541, XP002034757.

Salamon, E. et al.: "6-Sulfonylchromenes as highly potent K(ATP)-channel openers", Journal of Medicinal Chemistry, Feb. 28, 2002, vol. 45, No. 5, pp. 1086-1097, XP002418871.

Vuligonda, V. et al.: "A new class of potent RAR antagonists: dihydroanthracenyl, benzochromenyl and benzothiochromenyl retinoids" Bioorganic & Medicinal Chemistry Letters, Oxford, GB, vol. 9, No. 5, Mar. 8, 1999, pp. 743-748, XP004157605.

Wein, A.J., MD: "Overactive Bladder: Defining the Disease"; the American J. of Managed Care, vol. 6(11) Jul. 2000, S559-S564.

PCT International Search Report for International Appln No. PCT/US06/34128 dated Apr. 12, 2006.

BENZOPYRAN DERIVATIVES AS POTASSIUM CHANNEL OPENERS

CROSS REFERENCE TO RELATED APPLICATIONS

This application claims the benefit of U.S. Provisional Application 60/713,323, filed on Sep. 1, 2005, which is incorporated by reference herein in its entirety.

FIELD OF THE INVENTION

The present invention is directed to novel benzopyran derivatives, pharmaceutical compositions containing them and their use in the treatment of potassium channel related disorders. The compounds of the invention are thus useful for treatment of various disorders. This includes but is not limited to urinary incontinence, overactive bladder, hypertension, erectile dysfunction, female sexual disorders, dysmenorrhea, irritable bowl syndrome, airway hyperactivity, epilepsy, stroke, Alzheimer's and Parkinson's diseases, myocardial injury, coronary artery disease as well as hair loss and baldness.

BACKGROUND OF THE INVENTION

Ion channels play a fundamental role in the hormeostasis of cell function through the regulation of the transmembrane movement of ions. Cellular activity can be affected by modifications of the activities of the ion channels. This leads to changes in membrane potential difference. Potassium channels are a diverse and ubiquitous group of ion channels. They principally regulate the resting membrane potential of the cell and attenuate the level of excitation of cells. A functional $K_{ATP}$ channel is a hetero-octamer assembled from four inward rectifying potassium channel subunits (Kir6.2) and four sulfonylurea receptor (SUR) subunits. There are two SUR genes, SUR1 and SUR2. SUR1/Kir6.2 channels are found in the pancreas and brain. Two major splice variants arise from the SUR2 gene, SUR2A and SUR2B, that differ only at the C-terminal 42 amino acids. SUR2A/Kir6.2 channels are found in cardiac and skeletal tissues whereas SUR2B/Kir6.2 channels are found in smooth muscles of many tissues including bladder (Aguilar-Bryan, 1998). A number of diseases or conditions may be treated with potassium channel openers. This includes overactive bladder, urinary incontinence, male erectile dysfunction, female sexual disorders, premature labor, benign prostate hyperplasia (BPH), dysmenorrhea, neurodegeneration, stroke, pain, coronary artery disease, angina, ischemia, eating disorders, irritable bowl syndrome, alopecia.

Urinary incontinence (UI) is a disease that can affect the overall quality of life of a patient. Overactive bladder (OAB) is the most prevalent form of UI, with reported prevalence rate from 40 to 70% of all diagnosed UI cases (Wein, 2000). OAB is characterized by the symptoms of increased urinary frequency, urgency, and involuntary loss of urine. A primary cause of OAB is an oversensitive bladder that contracts unexpectedly and involuntarily. The ideal pharmaceutical agent should suppress the involuntary contraction while leaving the normal voiding contractions intact. ATP-sensitive potassium channel openers (KCO) could serve as such agents. The ATP-sensitive potassium channels ($K_{ATP}$) are expressed in bladder smooth muscle and function as key regulators of the resting membrane potential in these cells. Compounds that selectively open these channels hyperpolarize the cell and decrease cellular excitability, resulting in suppression of involuntary bladder contractions, while leaving the normal micturition circuitry intact.

SUMMARY OF THE INVENTION

The present invention is directed to compounds of formula (I)

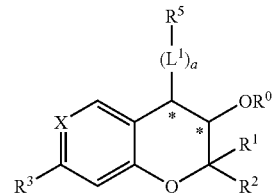

$R^0$ is selected from the group consisting of hydrogen, $C_{1-4}$alkyl, —C(O)—$C_{1-4}$alkyl and —C(O)-phenyl; wherein the phenyl is optionally substituted with one or more substituents independently selected from halogen, $C_{1-4}$alkyl, halogen substituted $C_{1-4}$alkyl, $C_{1-4}$alkoxy, halogen substituted $C_{1-4}$alkoxy, hydroxy, nitro, cyano, amino, $C_{1-4}$alkylamino or di($C_{1-4}$alkyl)amino;

$R^1$ and $R^2$ are each independently selected from the group consisting of $C_{1-4}$alkyl;

alternatively, $R^1$ and $R^2$ are taken together with the carbon atom to which they are bound to form a 5 to 7 membered cycloalkyl or a 5 to 7 membered heterocycloalkyl ring structure;

wherein the heterocycloalkyl ring structure is saturated or partially unsaturated and wherein the heterocycloalkyl ring comprises 1 to 2 heteroatoms independently selected from the group consisting of O, S and $NR^A$; wherein $NR^A$ is selected from hydrogen or $C_{1-4}$alkyl;

wherein the 5 to 7 membered cycloalkyl or 5 to 7 membered heterocycloalkyl ring structure is optionally substituted with one or more substituents independently selected from halogen, hydroxy, oxo, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy;

$R^3$ is selected from the group consisting of hydrogen, halogen, hydroxy, cyano, $C_{1-4}$alkyl, $C_{1-4}$alkoxy, halogen substituted $C_{1-4}$alkyl, halogen substituted $C_{1-4}$alkoxy, nitro, amino, $C_{1-4}$alkylamino, di($C_{1-4}$alkyl)amino, —S(O)$_{0-2}$—$C_{1-4}$alkyl, —S(O)$_{0-2}$-aryl, —S(O)$_{0-2}$—$NR^CR^D$, —C(O)—$C_{1-4}$alkyl, —C(O)-aryl, —C(O)—$NR^CR^D$, —$NR^B$—SO$_2$—$C_{1-4}$alkyl and —$NR^B$—SO$_2$-aryl;

wherein the aryl is optionally substituted with one or more substituents independently selected from halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy;

wherein $R^B$ is selected from the group consisting of hydrogen and $C_{1-4}$alkyl;

X is selected from the group consisting of $CR^4$ and N;

$R^4$ is selected from the group consisting of halogen, hydroxy, cyano, $C_{1-4}$alkyl, $C_{1-4}$alkoxy, halogen substituted $C_{1-4}$alkyl, halogen substituted $C_{1-4}$alkoxy, nitro, amino, $C_{1-4}$alkylamino, di($C_{1-4}$alkyl)amino, —S(O)$_{0-2}$—$C_{1-4}$alkyl, —S(O)$_{0-2}$-aryl, —S(O)$_{0-2}$—$NR^CR^D$, —C(O)—$C_{1-4}$alkyl, —C(O)-aryl, —C(O)—$NR^CR^D$, —$NR^E$SO$_2$—$C_{1-4}$alkyl and —$NR^E$—SO$_2$-aryl;

wherein the aryl is optionally substituted with one or more substituents independently selected from halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy;

wherein $R^C$ and $R^D$ are each independently selected from the group consisting of hydrogen and $C_{1-4}$alkyl; alternatively, $R^C$ and $R^D$ are taken together with the nitrogen atom to which they are bound to form a 5 to 7 membered heteroaryl or 5 to 7 membered heterocycloalkyl ring structure;

wherein $R^E$ is selected form the group consisting of hydrogen and $C_{1-4}$alkyl;

a is an integer from 0 to 1;

$L^1$ is selected from the group consisting of —O—, —S—, —SO—, —SO$_2$—, —NR$^G$—, NR$^G$—C(O), —NR$^G$—SO$_2$—, —O—P(O)(R$^H$)— and —NR$^G$—P(O)(R$^H$)—;

wherein $R^G$ is selected from the group consisting of hydrogen and $C_{1-4}$alkyl; and wherein $R^H$ is selected from the group consisting of $C_{1-4}$alkyl and phenyl;

$R^5$ is selected from the group consisting of phenyl, a 5 to 6 membered heterocyclyl group comprising at least one N atom and a 9 to 10 membered heterocyclyl group comprising at least one N atom;

wherein the 5 to 6 membered heterocyclyl group is optionally substituted with one or more substituents independently selected from halogen, oxo, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl, halogen substituted $C_{1-4}$alkoxy, —S(O)$_{0-2}$—$C_{1-4}$alkyl, —NR$^J$—SO$_2$—$C_{1-4}$alkyl or phenyl;

wherein the 9 to 10 membered heterocyclyl group is optionally substituted with one or more substituents independently selected from halogen, oxo, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl, halogen substituted $C_{1-4}$alkoxy, —S(O)$_{0-2}$—$C_{1-4}$alkyl, —NR$^J$—SO$_2$—$C_{1-4}$alkyl or phenyl;

wherein $R^J$ is selected from hydrogen or $C_{1-4}$alkyl;

wherein the phenyl, whether alone or as part of a substituent group, is optionally substituted with one or more substituents independently selected from halogen, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl or halogen substituted $C_{1-4}$alkoxy;

provided that the -(L$^1$)$_a$-R$^5$ substituent group and the —OR$^0$ substituent group are in a trans orientation (relative to each other);

provided further that when L$^1$ is —NR$^G$—C(O)—, then R$^1$ and R$^2$ are taken together with the carbon atom to which they are bound to form a ring structure;

provided further that when R$^5$ is phenyl, then L$^1$ is —O—P(O)(R$^H$)— or —NR$^G$—P(O)(R$^H$)—;

provided further than when R$^0$ is hydrogen or methyl; R$^1$ is methyl; R$^2$ is methyl; R$^3$ is methoxy; X is CR$^4$; R$^4$ is methoxy; a is 1; L$^1$ is —NH—; then R$^5$ is other than purinyl;

provided further than when R$^0$ is hydrogen; R$^1$ and R$^2$ are each methyl or are each ethyl; X is CR$^4$; and a is 0; then R$^5$ is other than 1-pyrrolidinyl, 1-pyrrolidin-2-one, 1-(5-methylpyrrolidin-2-one), 1-piperidinyl, 1-piperidin-2-one, 1-(2-oxo-pyridyl) or 1-(4-methyl-1,2,3,5-tetrazolyl);

provided further that when R$^0$ is hydrogen or acetyl; R$^1$ and R$^2$ are each methyl; X is CR$^4$; R$^3$ and R$^4$ are each methoxy; a is 0; then R$^5$ is other than 4-morpholinyl;

and pharmaceutically acceptable salts thereof.

The present invention is further directed to compounds of formula (II)

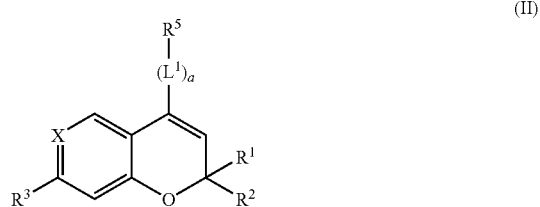

(II)

wherein $R^1$ and $R^2$ are each independently selected from the group consisting of $C_{1-4}$alkyl;

alternatively, $R^1$ and $R^2$ are taken together with the carbon atom to which they are bound to form a 5 to 7 membered cycloalkyl or a 5 to 7 membered heterocycloalkyl ring structure;

wherein the heterocycloalkyl ring structure is saturated or partially unsaturated and wherein the heterocycloalkyl ring comprises 1 to 2 heteroatoms independently selected from the group consisting of O, S and NR$^A$; wherein NR$^A$ is selected from hydrogen or $C_{1-4}$alkyl;

wherein the 5 to 7 membered cycloalkyl or 5 to 7 membered heterocycloalkyl ring structure is optionally substituted with one or more substituents independently selected from halogen, hydroxy, oxo, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy;

$R^3$ is selected from the group consisting of hydrogen, halogen, hydroxy, cyano, $C_{1-4}$alkyl, $C_{1-4}$alkoxy, halogen substituted $C_{1-4}$alkyl, halogen substituted $C_{1-4}$alkoxy, nitro, amino, $C_{1-4}$alkylamino, di($C_{1-4}$alkyl)amino, —S(O)$_{0-2}$—$C_{1-4}$alkyl, —S(O)$_{0-2}$-aryl, —S(O)$_{0-2}$—NR$^C$R$^D$, —C(O)—$C_{1-4}$alkyl, —C(O)-aryl, —C(O)—NR$^C$R$^D$, —NR$^B$—SO$_2$—$C_{1-4}$alkyl and —NR$^B$—SO$_2$-aryl;

wherein the aryl is optionally substituted with one or more substituents independently selected from halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy; and wherein $R^B$ is selected from the group consisting of hydrogen and $C_{1-4}$alkyl;

X is selected from the group consisting of CR$^4$ and N;

$R^4$ is selected from the group consisting of halogen, hydroxy, cyano, $C_{1-4}$alkyl, $C_{1-4}$alkoxy, halogen substituted $C_{1-4}$alkyl, halogen substituted $C_{1-4}$alkoxy, nitro, amino, $C_{1-4}$alkylamino, di($C_{1-4}$alkyl)amino, —S(O)$_{0-2}$—$C_{1-4}$alkyl, —S(O)$_{0-2}$-aryl, —S(O)$_{0-2}$—NR$^C$R$^D$, —C(O)—$C_{1-4}$alkyl, —C(O)-aryl, —C(O)—NR$^C$R$^D$, —NR$^E$—SO$_2$—$C_{1-4}$alkyl and —NR$^E$—SO$_2$-aryl;

wherein the aryl is optionally substituted with one or more substituents independently selected from halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy;

wherein $R^C$ and $R^D$ are each independently selected from the group consisting of hydrogen and $C_{1-4}$alkyl; alternatively, $R^C$ and $R^D$ are taken together with the nitrogen atom to which they are bound to form a 5 to 7 membered heteroaryl or 5 to 7 membered heterocycloalkyl ring structure;

wherein $R^E$ is selected form the group consisting of hydrogen and $C_{1-4}$alkyl;

a is an integer from 0 to 1;

$L^1$ is selected from the group consisting of —O—, —S—, —SO—, —SO$_2$—, —NR$^G$—, NR$^G$—C(O), —NR$^G$—SO$_2$—, —O—P(O)(R$^H$)— and —NR$^G$—P(O)(R$^H$)—;

wherein $R^G$ is selected from the group consisting of hydrogen and $C_{1-4}$alkyl; and wherein $R^H$ is selected from the group consisting of $C_{1-4}$alkyl and phenyl;

$R^5$ is selected from the group consisting of phenyl, a 5 to 6 membered heterocyclyl group comprising at least one N atom and a 9 to 10 membered heterocyclyl group comprising at least one N atom;

wherein the 5 to 6 membered heterocyclyl group is optionally substituted with one or more substituents independently selected from halogen, oxo, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl, halogen substituted $C_{1-4}$alkoxy, —S(O)$_{0-2}$—$C_{1-4}$alkyl, —NR$^J$—SO$_2$—$C_{1-4}$alkyl or phenyl;

wherein the 9 to 10 membered heterocyclyl group is optionally substituted with one or more substituents independently selected from halogen, oxo, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl, halogen substituted $C_{1-4}$alkoxy, —S(O)$_{0-2}$—$C_{1-4}$alkyl, —NR$^J$—SO$_2$—$C_{1-4}$alkyl or phenyl;

wherein $R^J$ is selected from hydrogen or $C_{1-4}$alkyl;

wherein the phenyl, whether alone or as part of a substituent group, is optionally substituted with one or more substituents independently selected from halogen, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl or halogen substituted $C_{1-4}$alkoxy;

provided that when $L^1$ is —NR$^G$ C(O)—, then $R^1$ and $R^2$ are taken together with the carbon atom to which they are bound to form a ring structure;

provided further that when $R^5$ is phenyl, then $L^1$ is —O—P(O)(R$^H$)— or —NR$^G$—P(O)(R$^H$)—;

provided further that when $R^1$ is methyl; $R^2$ is methyl; X is CR$^4$; $R^3$ is nitro and $R^4$ is amino or $R^3$ is amino and $R^4$ is nitro; and a is 0; then $R^5$ is other than 1-pyrrolidin-2-one;

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders related to ion channels, preferably a potassium ion channel, more preferably an ATP-sensitive potassium ion channel, comprising administering, to a subject in need thereof, a therapeutically effective amount of any of the compounds or pharmaceutical compositions described above.

An example of the invention is a method for treating a disorder selected from the group consisting of urinary incontinence, overactive bladder, hypertension, erectile dysfunction, female sexual disorders, dysmenorrhea, irritable bowl syndrome, airway hyperactivity, epilepsy, stroke, Alzheimer's disease, Parkinson's disease, myocardial injury, coronary artery disease, hair loss and baldness, preferably urinary incontinence, comprising administering, to a subject in need thereof, an effective amount of any of the compounds or pharmaceutical compositions described above.

Another example of the invention is the use of any of the compounds described herein in the preparation of a medicament for treating: (a) urinary incontinence, (b) overactive bladder, (c) hypertension, (d) erectile dysfunction, (e) female sexual disorders, (f) dysmenorrhea, (g) irritable bowl syndrome, (h) airway hyperactivity, (i) epilepsy, (j) stroke, (k) Alzheimer's disease, (l) Parkinson's disease, (m) myocardial injury, (n) coronary artery disease, (o) hair loss or (p) baldness, in a subject in need thereof.

DETAILED DESCRIPTION OF THE INVENTION

The present invention is directed to compounds of formula (I) and compounds of formula (II)

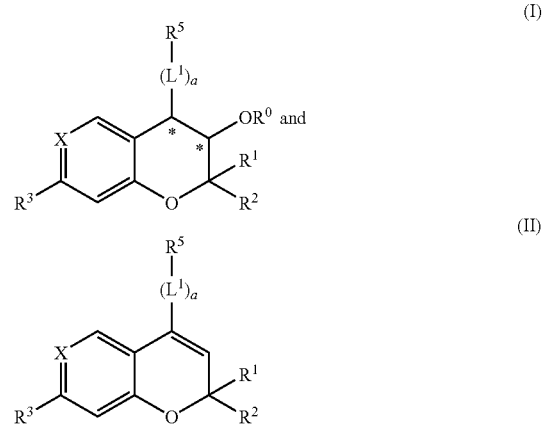

wherein $R^0$, $R^1$, $R^2$, $R^3$, X, b, $L^1$ and $R^5$ are as herein defined. The compounds of the present invention are potassium channels openers. The compounds of the present are thus useful for treatment of various disorders including, but not limited to, urinary incontinence, overactive bladder, hypertension, erectile dysfunction, female sexual disorders, dysmenorrhea, irritable bowel syndrome, airway hyperactivity, epilepsy, stroke, Alzheimer's and Parkinson's diseases, myocardial injury, coronary artery disease as well as hair loss and baldness. Preferably, the compounds of the present invention are useful in the treatment of urinary incontinence or overactive bladder.

Compounds of Formula (C)

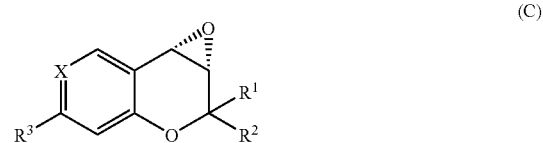

wherein X, $R^1$, $R^2$ and $R^3$ are as herein defined are useful as intermediates in the synthesis of compounds of formula (I) and compounds of formula (II).

As used herein, "halogen" shall mean chlorine, bromine, fluorine and iodine. Preferably, the halogen is chlorine, bromine or fluorine, more preferably, chlorine or fluorine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, t-butyl, pentyl and the like. Similarly, the term "$C_{1-4}$alkyl" whether used alone or as part of a substituent group, include straight and branched chains containing 4 carbon atoms. For example, methyl, ethyl, n-propyl, isopropyl, n-butyl, isobutyl, sec-butyl and t-butyl.

As used herein, unless otherwise noted, "alkoxy" whether used alone or as part of a substituent group, shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{1-4}$alkoxy" whether used alone or as part of a substituent group, shall denote an oxygen ether radical of the above described straight or branched chain $C_{1-4}$alkyl groups. For example, methoxy, ethoxy, n-propoxy, sec-butoxy, t-butoxy, and the like.

As used herein, unless otherwise noted, the term "halogen substituted $C_{1-4}$alkyl" shall mean any $C_{1-4}$alkyl group as defined above substituted with at least one halogen atom, preferably substituted with a least one fluoro atom. Suitable examples include but are not limited to —$CF_3$, —$CHF_2$, —$CH_2$—$CF_3$, —$CF_2$—$CF_2$—$CF_2$—$CF_3$, and the like. Similarly, as used herein, unless otherwise noted, the term "halogen substituted $C_{1-4}$alkoxy" shall mean any $C_{1-4}$alkoxy group as defined above substituted with at least one halogen atom, preferably substituted with a least one fluoro atom. Suitable examples include but are not limited to —$OCF_3$, —$OCHF_2$, —$OCH_2$—$CF_3$, —$OCF_2$—$CF_2$—$CF_2$—$CF_3$, and the like.

As used herein, unless otherwise noted, "aryl" shall refer to unsubstituted carbocylic aromatic groups such as phenyl, naphthyl, and the like. Preferably, the aryl group is phenyl or naphthyl, more preferably, phenyl.

As used herein, unless otherwise noted, the term "partially unsaturated" when referring to a ring structure shall mean that the ring structure is stable and contains at least one unsaturated bond (i.e. at least one double bond). Suitable examples include, but are not limited to cyclohexenyl, and the like.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated, partially aromatic bicyclic or spiro-fused ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heterocycloalkyl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, 2-aza-spiro[4.5]decyl and the like.

As used herein, unless otherwise noted, the term "heterocyclyl" shall mean any heteroaryl or heterocyclyl group, as defined above. Preferably, the heterocyclyl group comprises at least one nitrogen atom. More preferably, the heterocyclyl group comprises one to three heteroatoms independently selected from the group consisting of O, S and N. More preferably still, the heterocyclyl group comprises one to two heteroatoms independently selected from the group consisting of O, S and N. Preferably, the heterocyclyl group comprises one N atom and further comprises one additional heteroatom independently selected from the group consisting of O, S and N. Preferably, the heterocyclyl group is saturated, aromatic or partially aromatic, more preferably, the heterocyclyl group is aromatic or benzo-fused.

Preferably, the heterocyclyl is selected from the group consisting of 4,5-dihydro-oxazolyl, piperidiny, imidazolyl, pyrimidinyl, pyrazolyl, pyrazolinyl, pyridazinyl, indolinyl, indazolyl, isoindolyl, pyrrolo[3,4-c]pyridinyl, benzimidazolyl, benzoisothiazolyl, benzoisoxazolyl, benzthiazolyl, benzoxazolyl, quinazolinyl, quinolinyl and isoquinolinyl.

As used herein, the notation "*" shall denote the presence of a stereogenic center.

When a particular group is "substituted" (e.g., aryl, heterocycloalkyl, heteroaryl), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —SO$_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Under standard nomenclature used throughout this disclosure, the terminal portion of the designated side chain is described first, followed by the adjacent functionality toward the point of attachment. Thus, for example, a "phenyl-C$_{1-4}$alkyl-amino-carbonyl-C$_{1-4}$alkyl-" substituent refers to a group of the formula

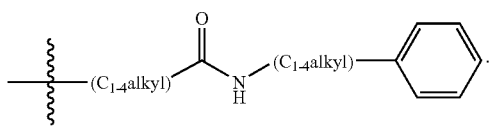

Abbreviations used in the specification, particularly the Schemes and Examples, are as follows:
BuLi or n-BuLi=n-Butyl lithium
Bu$_4$NI=Tetra-n-butyl ammonium iodide
DBU=1,8-Diazabicyclo[5.4.0]undec-7-ene
DCM=Dichloromethane
DEA=Diethylamine
DIPEA=Diethylisopropylamine
DMAC=Dimethylacetamide
DMF=N,N-Dimethylformamide
DMSO=Dimethylsulfoxide
Et=Ethyl (i.e. —CH$_2$CH$_3$)
EtI=Ethyl Iodine
EtOAc=Ethyl acetate
EtOH=Ethanol
HPLC=High Pressure Liquid Chromatography
HRT=Hormone replacement therapy
mCPBA=3-Chloroperoxybenzoic acid
Me=Methyl (i.e. —CH$_3$)
MeI=Methyl Iodide
MeO=Methoxy
MeOH=Methanol
NaBH$_4$=Sodium borohydride
NaOAc=Sodium Acetate
OXONE=Potassium monopersulfate triple salt
PBS=Phosphate buffered solution
PTSA=p-Toluene sulfonic acid
TEA or Et$_3$N=Triethylamine
Tf=Triflate (i.e. —O—SO$_2$—CF$_3$)
THF=Tetrahydrofuran The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The present invention includes within its scope "prodrugs" of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The present invention includes within its scope "pharmaceutically acceptable salts" of the compounds of this invention. For use in medicine, the salts of the compounds of this invention refer to non-toxic pharmaceutically acceptable salts. Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In an embodiment, the present invention is directed to compounds of formula (Ia)

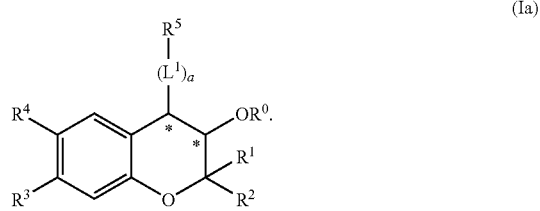

(Ia)

In another embodiment, the present invention is directed to compounds of formula (Ib)

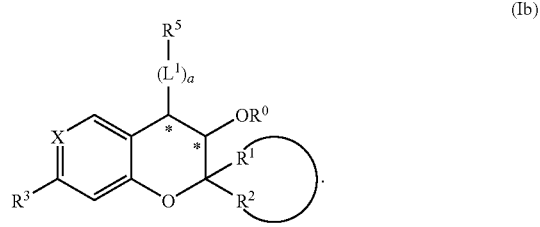

(Ib)

In an embodiment of the present invention X is N. In another embodiment of the present invention X is $CR^4$.

In an embodiment of the present invention, $R^0$ is selected from the group consisting of hydrogen, —C(O)—$C_{1-4}$alkyl and —C(O)-phenyl; wherein the phenyl is optionally substituted with one to two substituents independently selected from halogen, $C_{1-4}$alkyl, halogen substituted $C_{1-4}$alkyl, $C_{1-4}$alkoxy, halogen substituted $C_{1-4}$alkoxy, hydroxy, nitro, cyano, amino, $C_{1-4}$alkylamino or di($C_{1-4}$alkyl)amino.

In another embodiment of the present invention, $R^0$ is selected from the group consisting of hydrogen and —C(O)-phenyl; wherein the phenyl is optionally substituted with a halogen.

In another embodiment of the present invention, $R^0$ is selected from the group consisting of hydrogen and 3-chlorophenyl-carbonyl-.

In another embodiment of the present invention, $R^0$ is hydrogen.

In an embodiment of the present invention, $R^1$ and $R^2$ are each independently selected from the group consisting of $C_{1-2}$alkyl.

In another embodiment of the present invention, $R^1$ and $R^2$ are each methyl.

In an embodiment of the present invention, $R^1$ and $R^2$ are taken together with the carbon atom to which they are bound to form a 5 to 6 membered cycloalkyl or a 5 to 6 membered heterocycloalkyl ring structure; wherein the heterocycloalkyl ring structure is saturated and wherein the heterocycloalkyl ring comprises 1 to 2 heteroatoms independently selected from the group consisting of O, S and $NR^A$; wherein $NR^A$ is selected from hydrogen or $C_{1-2}$alkyl; wherein the 5 to 6 membered cycloalkyl or 5 to 6 membered heterocycloalkyl ring structure is optionally substituted with one to three substituents independently selected from halogen, hydroxy, oxo, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy.

In another embodiment of the present invention, $R^1$ and $R^2$ are taken together with the carbon atom to which they are bound to form a 5 to 6 membered heterocycloalkyl ring structure; wherein the heterocycloalkyl ring is saturated and wherein the heterocycloalkyl ring comprises 1 to 2 heteroatoms independently selected from the group consisting of O, S and $NR^A$; wherein $NR^A$ is selected from hydrogen or $C_{1-2}$alkyl; wherein the 5 to 6 membered heterocycloalkyl ring structure is optionally substituted with one to two oxo groups.

In another embodiment of the present invention, $R^1$ and $R^2$ are taken together with the carbon atom to which they are bound to form 4-(tetrahydro-thiopyran-1,1-dioxide).

In an embodiment of the present invention, $R^3$ is selected from the group consisting of hydrogen, halogen, cyano, $C_{1-4}$alkyl, $C_{1-4}$alkoxy, halogen substituted $C_{1-4}$alkyl, halogen substituted $C_{1-4}$alkoxy, —S(O)$_{0-2}$—$C_{1-4}$alkyl, —S(O)$_{0-2}$-phenyl, —$NR^B$—SO$_2$—$C_{1-4}$alkyl and —$NR^B$—SO$_2$-phenyl; wherein the phenyl is optionally substituted with one to two substituents independently selected from halogen, hydroxy, amino, $C_{1-4}$alkylamino, di($C_{1-4}$alkyl)amino, cyano, nitro, $C_{1-4}$alkyl, $C_{1-4}$alkoxy, halogen substituted $C_{1-4}$alkyl or halogen substituted $C_{1-4}$alkoxy; and wherein $R^B$ is selected from the group consisting of hydrogen and $C_{1-4}$alkyl.

In another embodiment of the present invention, $R^3$ is selected from the group consisting of hydrogen and halogen.

In another embodiment of the present invention, $R^3$ is selected from the group consisting of hydrogen and chloro.

In another embodiment of the present invention, $R^3$ is hydrogen.

In an embodiment of the present invention, $R^4$ is selected from the group consisting of halogen, hydroxy, cyano, $C_{1-4}$alkyl, $C_{1-4}$alkoxy, halogen substituted $C_{1-4}$alkyl, halogen substituted $C_{1-4}$alkoxy, —S(O)$_{0-2}$—$C_{1-4}$alkyl, —S(O)$_{0-2}$-phenyl, —S(O)$_{0-2}$—$NR^CR^D$, —C(O)—$C_{1-4}$alkyl, —C(O)-phenyl, —C(O)—$NR^CR^D$, $NR^E$ SO$_2$—$C_{1-4}$alkyl and —$NR^E$—SO$_2$-phenyl; wherein the phenyl is optionally substituted with one to two substituents independently selected from halogen, hydroxy, amino, $C_{1-4}$alkylamino, di($C_{1-4}$alkyl) amino, cyano, nitro, $C_{1-4}$alkyl, $C_{1-4}$alkoxy, halogen substituted $C_{1-4}$alkyl or halogen substituted $C_{1-4}$alkoxy; wherein $R^C$ and $R^D$ are each independently selected from the group consisting of hydrogen and $C_{1-4}$alkyl; alternatively, $R^C$ and $R^D$ are taken together with the nitrogen atom to which they are bound to form a 5 to 6 membered heteroaryl or 5 to 6 membered saturated heterocycloalkyl ring structure; wherein $R^E$ is selected from the group consisting of hydrogen and $C_{1-4}$alkyl.

In another embodiment of the present invention, $R^4$ is selected from the group consisting of cyano, halogen, —C(O)-phenyl, —C(O)—$NR^CR^D$, —SO$_2$-phenyl and —SO$_2$—$NR^CR^D$; wherein the phenyl is optionally substituted with a substituent selected from halogen or $C_{1-2}$alkoxy; wherein $R^C$ and $R^D$ are each independently selected from the group consisting of hydrogen and $C_{1-2}$alkyl; alternatively, $R^C$ and $R^D$ are taken together with the nitrogen atom to which they are bound to form a 5 to 6 membered saturated heterocycloalkyl group.

In another embodiment of the present invention, $R^4$ is selected from the group consisting of cyano, chloro, phenyl-sulfonyl-, 4-methoxyphenyl-sulfonyl-, 3-fluorophenyl-sulfonyl-, 4-chlorophenyl-sulfonyl-, diethylamino-sulfonyl-, 1-piperidinyl-sulfonyl, phenyl-carbonyl- and diethylamino-carbonyl-.

In another embodiment of the present invention, $R^4$ is selected from the group consisting of cyano, phenyl-carbonyl-, phenyl-sulfonyl-, 1-piperidinyl-sulfonyl-, 3-fluorophenyl-sulfonyl-, 4-chlorophenylsulfonyl- and 4-methoxyphenyl-sulfonyl-.

In another embodiment of the present invention, $R^4$ is selected from the group consisting of cyano, phenyl-sulfonyl-, 1-piperidinyl-sulfonyl- and 3-fluorophenyl-sulfonyl-.

In another embodiment of the present invention, $R^4$ is cyano. In an embodiment of the present invention a is 0 (i.e. $L^1$ is absent). In another embodiment of the present invention a is 1.

In an embodiment of the present invention, $(L^1)_a$ is other than —O—P(O)($R^H$)— and —$NR^G$—P(O)($R^H$)—. In another embodiment or the present invention, $(L^1)_a$ is selected from the group consisting of —O—P(O)($R^H$)— and —$NR^G$—P(O)($R^H$)—.

In an embodiment of the present invention $R^G$ is selected from the group consisting of hydrogen and methyl, preferably hydrogen. In an embodiment of the present invention $R^H$ is selected from the group consisting of methyl and phenyl.

In an embodiment of the present invention, $L^1$ is selected from the group consisting of —O—, —S—, —SO—, —SO$_2$—, —$NR^G$—, —O—P(O)($R^H$)— and —$NR^G$—P(O)($R^H$)—. In another embodiment of the present invention, $L^1$ is selected from the group consisting of —O—, —S—, —SO—, —SO$_2$—, —$NR^G$—, —$NR^G$—SO$_2$—, —O—P(O)($R^H$)— and —$NR^G$—P(O)($R^H$)—. In another embodiment of the present invention, $L^1$ is selected from the group consisting of —$NR^G$—C(O)— and —$NR^G$—SO$_2$—.

In an embodiment of the present invention, $L^1$ is selected from the group consisting of —O—, —S—, —SO—, —SO$_2$—, —$NR^G$—, —$NR^G$—C(O)—, —$NR^G$—SO$_2$—, —P(O)($R^H$)— and —$NR^G$—P(O)($R^H$)—; wherein $R^G$ is selected from the group consisting of hydrogen and $C_{1-4}$alkyl; and wherein $R^H$ is selected from the group consisting of $C_{1-4}$alkyl and phenyl.

In another embodiment of the present invention, $L^1$ is selected from the group consisting of —O—, —S—, —SO$_2$—, —$NR^G$—, α-$NR^G$—C(O)—, —$NR^G$—SO$_2$—, —P(O)($R^H$)— and —$NR^G$—P(O)($R^H$)—; wherein $R^G$ is selected from the group consisting of hydrogen and $C_{1-2}$alkyl; and wherein $R^H$ is selected from the group consisting of $C_{1-2}$alkyl and phenyl.

In another embodiment of the present invention, $L^1$ is selected from the group consisting of —O—, —S—, —SO$_2$—, —NH—, —NH—C(O)—, —NH—SO$_2$—, —O—P(O)(phenyl)-, —NH—P(O)(methyl)- and —NH—P(O)(phenyl)-.

In another embodiment of the present invention, $L^1$ is selected from the group consisting of —O—, —S—, —SO$_2$—, —NH— and —NH—SO$_2$—.

In another embodiment of the present invention, $L^1$ is selected from the group consisting of —O—, —S—, —NH— and —NH—SO$_2$—.

In another embodiment of the present invention, $L^1$ is selected from the group consisting of —O—, —NH— and —N(CH$_3$)—.

In another embodiment of the present invention, $L^1$ is selected from the group consisting of —NH— and —N(CH$_3$)—.

In another embodiment of the present invention, $L^1$ is selected from the group consisting of —O— and —NH—. In another embodiment of the present invention, $L^1$ is —O—. In another embodiment of the present invention, $L^1$ is —NH—.

In an embodiment of the present invention, $R^5$ is selected from the group consisting of phenyl, a 5 to 6 membered heterocyclyl group comprising at least one N atom and a 9 to 10 membered heterocyclyl group comprising at least one N atom; wherein the 5 to 6 membered heterocyclyl group is optionally substituted with one to three substituents independently selected from halogen, oxo, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl, halogen substituted $C_{1-4}$alkoxy or phenyl; wherein the 9 to 10 membered heterocyclyl group is optionally substituted with one to three substituents independently selected from halogen, oxo, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl or halogen substituted $C_{1-4}$alkoxy; wherein the phenyl, whether alone or as part of a substituent group, is optionally substituted with one to two substituents independently selected from halogen, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl or halogen substituted $C_{1-4}$alkoxy.

In another embodiment of the present invention, $R^5$ is selected from the group consisting of phenyl, a 5 to 6 membered heterocyclyl comprising at least one N atom and a 9 to 10 membered heterocyclyl comprising at least one N atom; wherein the 5 to 6 membered heterocyclyl is optionally substituted with one to three substituents independently selected from oxo, $C_{1-2}$alkyl and halogen substituted $C_{1-2}$alkyl or phenyl; wherein the 9 to 10 membered heterocyclyl is substituted with one to three substituents independently selected from oxo, halogen, $C_{1-2}$alkyl, $C_{1-2}$alkoxy, halogen substituted $C_{1-2}$alkyl, halogen substituted $C_{1-2}$alkoxy, nitro, amino, $C_{1-2}$alkylamino or di($C_{1-2}$alky)amino; wherein the phenyl, whether alone or as part of a substituent group, is optionally substituted with a substituent selected from halogen or nitro.

In another embodiment of the present invention, $R^5$ is selected from the group consisting of phenyl, 3-chlorophenyl, 2-(2-aza-spiro[4.5]decan-3-one), 2-imidazolyl, 3-(1-phenyl-imidazolyl), 1-(2-phenyl-imidazolyl), 1-(2-phenyl-4-methyl-imidazolyl), 1-(2-(4-chlorophenyl)-imidazolyl), 1-(5-(4-chlorophenyl)-imidazolyl), 1-(5-(4-chlorophenyl)-pyrazolyl), 3-(1-(4-chlorophenyl)-pyrazolyl), 2-(1-phenyl-2-pyrazolin-3-one), 3-(1-phenyl-4,5-dihydro-pyrazolyl), 2-(1-(4-chlorophenyl)-1,2-dihydro-pyrazol-3-one), 1-(2-phenyl-2,5-dihydro-pyrazol-5-one), 3-(6-phenyl-pyridazinyl), 3-(6-(4-chlorophenyl)-pyridazinyl), 1-(3-(4-chlorophenyl)-pyridazin-6-one), 2-(4-trifluoromethyl-pyrimidinyl), 2-(4,5-dihydro-oxazolyl), 1-(4-(4-fluorophenyl)-piperidinyl), 1-(4-

(4-chlorophenyl)-piperidinyl), 1-(4-(4-nitrophenyl)-piperidinyl), 2-(pyrrolo[3,4-c]pyridine-1,3-dione), 4-quinazolinyl, 4-(2-amino-quinolinyl), 1-(3,4-dihydro-isoquinolinyl), 2-(6-chloro-3H-quinazolin-4-one), 2-(quinazolin-4-one), 1-(5-chloro-indolin-2,3-dione), 2-(5-chloro-1,3-dioxo-isoindolyl), 1-(3-amino-indazolyl), 1-(3-amino-4-fluoro-indazolyl), 1-(3-amino-5-bromo-indazolyl), 2-(3-amino-5-chloro-indazolyl), 2-(5-chloro-benzthiazolyl), 2-(5-fluoro-benzthiazolyl), 2-(5-ethoxy-benzthiazolyl), 2-(5-nitro-benzthiazolyl), 3-(6-nitro-benzthiazolyl), 3-(benzisothioazolyl), 2-(benzo[d]isothiazol-3-one), 2-(5-chloro-benzoxazolyl), 3-benzisoxazolyl, 3-(5-chloro-benzisoxazolyl), 3-(6-chloro-benzisoxazolyl), 3-(7-chloro-benzioxazolyl), 3-(5-fluoro-benzisoxazolyl), 3-(5-methoxy-benzisoxazolyl), 2-(5-chloro-benzo[d]isoxazol-3-one), 2-(6-chloro-benzo[d]isoxazol-3-one), 2-(7-methyl-benzo[d]isoxazol-3-one), 2-(5-chloro-5,7a-dihydro-benzoimidazolyl), 2-(5-Chloro-6-fluoro-5,7a-dihydro-benzoimidazolyl) and 2-(5-difluoromethoxy-5,7a-dihydro-benzoimidazolyl).

In another embodiment of the present invention, $R^5$ is selected from the group consisting of 3-chlorophenyl, 1-(4-(4-fluorophenyl)-piperidinyl), 2-imidazolyl, 3-(1-phenyl-imidazolyl), 1-(2-(4-chlorophenyl)-imidazolyl), 1-(5-(4-chlorophenyl)-imidazolyl), 1-(2-phenyl-pyridazinyl), 3-(6-phenyl-pyrazinyl), 3-(1-(4-chlorophenyl)-pyrazolyl), 2-(1-(4-chlorophenyl)-1,2-dihydro-pyrazol-3-one), 2-(3-amino-5-chloro-indazolyl), 1-(3-amino-5-bromo-indazolyl), 2-(5-chloro-1,3-dioxo-isoindolyl), 1-(5-chloro-indolin-2,3-dione), 2-(pyrrolo[3,4-c]pyridine-1,3-dione), 2-(5-chloro-benzo[d]isoxazoly-3-one), 2-(6-chloro-benzo[d]isoxazol-3-one), 2-(5-chloro-5,7a-dihydro-benzoimidazolyl), 2-(5-ethoxy-benzthiazolyl), 2(5-fluoro-benzthiazolyl), 2-(5-nitro-benzthiazolyl), 3-(6-nitro-benzthiazolyl), 2-(5-chloro-benzoxazolyl), 3-benzisoxazolyl, 3-(6-chloro-benzisoxazolyl), 3-(5-chloro-benzisoxazolyl), 4-quinazolinyl, 2-(quinazolin-4-one), 2-(6-chloro-quinazolin-4-one), 4-(2-amino-quinlinyl) and 2-(4,5-dihydro-oxazolyl).

In another embodiment of the present invention, $R^5$ is selected from the group consisting of 3-chlorophenyl, 2-imidazolyl, 1-(5-(4-chlorophenyl)-imidazolyl), 2-(5-chloro-benzo[d]isoxazoly-3-one), 2-(6-chloro-benzo[d]isoxazol-3-one), 3-(6-chloro-benzisoxazolyl), 3-(5-chloro-benzisoxazolyl) and 4-quinazolinyl.

In another embodiment of the present invention, $R^5$ is selected from the group consisting of a phenyl substituted 5 to 6 membered heteroaryl comprising at least one N atom and 9 to 10 membered heterocycloalkyl comprising at least one N atom; wherein the phenyl on the 5 to 6 membered heteroaryl is optionally substituted with a halogen; wherein the 5 to 6 membered heteroaryl or the 9 to 10 membered heterocycloalkyl is optionally substituted with one to two substituents independently selected from halogen or oxo.

In another embodiment of the present invention, $R^5$ is selected from the group consisting of 1-(2-phenyl-imidazolyl); 2-(5-chloro-benzothiazolyl); 2-(5-chloro-benzoxazolyl); 1-(5-(4-chlorophenyl)-imidazolyl); 3-(1-(4-chlorophenyl)-imidazolyl), 2-(1-(4-Chloro-phenyl)-1,2-dihydro-pyrazol-3-one), 1-(2-(4-chlorophenyl)-imidazolyl), 2-(6-(4-chlorophenyl)-3-oxo-pyridazinyl) and 1-(5-(4-chlorophenyl)-imidazolyl).

In an embodiment of the present invention, $R^5$ is selected from the group consisting of a 5 to 6 membered heterocyclyl group comprising at least one N atom and a 9 to 10 membered heterocyclyl group comprising at least one N atom; wherein the 5 to 6 membered heterocyclyl group comprising at least one N atom and the 9 to 10 membered heterocyclyl group comprising at least one N atom are optionally substituted as herein defined.

In another embodiment of the present invention, $R^5$ is phenyl or substituted phenyl, wherein the substituents on the phenyl are one or more substituents independently selected from halogen, nitro, cyano, amino, $C_{1-4}$alkylamino, di($C_{1-4}$alkyl)amino, $C_{1-4}$alkyl, $C_{1-4}$alkoxy, halogen substituted $C_{1-4}$alkyl or halogen substituted $C_{1-4}$alkoxy. Preferably, $R^5$ is phenyl or chlorophenyl.

In another embodiment of the present invention, $R^5$ is selected from the group consisting of phenyl substituted 5 to 6 membered heteroaryl comprising at least one N atom and 9 to 10 membered heteroaryl comprising at least one N atom; wherein the phenyl on the 5 to 6 membered heteroaryl is optionally substituted with a halogen; wherein the heteroaryl is optionally substituted with one to two substituents independently selected from oxo, nitro, amino, $C_{1-2}$akylamino or di($C_{1-2}$alkyl)amino;

In another embodiment of the present invention, $R^5$ is selected from the group consisting of 1-(2-amino-5-chloro-benzimidazolyl), 1-(2-(4-chlorophenyl)-imidazolyl), 1-(3-phenyl-imidazolyl), 1-(5-(4-chlorophenyl)-imidazolyl), 2-(1H-quinazolin-4-one), 3-(6-phenyl-pyridazinyl), 1-(3-(4-chlorophenyl)-pyridazin-6-one) and 3-(6-nitro-benzthiazolyl).

In another embodiment of the present invention, $R^5$ is selected from the group consisting of 1-(2-(4-chlorophenyl)-imidazolyl), 1-(5-(4-chlorophenyl)-imidazolyl) and 3-(6-phenyl-pyrizadinyl).

In an embodiment of the present invention, $R^A$, $R^B$, $R^C$, $R^D$, $R^E$, $R^F$, $R^G$, $R^H$ and $R^J$ are each independently selected from the group consisting of hydrogen and $C_{1-2}$ alkyl. In another embodiment of the present invention, $R^A$, $R^B$, $R^C$, $R^D$, $R^E$, $R^F$, $R^G$, $R^H$ and $R^J$ are each independently selected from the group consisting of hydrogen and methyl.

In an embodiment of the present invention, the -($L^1$)$_a$-$R^5$ bond is in the R configuration and the —OR$^O$ bond is in the S configuration.

In an embodiment, the present invention is directed to compounds of formula (I) and/or formula (II) wherein X is CR$^4$ and $R^5$ is other than 6-purinyl or 1-(2-oxo-pyridyl). In another embodiment, the present invention is directed to compounds of formula (I) and/or formula (II) wherein X is CR$^4$ and $R^5$ is other than 1-pyrrolidinyl, 1-pyrrolidin-2-one, 1-(5-methyl-pyrrolidin-2-one), 1-piperidinyl, 1-piperidin-2-one or 4-morpholinyl. In another embodiment, the present invention is directed to compounds of formula (I) and/or formula (II) wherein X is CR$^4$ and $R^5$ is other than 1-(1,2,3,5-tetrazolyl) or 1-(4-methyl-1,2,3,5-tetrazolyl).

In an embodiment, the present invention is directed to compounds of formula (I) and/or formula (II) wherein X is CR$^4$ and -($L^1$)$_a$-$R^5$ is other than 1-pyrrolidin-2-one or 1-piperidin-2-one. In another embodiment, the present invention is directed to compounds of formula (I) and/or formula (II) wherein X is CR$^4$ and -($L^1$)$_a$-$R^5$ is other than 1-pyrrolidinyl, 1-piperidinyl, 1-(2-hydroxy-pyrroldinyl) or 1-(2-hydroxy-piperidinyl).

Additional embodiments of the present invention, include those wherein the substituents selected for one or more of the variables defined herein (i.e. $R^1$, $R^2$, $R^3$, X, a, $L^1$ and $R^5$) are independently selected to be any individual substituent or any subset of substituents selected from the complete list as defined herein.

Representative compounds of the present invention are as listed in Tables 1-6, below. For compounds wherein a is 1 ($L^1$ is present) the $L^1$ substituent is incorporated into the molecule as written. For example, wherein $L^1$ is —NH—SO$_2$—, the nitrogen of the —NH portion is bound to the core and the sulfur of the SO$_2$— portion is bound to the R$^5$ group. For starred bonds, the stereo-orientation is listed in the corresponding column. For example, in Table 1 the column titled "*R$^5$" indicates the orientation of the R$^5$ bond. Further, the designation "Rac" is intended to indicate that the compound was prepared as a mixture of stereo-configurations at the starred bonds, with the limitation that the starred bonds are always in a trans orientation relative to each other. The R and S designations are intended to indicate that the compound was prepared with an excess of one stereo-configuration at the starred bond-center.

TABLE 1

Compounds of Formula (I)

| ID No | R$^3$ | R$^4$ | *R$^5$ | R$^5$ | *OH |
|---|---|---|---|---|---|
| 9 | H | cyan | Rac | 1-(2-phenyl-4-methyl-imidazolyl) | Rac |
| 10 | H | cyano | R | 1-(5-(4-chlorophenyl)-pyrazolyl) | S |
| 12 | H | cyano | Rac | 1-(2-(4-chlorophenyl)-imidazolyl) | Rac |
| 13 | H | chloro | Rac | 2-(1-phenyl-pyrazolin-3-one) | Rac |
| 14 | H | cyano | Rac | 1-(3-(4-chlorophenyl)-pyridazin-6-one) | Rac |
| 15 | H | cyano | Rac | 2-(1-(4-chlorophenyl)-1,2-dihydro-pyrazol-3-one) | Rac |
| 18 | H | cyano | Rac | 1-(5-(4-chlorophenyl)-imidazolyl) | Rac |
| 24 | H | cyano | R | 1-(5-chloro-indolin-2,3-dione) | S |
| 26 | H | cyano | R | 2-(pyrrolo[3,4-c]pyridine-1,3-dione) | S |
| 30 | H | cyano | R | 2-(benzo[d]isothiazol-3-one) | S |
| 32 | H | cyano | R | 2-(7-methyl-benzo[d]isoxazol-3-one) | S |
| 33 | H | cyano | R | 2-(3-amino-5-chloro-indazolyl) | S |
| 34 | H | cyano | R | 2-(2-aza-spiro[4.5]decan-3-one) | S |
| 35 | H | cyano | R | 1-(3-amino-5-bromo-indazolyl) | S |
| 36 | H | cyano | R | 1-(3-amino-4-fluoro-indazolyl) | S |
| 37 | H | cyano | R | 1-(3-amino-indazolyl) | S |
| 47 | H | cyano | Rac | 1-(2-phenyl-imidazolyl) | Rac |
| 48 | H | cyano | Rac | 1-(4-(4-fluorophenyl)-piperidinyl) | Rac |
| 49 | H | chloro | Rac | 1-(2-phenyl-imidazolyl) | Rac |
| 50 | H | cyano | Rac | 1-(4-(4-chlorophenyl)-piperidinyl) | Rac |
| 51 | H | cyano | Rac | 1-(4-(4-nitrophenyl)-piperidinyl) | Rac |
| 62 | H | cyano | Rac | 1-(2-phenyl-2,5-dihydro-pyrazol-5-one) | Rac |
| 76 | H | phenyl-sulfonyl- | R | 2-(5-chloro-benzo[d]isoxazol-3-one) | S |
| 78 | H | phenyl-sulfonyl- | R | 2-(6-chloro-benzo[d]isoxazol-3-one) | S |
| 84 | H | 1-piperidinyl-sulfonyl- | R | 2-(6-chloro-benzo[d]isoxazol-3-one) | S |
| 86 | H | diethyl-amino-sulfonyl- | R | 2-(6-chloro-benzo[d]isoxazol-3-one) | S |
| 94 | chloro | chloro | R | 2-(6-chloro-benzisoxazol-3-one) | S |
| 96 | H | phenyl-carbonyl- | R | 2-(6-chloro-benzo[d]isoxazol-3-one) | S |
| 98 | H | 4-methoxy-phenyl-sulfonyl- | R | 2-(6-chloro-benzo[d]isoxazol-3-one) | S |
| 100 | H | 3-fluoro-phenyl-sulfonyl- | R | 2-(6-chloro-benzo[d]isoxazol-3-one) | S |
| 102 | H | 4-chloro-phenyl-sulfonyl- | R | 2-(6-chloro-benzo[d]isoxazol-3-one) | S |
| 115 | H | cyano | R | 2-(5-chloro-1,3-dioxo-isoindolyl) | S |
| 117 | H | cyano | R | 2-(6-chloro-benzo[d]isoxazol-3-one) | S |

TABLE 2

Compounds of Formula (I)

| ID No. | R$^3$ | R$^4$ | *L$^1$–R$^5$ | L$^1$ | R$^5$ | *OH |
|---|---|---|---|---|---|---|
| 1 | H | cyano | Rac | NH | 2-(5-chloro-benzthiazolyl) | Rac |
| 2 | H | cyano | Rac | NH | 2-(5-chloro-benzoxazolyl) | Rac |

TABLE 2-continued

Compounds of Formula (I)

| ID No. | R³ | R⁴ | * L¹–R⁵ | L¹ | R⁵ | * OH |
|---|---|---|---|---|---|---|
| 3 | H | chloro | Rac | OC(O) | 3-chlorophenyl | Rac |
| 4 | H | cyano | Rac | NH | 2-(5-ethoxy-benzthiazolyl) | Rac |
| 5 | H | cyano | Rac | NH | 2-(5-fluoro-benzthiazolyl) | Rac |
| 6 | H | cyano | Rac | NH | 2-(5-nitro-benzthiazolyl) | Rac |
| 7 | H | cyano | Rac | NH | 2-(6-chloro-1H-quinazolin-4-one) | Rac |
| 8 | H | cyano | Rac | O | 4-(2-amino-quinolinyl) | Rac |
| 16 | H | cyano | Rac | S | 2-(5-difluoromethoxy-5,7a-dihydro-benzoimidazolyl) | Rac |
| 17 | H | cyano | Rac | SO₂ | 2-(5-chloro-benzoxazolyl) | Rac |
| 19 | H | cyano | Rac | SO₂ | 3-(6-chloro-benzisoxazolyl) | Rac |
| 20 | H | cyano | Rac | O | 3-(benzisothioazolyl) | Rac |
| 22 | H | cyano | R | O | 3-(6-chloro-benzisoxazolyl) | S |
| 23 | H | cyano | R | O | 3-benzisoxazolyl | S |
| 25 | H | cyano | R | S | 2-imidazolyl | S |
| 27 | H | cyano | R | O—P(O)-(phenyl) | phenyl | S |
| 28 | H | cyano | R | NH—P(O)-(methyl) | phenyl | S |
| 29 | H | cyano | R | S | 2-(5-chloro-5,7a-dihydro-benzoimidazolyl) | S |
| 38 | H | cyano | R | O | 3-(5-chloro-benzisoxazolyl) | S |
| 39 | H | cyano | R | NH | 3-(5-chloro-benzisoxazolyl) | S |
| 40 | H | cyano | R | O | 4-quinazolinyl | S |
| 41 | H | cyano | R | O | 3-(6-nitro-benzthiazolyl) | S |
| 42 | H | cyano | R | S | 1-(3,4-dihydro-isoquinolinyl) | S |
| 43 | H | cyano | R | S | 2-(4-trifluoromethyl-pyrimidinyl) | S |
| 44 | H | cyano | R | O | 3-(5-methoxy-benzisoxazolyl) | S |
| 52 | H | cyano | Rac | O | 3-(6-phenyl-pyridazinyl) | Rac |
| 55 | H | cyano | Rac | O | 3-(1-(4-chlorophenyl)-pyrazolyl) | Rac |
| 56 | H | cyano | Rac | O | 3-(6-(4-chlorophenyl)-pyridazinyl) | Rac |
| 58 | H | cyano | Rac | O | 3-(1-phenyl-imidazolyl) | Rac |
| 59 | H | chloro | Rac | O | 3-(1-phenyl-4,5-dihydro-pyrazolyl) | Rac |
| 60 | H | chloro | Rac | O | 3-(1-phenyl-imidazolyl) | Rac |
| 64 | H | cyano | R | NH | 2-(6-chloro-3H-quinazolin-4-one) | S |
| 65 | H | cyano | R | NH-P(O)-(phenyl) | phenyl | S |

TABLE 2-continued

Compounds of Formula (I)

| ID No. | R³ | R⁴ | * L¹–R⁵ | L¹ | R⁵ | * OH |
|---|---|---|---|---|---|---|
| 66 | H | cyano | R | NH—SO₂ | 3-chlorophenyl | S |
| 67 | H | cyano | R | NH | 3-(6-chloro-benzisoxazolyl) | S |
| 68 | H | cyano | R | S | 2-(4,5-dihydro-oxazolyl) | S |
| 70 | H | cyano | R | O | 3-(5-fluoro-benzisoxazolyl) | S |
| 71 | H | cyano | R | SO₂ | 2-imidazolyl | S |
| 72 | H | cyano | R | SO₂ | 2-(5-Chloro-6-fluoro-5,7a-dihydro-benzoimidazolyl) | S |
| 73 | H | phenyl-sulfonyl- | R | NH | 3-(6-chloro-benzisoxazolyl) | S |
| 74 | H | phenyl-sulfonyl- | R | NH | 3-(5-chloro-benzisoxazolyl) | S |
| 75 | H | phenyl-sulfonyl- | R | O | 3-(5-chloro-benzisoxazolyl) | S |
| 77 | H | phenyl-sulfonyl- | R | O | 3-(6-chloro-benzisoxazolyl) | S |
| 79 | H | diethyl-amino-sulfonyl- | R | O | 3-(6-chloro-benzisoxazolyl) | S |
| 80 | H | diethyl-amino-sulfonyl- | Rac | NH | 3-(6-chloro-benzisoxazolyl) | Rac |
| 81 | H | diethyl-amino-sulfonyl- | R | NH | 3-(6-chloro-benzisoxazolyl) | S |
| 82 | H | diethyl-amino-sulfonyl- | R | NH | 3-(7-chloro-benzioxazolyl) | S |
| 83 | H | 1-piperidinyl-sulfonyl- | R | O | 3-(6-chloro-benzioxazolyl) | S |
| 85 | H | diethyl-amino-sulfonyl- | R | O | 3-(5-chloro-benzisoxazolyl) | S |
| 87 | H | phenyl-sulfonyl- | R | NH | 3-(7-chloro-benzioxazolyl) | S |
| 88 | H | 1-piperidinyl-sulfonyl- | R | NH | 3-(5-chloro-benzisoxazolyl) | S |
| 89 | H | diethyl-amino-carbonyl- | R | NH | 3-(5-chloro-benzisoxazolyl) | S |
| 90 | H | diethyl-amino-carbonyl- | R | O | 3-(6-chloro-benzisoxazolyl) | S |
| 91 | chloro | chloro | R | NH | 3-(5-chloro-benzisoxazolyl) | S |
| 92 | H | phenyl-carbonyl- | R | NH | 3-(5-chloro-benzisoxazolyl) | S |
| 93 | chloro | chloro | R | O | 3-(6-chloro-benzisoxazolyl) | S |
| 95 | H | phenyl-carbonyl- | R | O | 3-(6-chloro-benzisoxazolyl) | S |
| 97 | H | 4-methoxy-phenyl-sulfonyl- | R | O | 3-(6-chloro-benzisoxazolyl) | S |
| 99 | H | 3-fluoro-phenyl-sulfonyl- | R | O | 3-(6-chloro-benzisoxazolyl) | S |
| 101 | H | 4-chloro-phenyl-sulfonyl- | R | O | 3-(6-chloro-benzisoxazolyl) | S |
| 103 | H | 3-fluoro-phenyl-sulfonyl- | R | NH | 3-(5-chloro-benzisoxazolyl) | S |
| 104 | H | 4-methoxy-phenyl-sulfonyl- | R | NH | 3-(5-chloro-benzisoxazolyl) | S |
| 118 | H | cyano | Rac | NH | 2-quinazolin-4-one | Rac |

TABLE 3

Compounds of Formula (I)

| ID No. | R⁰ | R¹ + R² together | *L¹–R⁵ | L¹ | R⁵ | *OH |
|---|---|---|---|---|---|---|
| 200 | H | (tetrahydrothiopyran-1,1-dioxide) | R | O | 3-(6-chloro-benzisoxazolyl) | S |
| 201 | H | (tetrahydrothiopyran-1,1-dioxide) | R | NH—C(O) | 3-chlorophenyl | S |
| 202 | 3-chloro-phenyl carbonyl- | (tetrahydrothiopyran-1,1-dioxide) | R | NH—C(O) | 3-chlorophenyl | S |

TABLE 4

Compounds of Formula (II)

| ID No | R³ | R⁴ | R⁵ |
|---|---|---|---|
| 45 | H | cyano | 1-(2-amino-5-chloro-benzimidazolyl) |
| 54 | H | cyano | 1-(2-(4-chloro-phenyl)-imidazolyl) |
| 57 | H | cyano | 1-(3-(4-chlorophenyl)-pyradazin-6-one) |
| 61 | H | cyano | 1-(3-phenyl-imidazolyl) |
| 63 | H | cyano | 1-(5-(4-chloro-phenyl)-imidazolyl) |

TABLE 5

Compounds of Formula (II)

| ID No | R³ | R⁴ | L¹ | R⁵ |
|---|---|---|---|---|
| 46 | H | cyano | NH | 2-(1H-quinazolin-4-one) |
| 53 | H | cyano | O | 3-(6-phenyl-pyridazinyl) |
| 69 | H | cyano | NH | 3-(6-nitro-benzthiazolyl) |

TABLE 6

Compounds of Formula (I)

| ID No. | *L¹–R⁵ | (L¹)ₐ | R⁵ | *OH |
|---|---|---|---|---|
| 105 | Rac | a = 0 | 1-(2-phenyl-imidazolyl) | Rac |
| 106 | Rac | NH | 2-(5-chloro-benzthiazolyl) | Rac |
| 107 | Rac | NH | 2-(5-chloro-benzoxazolyl) | Rac |
| 108 | Rac | a = 0 | 1-(5-(4-chlorophenyl)-imidazolyl) | Rac |
| 109 | Rac | O | 3-(1-(4-chlorophenyl)-imidazolyl) | Rac |
| 110 | Rac | a = 0 | 2-(1-(4-Chloro-phenyl)-1,2-dihydro-pyrazol-3-one) | Rac |
| 111 | Rac | a = 0 | 1-(2-(4-chlorophenyl)-imidazolyl) | Rac |
| 112 | Rac | a = 0 | 2-(6-(4-chlorophenyl)-3-oxo-pyridazinyl) | Rac |
| 113 | Rac | a = 0 | 1-(5-(4-chlorophenyl)-imidazolyl) | Rac |

Compounds of formula (I) and (II) wherein X is $CR^4$ may be prepared according to the process outlined in Scheme 1.

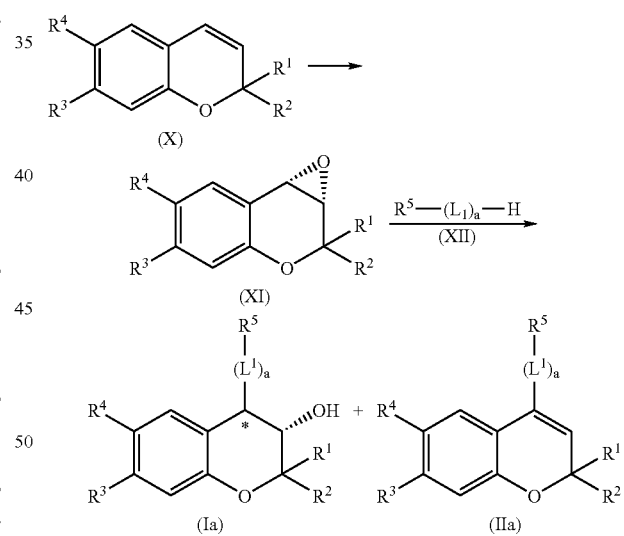

Scheme 1

Accordingly, a suitably substituted compound of formula (X), a known compound or compound prepared by known methods is reacted with a suitably selected oxidant such as NaClO, mCPBA and the like, in the presence of a (S,S)-(−)-N,N'-Bis(3,5-di-tert-butylsalicylidene)-1,2-diaminocyclohexylmanganese(III) chloride catalyst, hereinafter referred to as (S,S)-Jacobasen's catalyst or (R,R)-(−)-N,N'-Bis(3,5-di-tert-butylsalicylidene)-1,2-diaminocyclohexylmanganese (III) chloride hereinafter referred to as (R,R)-Jacobsen's catalyst, preferably at a temperature in the range of from about 0° C. and about 25° C., more preferably at a temperature of about 0° C., to yield the corresponding compound of formula (XI).

The compound of formula (XI) is reacted with a suitably substituted compound of formula (XII), a known compound or compound prepared by known methods, in the presence of a base such as pyridine, $K_2CO_3$, NaH, and the like, in an organic solvent such as DMF, DMAC, EtOH, and the like, at a temperature in the range of from about 50° C. and about 100° C., to yield a mixture of the corresponding compounds of formula (Ia) and formula (IIa).

Preferably, the compound of formula (Ia) and formula (IIa) are separated and optionally purified according to know methods. For example, the compound of formula (Ia) and formula (IIa) may be separated by column chromatography, and the like; and optionally purified by recrystallization, and the like.

Compounds of formula (I) wherein X is $CR^4$ and $-(L^1)_a-R^5$ is $-NH-R^5$ may alternatively be prepared according to the process outlined in Scheme 2.

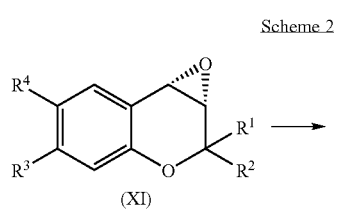

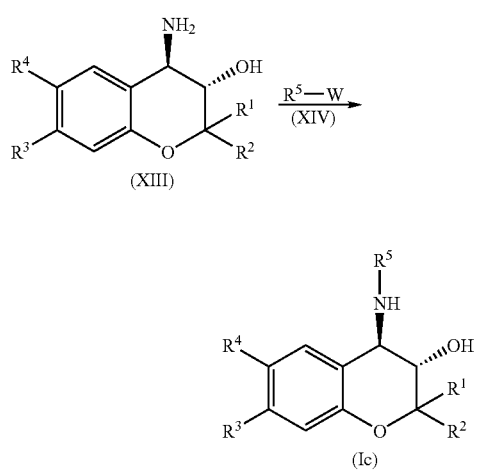

Accordingly, a suitably substituted compound of formula (XI), is reacted with a source of ammonia such as $NH_4OH$, $NH_3$, and the like, in an organic solvent such as methanol, DMF, and the like, preferably at a temperature in the range of from about 25° C. and about 80° C., to yield the corresponding compound of formula (XIII).

The compound of formula (XIII) is reacted with a suitably substituted compound of formula (XIV), wherein W is a suitable leaving group, a known compound or compound prepared by known methods, in the presence of a base, such as TEA, DIPEA, pyridine, and the like, in an organic solvent such as DCM, THF, and the like, at a temperature in the range of from about −10° C. to about 25° C., to yield the corresponding compound of formula (Ic).

Compounds of formula (I) wherein X is $CR^4$ and $-(L^1)_a-$ is $-NH-C(O)-$ may be prepared according to the process outlined in Scheme 3.

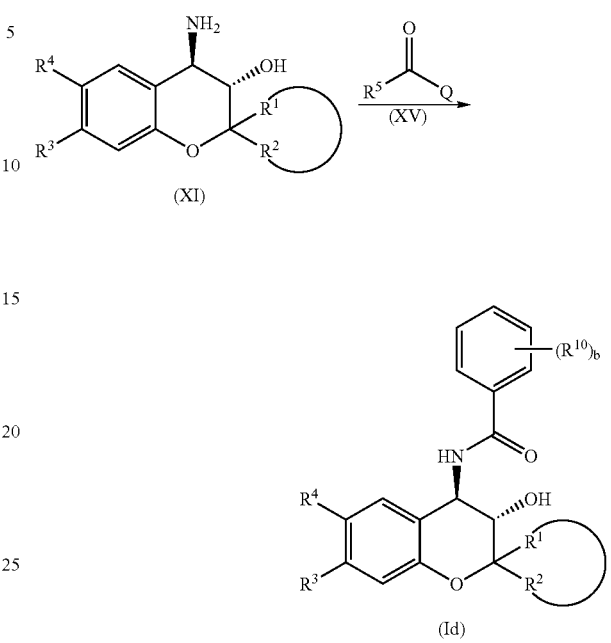

Accordingly, a suitably substituted compound of formula (XI), is reacted with a suitably substituted compound of formula (XV), wherein Q is a suitable leaving group, a known compound or compound prepared by known methods, in the presence of a base, such as TEA, DIPEA, pyridine, and the like, in an organic solvent such as DCM, THF, and the like, at a temperature in the range of from about −10° C. to about 25° C., to yield the corresponding compound of formula (Id).

One skilled in the art will recognize that the compound of formula (Id) may be further, optionally reacted according to known methods (e.g. alkylation) to yield the corresponding compound of formula (I) wherein $-(L^1)_a-$ is $-NR^E-C(O)-$ and $R^E$ is other than hydrogen.

Compounds of formula (I) wherein X is $CR^4$, a is 0 ($L^1$ is absent) and $R^5$ is a heterocyclyl group bound through a nitrogen atom may alternatively be prepared via a cyclization reaction. As an example, preparation of a compound of formula (I) wherein $R^5$ is isoindol-1,3-dione is outlined in Scheme 4.

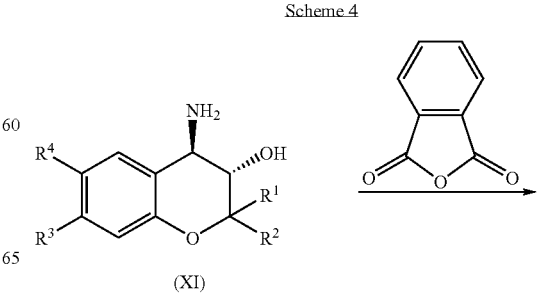

-continued

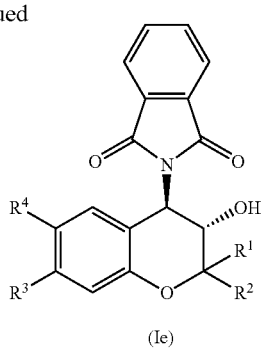
(Ie)

Accordingly, a suitably substituted compound of formula (XII), is reacted with isobenzofuran-1,3-dione, a known compound, neatly in a sealed tube, at a temperature in the range of from about 150° C. to about 200° C., to yield the corresponding compound of formula (Ie).

One skilled in the art will recognize that compounds of formula (II) may alternatively be prepared from the corresponding compound of formula (I) by dehydration, according to known methods, for example by reacting the compound of formula (I) with an acid such as PTSA, CSA, and the like or by reacting with a reagent such as Burgess' reagent. One skilled in the art will further recognize that reactive groups on the compound of formula (I) may need to be protected prior to the reaction and then de-protected, according to known methods.

Compounds of formula (X) are known compounds or compounds that may be prepared according to known methods. For example, compounds of formula (X) may be prepared according to the process outlined in Scheme 5.

Scheme 5

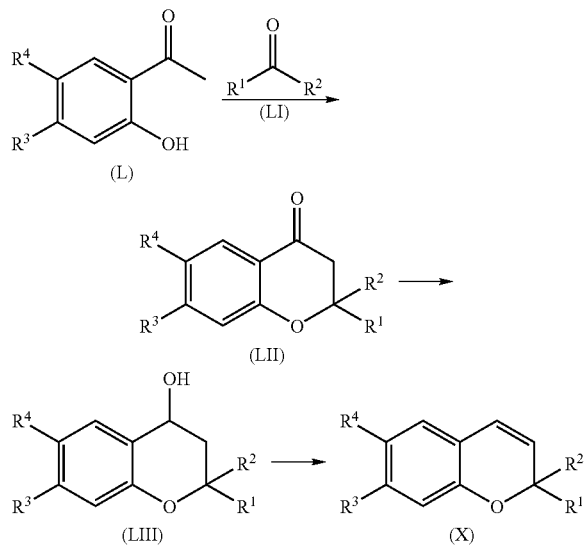

Accordingly, a suitably substituted compound of formula (L), a known compound or compound prepared by known methods, is reacted with a suitably substituted compound of formula (LI), a known compound or compound prepared by known methods, in the presence of a base such pyrrolidine, piperidine, and the like, preferably at a temperature greater than about room temperature, more preferably at about reflux temperature, to yield the corresponding compound of formula (LII).

The compound of formula (LII) is reacted with a suitably selected reducing agent such as $NaBH_4$, LAH, and the like, in an organic solvent such as methanol, ethanol, and the like, at a temperature in the range of from about −20° C. to about 5° C., to yield the corresponding compound of formula (LIII).

The compound of formula (LIII) is reacted with acid such as PTSA, CSA, and the like, in an organic solvent such as benzene, toluene and the like, at a temperature in the range of from about 80° C. to about 110° C., to yield the corresponding compound of formula (X).

Compounds of formula (X) may alternatively be prepared according to the process outlined in Scheme 6.

Scheme 6

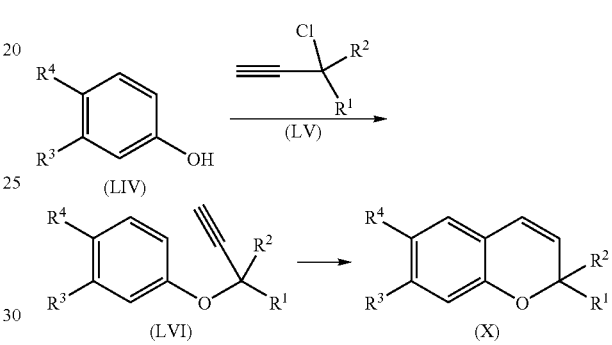

Accordingly, a suitably substituted compound of formula (LIV), a known compound or compound prepared by known methods, is reacted with a suitably substituted compound of formula (LV), a known compound or compound prepared by known methods, in the presence of a base such as $K_2CO_3$, NaH, and the like, in the presence of a catalyst such as KI, $Bu_4NI$, CuI, and the like, in an organic solvent such as acetone, THF, dioxane, and the like, preferably at a temperature in the rage of form about 50° C. to about 80° C., to yield the corresponding compound of formula (LVI).

The compound of formula (LVI) is heated in an organic solvent such as xylene, toluene, dioxane, and the like, preferably to a temperature in the range of from about 100° C. to about 180° C., preferably for about 120° C. to about 150° C., preferably for about 120 to about 130 hours, to yield the corresponding compound of formula (X).

One skilled in the art will recognize that compounds of formula (I) and compounds of formula (II) wherein X is N may be similarly prepared according to the processes described in the Schemes above, by selecting and substituting suitably substituted starting materials. For example, in Scheme 1, compounds of formula (I) and (II) wherein X is N may be prepared by substituting a compound of formula (Xn)

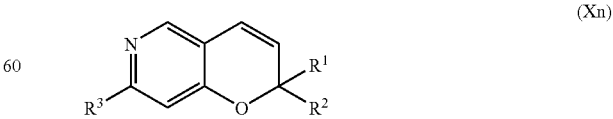

for the compound of formula (X) and completing the reactions as described. Similar substitutions as would be appropriate for Scheme 2-6 will be evident to those skilled in the art.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

One skilled in the art will recognize that wherein a reaction step of the present invention may be carried out in a variety of solvents or solvent systems, said reaction step may also be carried out in a mixture of the suitable solvents or solvent systems.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more of the compounds of the present invention selected as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 50-100 mg and may be given at a dosage of from about 0.01 to about 10.0 mg/kg/day, preferably at a dosage of from about 0.05 to about 5.0 mg/kg/day, more preferably at a dosage of from about 0.1 to about 2.0 mg/kg/day. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders related to ion channels, for example potassium ion channels, described in the present invention may also be carried out using a pharmaceutical composition comprising any of the compounds as defined herein and a pharmaceutically acceptable carrier. The pharmaceutical composition may contain between about 0.01 mg and 1000 mg, preferably about 1 to 500 mg, more preferably, 10 to 100 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders related to ion channels, for example potassium ion channels, is required.

The daily dosage of the products may be varied over a wide range from 0.01 to 1,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500 and 1000 milligrams of the active ingredient for the symptomatic adjustment of the dosage to the patient to be treated. An effective amount of the drug is ordinarily supplied at a dosage level of from about 0.01 mg/kg to about 10 mg/kg of body weight per day. Preferably, the range is from about 0.1 to about 5.0 mg/kg of body weight per day, most preferably, from about 0.5 to about 2.0 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder. One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

In the Examples which follow, racemic compounds are denoted as such in the name. For convenience, the racemic compounds are drawn to show the trans configuration of one of the enantiomers of the racemate.

Example 1

(3S,4R)-3-Hydroxy-4-(2H-imidazol-2-ylsulfanyl)-2,2-dimethyl-chroman-6-carbonitrile (Compound #25)

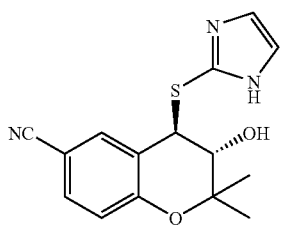

(S,S)-2,2-Dimethyl-1a,7b-dihydro-2H-1,3-dioxa-cyclopropa[a]naphthalene-6-carbonitrile (1 mmoL), 1,3-dihydro-imidazole-2-thione (1 mmoL) and anhydrous $K_2CO_3$ (1.5 mmoL) in DMF (5 mL) were heated at 100° C. for 4~6 hrs. The solid was filtered off and the reaction mixture was partitioned between ethyl acetate and water. The organic layer was washed with saturated $NH_4Cl$, brine, then dried over anhydrous $Na_2SO_4$, filtered and concentrated to yield a yellow oil. Silica gel chromatography separation yielded the title compound as a white solid.

$^1$H NMR: ($CDCl_3$) δ 9.90 (br, 1H), 8.00 (s, 1H), 7.18 (d, J=5.1 Hz, 1H), 7.10 (s, 2H), 6.85 (d, J=5.4 Hz, 1H), 4.35 (d, J=5.4 Hz, 1H), 4.10 (d, J=5.4 Hz, 1H), 1.58 (s, 3H), 1.20 (s, 3H)

MS (m/z): $MH^+$ 302.

Example 2

4-(4,5-Dihydro-oxazol-2-ylsulfanyl)-3-hydroxy-2,2-dimethyl-chroman-6-carbonitrile (Compound #68)

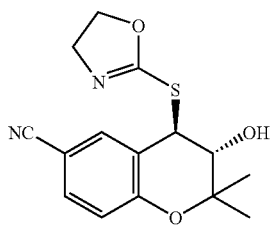

Following the procedure described in the Example 1, using (±)$_{2,2}$-dimethyl-1a,7b-dihydro-2H-1,3-dioxa-cyclopropa[a]naphthalene-6-carbonitrile and 3H-oxazole-2-thione as starting materials, the title compound was prepared as a white solid.

$^1$H NMR: ($CDCl_3$) δ 7.50 (m, 1H), 7.5 (s, 1H), 6.95 (m, 1H), 5.95 (m, 1H), 4.20 (m, 1H), 3.85-3.50 (m, 4H), 2.70 (m, 1H), 1.55 (s, 3H), 1.35 (s, 3H)

MS (m/z): $MH^+$ 396.

Example 3

(3S,4R)-3-Hydroxy-4-(1H-imidazole-2-sulfonyl)-2,2-dimethyl-chroman-6-carbonitrile (Compound #71)

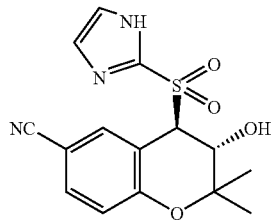

(3S,4R)-3-Hydroxy-4-(2H-imidazol-2-ylsulfanyl)-2,2-dimethyl-chroman-6-carbonitrile (0.8 mmoL) was treated with OXONE (2 mmoL) in MeOH (2 mL) and water (2 mL) at room temperature. After 4 hrs, the solid was filtered off and the solvent was removed. The residue was partitioned between ethyl acetate and water. The aqueous layer was extracted with ethyl acetate three times. The combined organic layer was washed with brine, filtered, dried over anhydrous $Na_2SO_4$ and concentrated to yield crude material, which was purified by silica gel chromatography to yield the title compound as a white solid.

$^1$H NMR (MeOD) δ 8.00 (s, 1H), 7.55 (m, 1H), 7.30 (m, 2H), 6.85 (m, 1H), 4.65 (m, 1H), 4.45 (m, 1H), 1.50 (s, 3H), 1.00 (s, 3H)

MS (m/z): $MH^+$ 334

Example 4

(3S,4R)-4-(5-Chloro-2,3-dioxo-2,3-dihydro-indol-1-yl)-3-hydroxy-2,2-dimethyl-chroman-6-carbonitrile (Compound #24)

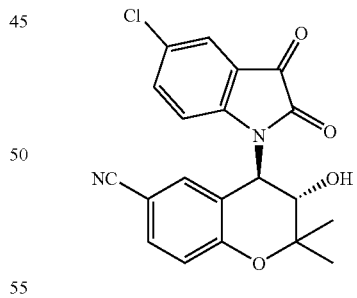

Following the procedure described in the Example 1, using (S,S)-2,2-dimethyl-1a,7b-dihydro-2H-1,3-dioxa-cyclopropa[a]naphthalene-6-carbonitrile and 5-chloro-1H-indole-2,3-dione as starting materials, the title compound was prepared as a white solid.

$^1$H NMR: (MeOD) δ 7.81 (s, 1H), 7.54 (m, 2H), 7.48 (d, J=5.4 Hz, 1H), 7.10 (m, 1H), 6.94 (d, J=5.4 Hz, 1H), 4.80 (d, J=5.4 Hz, 1H), 3.78 (d, J=5.4 Hz, 1H), 1.50 (s, 3H), 1.36 (s, 3H)

MS (m/z): $MH_2O^+ + Na^+$ 423.

Example 5

4R-(3-Amino-6-bromo-indazol-1-yl)-3S-hydroxy-2,2-dimethyl-chroman-6-carbonitrile (Compound #35)

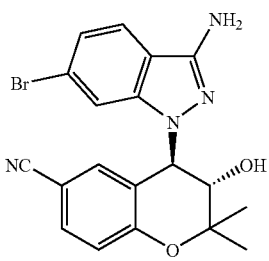

Following the procedure described in the Example 1, using (S,S)-2,2-dimethyl-1a,7b-dihydro-2H-1,3-dioxa-cyclopropa[a]naphthalene-6-carbonitrile and 6-bromo-1H-indazol-3-ylamine as starting materials, the title compound was prepared as a white solid.

$^1$H NMR: (CDCl$_3$) δ 7.65 (s, 1H), 7.55 (m 3H), 6.95 (d, J=5.0 Hz, 1H), 6.80 (s, 1H), 5.80 (d, J=5.0 Hz, 1H), 4.30 (m, 1H), 4.00 (br, 2H), 3.20 (m, 1H), 1.50 (s, 3H), 1.35 (s, 3H)

MS (m/z): MH$^+$ 414.

Example 6

4R-(3-Amino-4-fluoro-indazol-1-yl)-3S-hydroxy-2,2-dimethyl-chroman-6-carbonitrile (Compound #36)

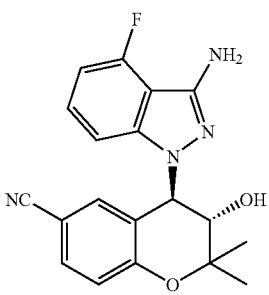

Following the procedure described in the Example 1, using (S,S)-2,2-dimethyl-1a,7b-dihydro-2H-1,3-dioxa-cyclopropa[a]naphthalene-6-carbonitrile and 4-fluoro-1H-indazol-3-ylamine as starting materials, the title compound was prepared as a white solid.

$^1$H NMR: (CDCl$_3$) δ 7.65 (m, 1H), 7.40 (m 1H), 7.25 (m, 1H), 6.90 (d, J=5.0 Hz, 1H), 6.75 (s, 1H), 6.60 (m, 1H), 5.25 (d, J=5.0 Hz, 1H), 4.30 (m, 1H), 4.20 (br, 2H), 1.50 (s, 3H), 1.30 (s, 3H)

MS (m/z): MH$^+$ 353.

Example 7

4R-(3-Amino-indazol-1-yl)-3S-hydroxy-2,2-dimethyl-chroman-6-carbonitrile (Compound #37)

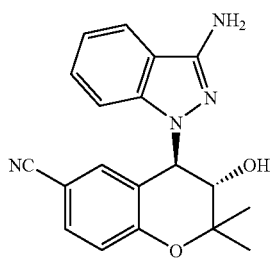

Following the procedure described in the Example 1, using (S,S)-2,2-dimethyl-1a,7b-dihydro-2H-1,3-dioxa-cyclopropa[a]naphthalene-6-carbonitrile and 1H-indazol-3-ylamine as starting materials, the title compound was prepared as a white solid.

$^1$H NMR: (CDCl$_3$) δ 7.75 (s, 1H), 7.50 (m 1H), 7.40 (m, 2H), 6.90 (m, 1H), 6.80 (d, J=5.0 Hz, 1H), 4.50 (d, J=5.0 Hz, 1H), 4.30 (m, 1H), 4.20 (br, 2H), 3.75 (br, 2H), 3.50 (d, J=5.0 Hz, 1H), 1.45 (s, 3H), 1.20 (s, 3H)

MS (m/z): MH$^+$ 335.

Example 8

4R-(3-Amino-5-chloro-indazol-1-yl)-3S-hydroxy-2,2-dimethyl-chroman-6-carbonitrile (Compound #33)

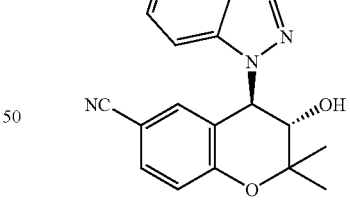

Following the procedure described in the Example 1, using (S,S)-2,2-dimethyl-1a,7b-dihydro-2H-1,3-dioxa-cyclopropa[a]naphthalene-6-carbonitrile and 5-chloro-1H-indazol-3-ylamine as starting materials, the title compound was prepared as a white solid.

$^1$H NMR: (CDCl$_3$) δ 7.50 (m, 1H), 7.15 (m, 2H), 7.05 (m, 2H), 6.85 (m, 1H), 5.85 (m, 1H), 5.35 (m, 1H), 1.62 (s, 3H), 1.38 (s, 3H)

MS (m/z): MH$^+$ 351

Example 9

4-(2-Amino-quinolin-4-yloxy)-3-hydroxy-2,2-dimethyl-chroman-6-carbonitrile (Compound #8)

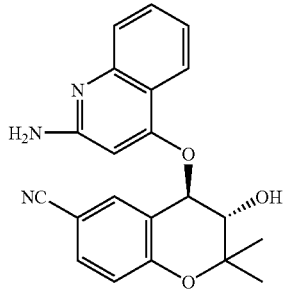

Following the procedure in Example 1, using (±)-2,2-dimethyl-1a,7b-dihydro-2H-1,3-dioxa-cyclopropa[a]naphthalene-6-carbonitrile and 2-amino-quinolin-4-ol as starting materials, the title compound was prepared as a white solid.

¹H NMR: (CDCl₃) δ 7.72 (d, J=7.5 Hz, 1H), 7.49 (m, 4H), 7.05 (t, J=4.5 Hz, 1H), 6.95 (d, J=7.5 Hz, 1H), 6.30 (s, 1H), 5.45 (d, J=5.0 Hz, 1H), 4.85 (br, s, 2H), 4.15 (d, J=5.0 Hz, 1H), 1.60 (s, 3H), 1.49 (s, 3H)

MS (m/z): MH⁺ 362.

Example 10

3-Hydroxy-2,2-dimethyl-4-(5-oxo-2-phenyl-2,5-dihydro-pyrazol-1-yl)-chroman-6-carbonitrile (Compound #62)

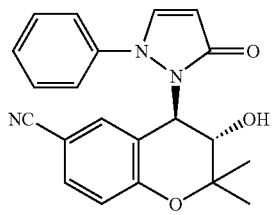

and 3-Hydroxy-2,2-dimethyl-4-(1-phenyl-1H-pyrazol-3-yloxy)-chroman-6-carbonitrile (Compound #58)

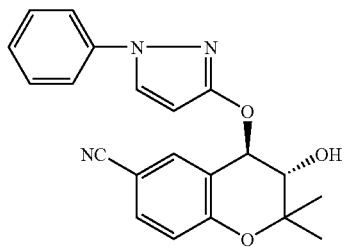

Following the procedure in Example 1, using (±)-2,2-dimethyl-1a,7b-dihydro-2H-1,3-dioxa-cyclopropa[a]naphthalene-6-carbonitrile and 1-phenyl-1,2-dihydro-pyrazol-3-one as starting materials, the title compounds were prepared as white solids.

Compound # 62:
¹H NMR: (CDCl₃) δ 7.65 (m, 2H), 7.50 (m, 4H), 6.85 (d, J=8.5 Hz, 1H), 5.90 (s, 1H), 3.95 (d, J=5.6 Hz, 1H), 3.55 (d, J=5.6 Hz, 1H), 1.65 (s, 3H), 1.30 (s, 3H)
MS (m/z): MH⁺ 362.

Compound #58:
¹H NMR: (CDCl₃) δ 7.80 (d, J=7.5 Hz, 2H), 7.55 (m, 5H), 7.30 (m, 1H), 6.88 (d, J=7.5 Hz, 1H), 6.10 (s, 1H), 5.58 (s, 1H), 5.51 (d, J=8.0 Hz, 1H), 4.05 (d, J=8.0 Hz, 1H), 1.58 (s, 3H), 1.35 (s, 3H)
MS (m/z): MH⁺ 342.

Example 11

2-(6-Chloro-3-hydroxy-2,2-dimethyl-chroman-4-yl)-1-phenyl-pyrazolidin-3-one (Compound #13)

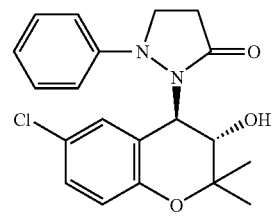

and 6-Chloro-2,2-dimethyl-4-(1-phenyl-1H-pyrazol-3-yloxy)-chroman-3-ol (Compound #60)

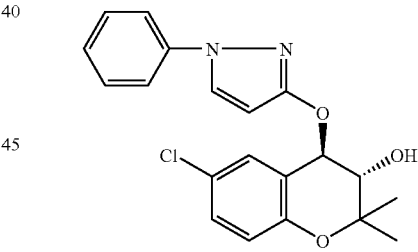

and 6-Chloro-2,2-dimethyl-4-(1-phenyl-4,5-dihydro-1H-pyrazol-3-yloxy)-chroman-3-ol (Compound #59)

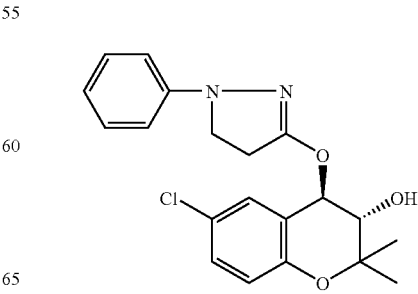

Following the procedure in Example 1, using (±)-2,2-dimethyl-1a,7b-dihydro-2H-1,3-dioxa-cyclopropa[a]naphthalene-6-chloride and 1-phenyl-pyrazolidin-3-one as starting materials, the title compounds were prepared as white solids.

Compound #13:
¹H NMR: (CDCl₃) δ 7.32~7.05 (m, 7H), 6.65 (d, J=7.5 Hz, 1H), 5.21 (d, J=8.0 Hz, 1H), 3.80 (q, J=8.5 Hz, 2H), 3.78 (d, J=8.0 Hz, 1H), 2.75 (m, 2H), 1.42 (s, 3H), 1.22 (s, 3H)
MS (m/z): MH⁺ 374.

Compound #60:
¹H NMR: (CDCl₃) δ 7.80 (s, 1H), 7.58 (d, J=8.0 Hz, 1H), 7.45 (m, 3H), 7.35 (d, J=7.5 Hz, 1H), 7.20 (m, 1H), 6.80 (d, J=8.5 Hz, 1H), 6.05 (d, J=2.0 Hz, 1H), 5.60 (d, J=7.5 Hz, 1H), 4.08 (d, J=7.5 Hz, 1H), 1.58 (s, 3H), 1.35 (s, 3H)
MS (m/z): MH⁺ 372.

Compound #59:
¹H NMR: (CDCl₃) δ 7.80 (s, 1H), 7.55 (d, J=8.0 Hz, 2H), 7.48 (m, 3H), 7.29 (d, J=7.5 Hz, 1H), 7.20 (m, 1H), 5.52 (d, J=7.0 Hz, 1H), 4.15 (m, 2H), 4.02 (d, J=7.0 Hz, 1H), 3.50 (t, J=8.5 Hz, 2H), 2.62 (t, J=8.5 Hz, 2H), 1.55 (s, 3H), 1.35 (s, 3H)
MS (m/z): MH⁺ 374.

Example 12

6-Chloro-2,2-dimethyl-4-(2-phenyl-imidazol-1-yl)-chroman-3-ol (Compound #49)

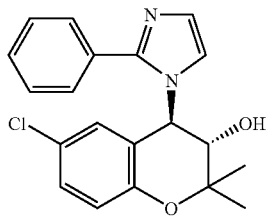

Following the procedure in Example 1, using (±)-2,2-dimethyl-1a,7b-dihydro-2H-1,3-dioxa-cyclopropa[a]naphthalene-6-chloride (literature known) and 2-phenyl-1H-imidazole as starting materials, the title compound was prepared as a white solid.

¹H NMR: (CDCl₃) δ 7.82 (d, J=7.5 Hz, 1H), 7.55 (d, J=7.4 Hz, 1H), 7.38 (m, 4H), 7.02 (s, 1H), 6.78 (d, J=8.5 Hz, 1H), 6.71 (s, 1H), 6.40 (s, 1H), 5.42 (d, J=8.0 Hz, 1H), 4.12 (d, J=7.1 Hz, 1H), 1.58 (s, 3H), 1.22 (s, 3H)
MS (m/z): MH⁺ 355.

Example 13

3-Hydroxy-2,2-dimethyl-4-(2-phenyl-imidazol-1-yl)-chroman-6-carbonitrile (Compound #47)

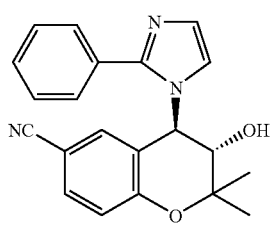

and 2,2-Dimethyl-4-(2-phenyl-imidazol-1-yl)-2H-chromene-6-carbonitrile (Compound #61)

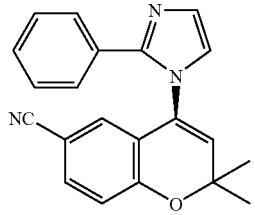

Following the procedure in Example 1, using (±)-2,2-dimethyl-1a,7b-dihydro-2H-1,3-dioxa-cyclopropa[a]naphthalene-6-carbonitrile and 2-phenyl-1H-imidazole as starting materials, the title compounds were prepared as white solids.

Compound #47:
¹H NMR: (CDCl₃) δ 7.82 (d, J=3.5 Hz, 2H), 7.45 (m, 3H), 7.31 (d, J=6.5 Hz, 1H), 6.82 (d, J=7.5 Hz, 1H), 6.60 (s, 1H), 6.32 (s, 1H), 5.32 (d, J=7.5 Hz, 1H), 3.88 (d, J=7.5 Hz, 1H), 1.55 (s, 3H), 1.25 (s, 3H)
MS (m/z): MH⁺ 346.

Compound #61:
¹H NMR: (CDCl₃) δ 7.55 (m, 2H), 7.51 (d, J=7.5 Hz, 1H), 7.32 (m, 5H), 7.05 (s, 1H), 6.95 (d, J=8.0 Hz, 1H), 5.54 (s, 1H), 1.55 (br, s, 3H)
MS (m/z): MH⁺ 328.

Example 14

3-Hydroxy-2,2-dimethyl-4-(4-methyl-2-phenyl-imidazol-1-yl)-chroman-6-carbonitrile (Compound #9)

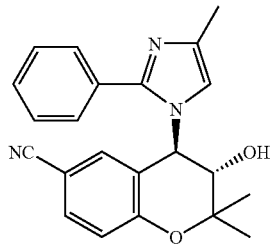

Following the procedure in Example 1, using (±)-2,2-dimethyl-1a,7b-dihydro-2H-1,3-dioxa-cyclopropa[a]naphthalene-6-carbonitrile and 4-methyl-2-phenyl-1H-imidazole as starting materials, the title compound was prepared as a white solid.

¹H NMR: (CDCl₃) δ 7.72 (m, 1H), 7.35 (m, 5H), 6.82 (d, J=7.5 Hz, 1H), 6.72 (s, 1H), 6.31 (s, 1H), 5.35 (d, J=7.8 Hz, 1H), 4.05 (d, J=7.8 Hz, 1H), 2.16 (s, 3H), 1.65 (s, 3H), 1.28 (s, 3H)
MS (m/z): MH⁺ 360.

Example 15

4-[2-(4-Chloro-phenyl)-imidazol-1-yl]-2,2-dimethyl-2H-chromene-6-carbonitrile (Compound #54)

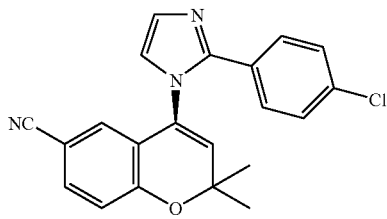

and 4-[2-(4-Chloro-phenyl)-imidazol-1-yl]-3-hydroxy-2,2-dimethyl-chroman-6-carbonitrile (Compound #12)

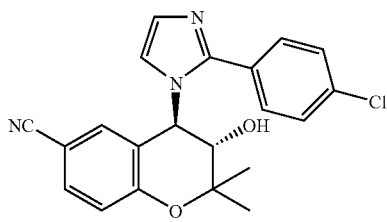

Following the procedure in Example 1, using (±)-2,2-dimethyl-1a,7b-dihydro-2H-1,3-dioxa-cyclopropa[a]naphthalene-6-carbonitrile and 2-(4-chloro-phenyl)-1H-imidazole as starting materials, the title compounds were prepared as white solids.

Compound #54:
¹H NMR: (CDCl₃) δ 7.50 (m, 3H), 7.45-7.35 (m, 2H), 7.00 (m, 4H), 5.60 (s, 1H), 1.50 (m, 6H)
MS (m/z): MH⁺ 363

Compound #12:
¹H NMR: (CDCl₃) δ 7.72 (m, 3H), 7.45-7.35 (m, 4H), 6.85 (m, 2H), 5.90 (br, 1H), 5.30 (m, 1H), 4.02 (m, 1H), 1.65 (s, 3H), 1.28 (s, 3H)
MS (m/z): MH⁺ 381

Example 16

4-[5-(4-Chloro-phenyl)-imidazol-1-yl]-3-hydroxy-2,2-dimethyl-chroman-6-carbonitrile (Compound #18)

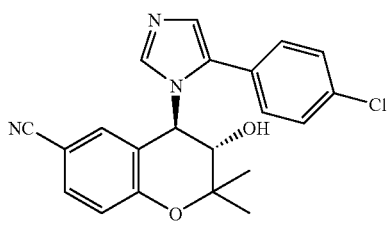

and 4-[5-(4-Chloro-phenyl)-imidazol-1-yl]-2,2-dimethyl-2H-chromene-6-carbonitrile (Compound #63)

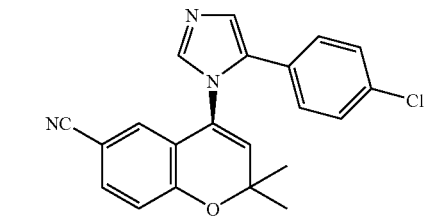

Following the procedure in Example 1, using (±)-2,2-dimethyl-1a,7b-dihydro-2H-1,3-dioxa-cyclopropa[a]naphthalene-6-carbonitrile and 5-(4-chloro-phenyl)-1H-imidazole as starting materials, the title compounds were prepared as white solid.

Compound #18:
¹H NMR: (CDCl₃) δ 7.70 (m, 2H), 7.52 (s, 1H), 7.49 (m, 1H), 7.35 (m, 2H), 7.10 (s, 1H), 6.95 (m, 1H), 6.65 (s, 1H), 5.28 (d, J=3.6 Hz, 1H), 4.30 (m, 1H), 2.75 (m, 1H), 1.60 (s, 3H), 1.35 (s, 3H)
MS (m/z): MH⁺ 380.

Compound #63:
¹H NMR: (CDCl₃) δ 7.90 (s, 1H), 7.65 (m, 2H), 7.60 (s, 1H), 7.40 (m, 1H), 7.25 (m, 2H), 7.10 (s, 1H), 6.90 (m, 1H), 5.75 (s, 1H), 1.50 (s, 6H)
MS (m/z): MH⁺ 380.

Example 17

4-[6-(4-Chloro-phenyl)-pyridazin-3-yloxy]-3-hydroxy-2,2-dimethyl-chroman-6-carbonitrile (Compound #56)

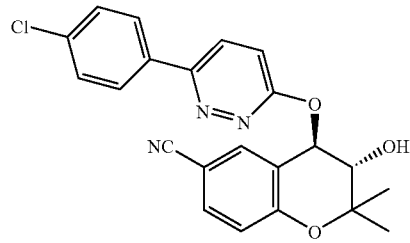

and 4-[3-(4-Chloro-phenyl)-6-oxo-6H-pyridazin-1-yl]-3-hydroxy-2,2-dimethyl-chroman-6-carbonitrile (Compound #14)

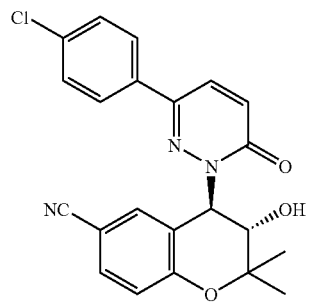

and 4-[3-(4-Chloro-phenyl)-6-oxo-6H-pyridazin-1-yl]-2,2-dimethyl-2H-chromene-6-carbonitrile (Compound #57)

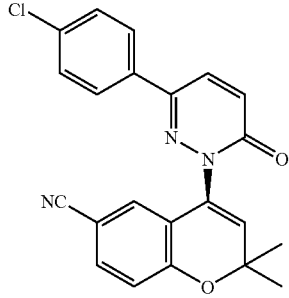

Following the procedure in Example 1, using (±)-2,2-dimethyl-1a,7b-dihydro-2H-1,3-dioxa-cyclopropa[a]naphthalene-6-carbonitrile and 6-(4-Chloro-phenyl)-2H-pyridazin-3-one as starting materials, the title compound were prepared as white solids.

Compound #56:
$^1$H NMR: (CDCl$_3$) δ 7.80 (d, J=5.6 Hz, 2H), 7.65 (d, J=2.0 Hz, 1H), 7.50 (d, J=5.6 Hz, 2H), 7.45 (d, J=7.0 Hz, 1H), 6.95 (d, J=7.0 Hz, 1H), 6.10 (d, J=3.0 Hz, 1H), 5.92 (d, J=3.0 Hz, 1H), 5.60 (d, J=7.5 z, 1H), 5.30 (br, s, 1H), 4.05 (d, J=7.5 Hz, 1H), 1.60 (s, 3H), 1.38 (s, 3H)
MS (m/z): MH$^+$ 409.

Compound #14:
$^1$H NMR: (CDCl$_3$) δ 7.72 (d, J=7.5 Hz, 1H), 7.53 (d, J=7.8 Hz, 1H), 7.45 (dd, J=7.8, 2.1 Hz, 1H), 7.40 (d, J=7.5 Hz, 1H), 7.18 (d, J=7.8 Hz, 1H), 7.10 (s, 1H), 6.98 (d, J=8.1 Hz, 1H), 6.32 (d, J=6.5 Hz, 1H), 4.35 (d, J=5.8 Hz, 1H), 2.98 (s, 1H), 1.61 (s, 3H), 1.45 (s, 3H)
MS (m/z): MH$^+$ 409.

Compound #57:
$^1$H NMR: (CDCl$_3$) δ 7.78 (d, J=7.5 Hz, 1H), 7.75 (d, J=8.0 Hz, 2H), 7.42 (d, J=8.0 Hz, 3H), 7.18 (d, J=7.5 Hz, 1H), 7.02 (s, 1H), 6.90 (d, J=7.0 Hz, 1H), 5.95 (s, 1H), 1.60 (s, 6H)
MS (m/z): MH$^+$ 391.

Example 18

3-Hydroxy-2,2-dimethyl-4-(6-phenyl-pyridazin-3-yloxy)-chroman-6-carbonitrile (Compound #52)

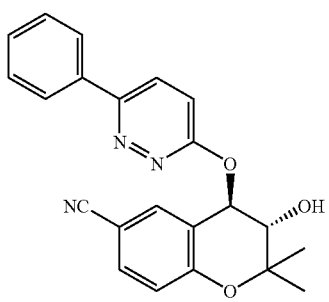

and 2,2-Dimethyl-4-(6-phenyl-pyridazin-3-yloxy)-2H-chromene-6-carbonitrile (Compound #53)

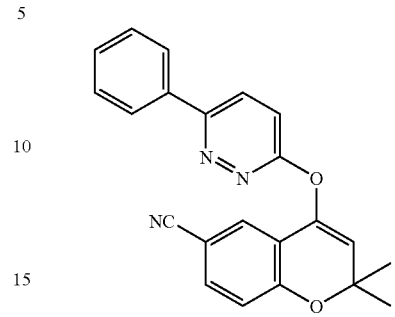

Following the procedure in Example 1, using (±)-2,2-dimethyl-1a,7b-dihydro-2H-1,3-dioxa-cyclopropa[a]naphthalene-6-carbonitrile and 6-phenyl-2H-pyridazin-3-one as starting materials, the title compounds were prepared as white solids.

Compound #52:
$^1$H NMR: (CDCl$_3$) δ 7.72 (d, J=9.5 Hz, 1H), 7.60 (m, 1H), 7.15 (d, J=7.8 Hz, 1H), 7.10 (s, 1H), 6.92 (d, J=9.5 Hz, 1H), 6.31 (d, J=6.5 Hz, 1H), 4.46 (m, 1H), 3.62 (d, J=5.8 Hz, 1H), 1.62 (s, 3H), 1.45 (s, 3H)
MS (m/z): MH$^+$ 374.

Compound #53:
$^1$H NMR: (CDCl$_3$) δ 7.75 (d, J=8.5 Hz, 1H), 7.70 (m, 1H), 7.52 (m 4H), 7.15 (d, J=8.5 Hz, 1H), 7.38 (m, 1H), 7.05 (s, 1H), 6.92 (d, J=7.5 Hz, 1H), 5.99 (s, 1H), 1.65 (s, 9H)
MS (m/z): MH$^+$ 356.

Example 19

4-[2-(4-Chloro-phenyl)-5-oxo-2,5-dihydro-pyrazol-1-yl]-3-hydroxy-2,2-dimethyl-chroman-6-carbonitrile (Compound #15)

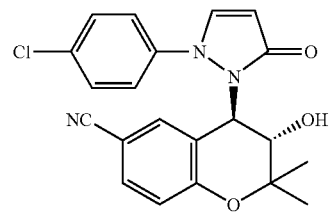

and 4-[1-(4-Chloro-phenyl)-1H-pyrazol-3-yloxy]-3-hydroxy-2,2-dimethyl-chroman-6-carbonitrile (Compound #55)

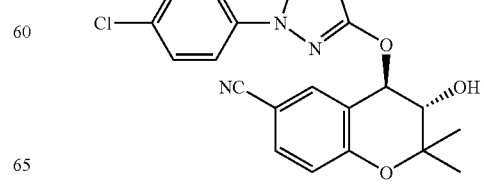

Following the procedure in Example 1, using (±)-2,2-dimethyl-1a,7b-dihydro-2H-1,3-dioxa-cyclopropa[a]naphthalene-6-carbonitrile and 1-(4-chloro-phenyl)-1,2-dihydropyrazol-3-one as starting materials, the title compounds were prepared as white solids.

Compound #15:
$^1$H NMR: (CDCl$_3$) δ 7.72 (d, J=7.5 Hz, 1H), 7.55 (d, J=8.0 Hz, 2H), 7.50 (d, J=7.5 Hz, 1H), 7.38 (d, J=8.0 Hz, 2H), 7.15 (d, J=8.5 Hz, 1H), 7.08 (s, 1H), 6.95 (d, J=8.5 Hz, 1H), 6.31 (d, J=5.5 Hz), 4.35 (d, J=5.5 Hz, 1H), 1.58 (s, 3H), 1.40 (s, 3H)

MS (m/z): MH$^+$ 397.

Compound #55:
$^1$H NMR: (CDCl$_3$) δ 7.95 (s, 1H), 7.75 (d, J=2.11 Hz, 1H), 7.66 (d, J=7.8 Hz, 1H), 7.48 (d, J=10.5 Hz, 2H), 7.42 (d, J=10.5 Hz, 2H), 6.90 (d, J=8.2 Hz, 1H), 6.18 (d, J=2.5 Hz, 1H), 5.62 (d, J=8.2 Hz, 1H), 4.05 (d, J=8.2 Hz, 2H), 1.62 (s, 3H), 1.40 (s, 3H)

MS (m/z): MH$^+$ 397.

Example 20

3-Hydroxy-2,2-dimethyl-4-[4-(4-nitro-phenyl)-piperazin-1-yl]-chroman-6-carbonitrile (Compound #51)

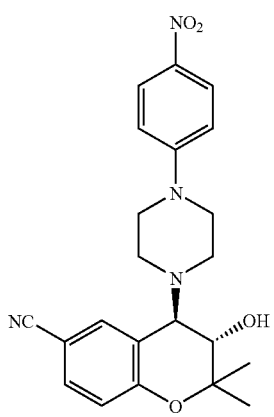

Following the procedure in Example 1, using (±)-2,2-dimethyl-1a,7b-dihydro-2H-1,3-dioxa-cyclopropa[a]naphthalene-6-carbonitrile and 1-(4-nitro-phenyl)-piperazine as starting material, the title compound was prepared as a white solid.

$^1$H NMR: (CDCl$_3$) δ 8.15 (d, J=8.5 Hz, 2H), 7.91 (s, 1H), 7.45 (d, J=7.5 Hz, 1H), 6.85 (d, J=7.5 Hz, 1H), 6.80 (d, J=8.5 Hz, 2H), 3.82 (m, 2H), 3.45 (m, 4H), 2.98 (m, 4H), 1.55 (s, 3H), 1.25 (s, 3H)

MS (m/z): MH$^+$ 409.

Example 21

4-[4-(4-Fluoro-phenyl)-piperazin-1-yl]-3-hydroxy-2,2-dimethyl-chroman-6-carbonitrile (Compound #48)

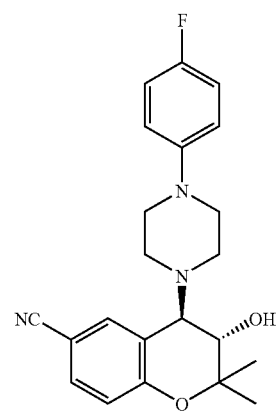

Following the procedure in Example 1, using (±)-2,2-dimethyl-1a,7b-dihydro-2H-1,3-dioxa-cyclopropa[a]naphthalene-6-carbonitrile and 1-(4-fluoro-phenyl)-piperazine as starting material, the title compound was prepared as a white solid.

$^1$H NMR: (CDCl$_3$) δ 7.88 (s, 1H), 7.45 (d, J=7.5 Hz, 1H), 6.90 (m, 5H), 3.75 (q, J=6.5 Hz, 2H), 3.20 (m, 4H), 3.01 (m, 4H), 1.55 (s, 3H), 1.25 (s, 3H)

MS (m/z): MH$^+$ 382.

Example 22

4-[4-(4-Chloro-phenyl)-piperazin-1-yl]-3-hydroxy-2,2-dimethyl-chroman-6-carbonitrile (Compound #50)

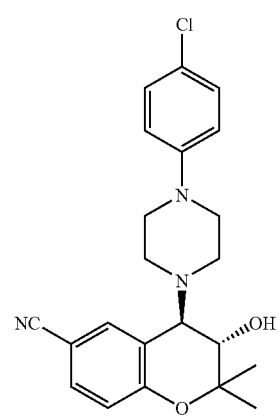

Following the procedure in Example 1, using (±)-2,2-dimethyl-1a,7b-dihydro-2H-1,3-dioxa-cyclopropa[a]naphthalene-6-carbonitrile and 1-(4-chloro-phenyl)-piperazine as starting material, the title compound was prepared as a white solid.

$^1$H NMR: (CDCl$_3$) δ 7.88 (s, 1H), 7.45 (d, J=7.6 Hz, 1H), 7.25 (d, J=8.5 Hz, 2H), 6.85 (m, 3H), 3.75 (q, J=8.0 Hz, 2H), 3.15 (m, 4H), 3.01 (m, 4H), 1.55 (s, 3H), 1.25 (s, 3H)

MS (m/z): MH$^+$ 399.

Example 23

3S-Hydroxy-2,2-dimethyl-4R-(3-oxo-2-aza-spiro[4.5]dec-2-yl)-chroman-6-carbonitrile (Compound #34)

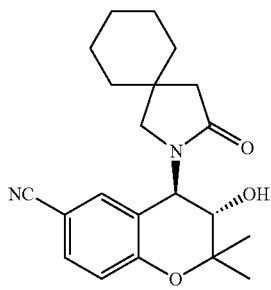

Following the procedure described in the Example 1, using (S,S)-2,2-dimethyl-1a,7b-dihydro-2H-1,3-dioxa-cyclopropa[a]naphthalene-6-carbonitrile and 2-aza-spiro[4.5]decan-3-one as starting materials, the title compound was prepared as a white solid.

$^1$H NMR: (CDCl$_3$) δ 7.45 (d, J=4.5 Hz, 1H), 7.25 (s, 1H), 6.85 (d, J=4.5 Hz, 1H), 5.70 (d, J=4.5 Hz, 1H), 4.35 (d, J=4.5 Hz, 1H), 3.70 (m, 1H), 2.95 (dd, J=90 Hz, 5.0 Hz, 2H), 2.40 (dd, J=35 Hz, 15.0 Hz, 1H), 1.50 (s, 3H), 1.40 (m, 10H), 1.20 (s, 3H)

MS (m/z): MH$^+$ 355

Example 24

4-(5-Fluoro-benzothiazol-2-ylamino)-3-hydroxy-2,2-dimethyl-chroman-6-carbonitrile (Compound #5)

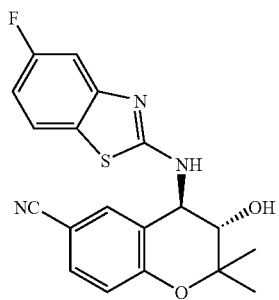

Following the procedure in Example 1, using (±)-2,2-dimethyl-1a,7b-dihydro-2H-1,3-dioxa-cyclopropa[a]naphthalene-6-carbonitrile and 5-fluoro-benzothiazol-2-ylamine as starting material, the title compound was prepared as a white solid.

$^1$H NMR: (CDCl$_3$) δ 7.70 (s, 1H), 7.45-7.40 (m, 2H), 7.25 (m, 1H), 7.00 (m, 1H), 6.90 (m, 1H), 5.95 (br, 1H), 5.05 (d, J=5.1 Hz, 1H), 3.80 (d, J=5.1 Hz, 1H), 1.50 (s, 3H), 1.32 (s, 3H)

MS (m/z): MH$^+$ 370

Example 25

3-Hydroxy-2,2-dimethyl-4-(5-nitro-benzothiazol-2-ylamino)-chroman-6-carbonitrile (Compound #6)

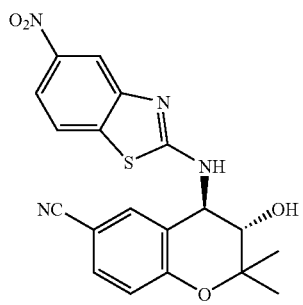

Following the procedure in Example 1, using (±)-2,2-dimethyl-1a,7b-dihydro-2H-1,3-dioxa-cyclopropa[a]naphthalene-6-carbonitrile and 5-nitro-benzothiazol-2-ylamine as starting material, the title compound was prepared as white solid.

$^1$H NMR: (CDCl$_3$) δ 8.42 (s, 1H), 8.20 (m, 1H), 7.70 (s, 1H), 7.50 (m, 2H), 6.90 (m, 1H), 5.15 (m, 1H), 3.80 (m, 1H), 1.55 (s, 3H), 1.35 (s, 3H)

MS (m/z): MH$^+$ 397

Example 26

4-(5-Ethoxy-benzothiazol-2-ylamino)-3-hydroxy-2,2-dimethyl-chroman-6-carbonitrile (Compound #4)

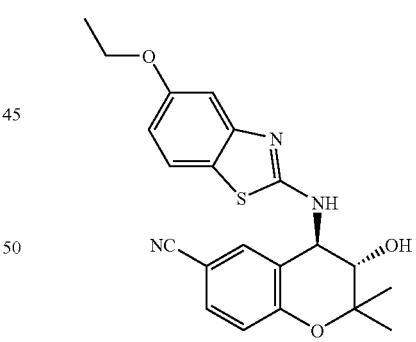

Following the procedure in Example 1, using (±)-2,2-dimethyl-1a,7b-dihydro-2H-1,3-dioxa-cyclopropa[a]naphthalene-6-carbonitrile and 5-ethoxy-benzothiazol-2-ylamine as starting material, the title compound was prepared as a white solid.

$^1$H NMR: (CDCl$_3$) δ 7.70 (s, 1H), 7.50-7.40 (m, 2H), 7.10 (s, 1H), 6.90 (m, 2H), 5.05 (m, 1H), 4.10 (m, 2H), 3.80 (m, 1H), 1.55 (s, 3H), 1.40 (m, 3H), 1.30 (s, 3H)

MS (m/z): MH$^+$ 396

Example 27

4R-(5-Chloro-6-fluoro-1H-benzoimidazole-2-sulfonyl)-3S-hydroxy-2,2-dimethyl-chroman-6-carbonitrile (Compound #72)

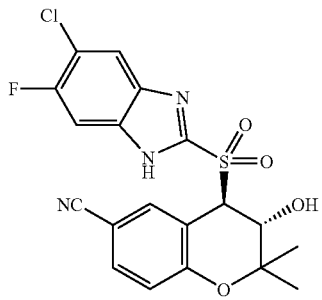

Following the procedure in Example 1, using (S,S)-2,2-dimethyl-1a,7b-dihydro-2H-1,3-dioxa-cyclopropa[a]naphthalene-6-carbonitrile and 5-chloro-6-fluoro-1H-benzoimidazole-2-thiol as starting material, the title compound was prepared as a white solid.

$^1$H NMR: (CDCl$_3$) δ 10.40 (br, 1H), 8.00 (s, 1H), 7.50-7.40 (m, 3H), 6.90 (m, 1H), 4.80 (m, 1H), 4.10 (m, 1H), 1.60 (s, 6H)

MS (m/z): MH$^+$ 396

Example 28

(3S,4R)-4-(5-Chloro-1H-benzoimidazol-2-ylsulfanyl)-3-hydroxy-2,2-dimethyl-chroman-6-carbonitrile (Compound #29)

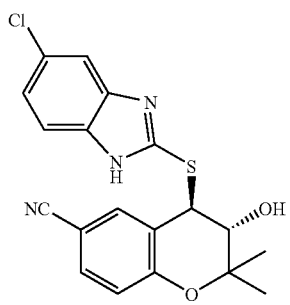

Following the procedure in Example 1, using (S,S)-2,2-dimethyl-1a,7b-dihydro-2H-1,3-dioxa-cyclopropa[a]naphthalene-6-carbonitrile and 5-chloro-1H-benzoimidazole-2-thiol as starting material, the title compound was prepared as a white solid.

$^1$H NMR: (CDCl$_3$) δ 10.50 (br, 1H), 8.00 (s, 1H), 7.50-7.40 (m, 4H), 7.20 (m, 1H), 6.90 (m, 1H), 4.78 (m, 1H), 4.10 (m, 1H), 1.60 (s, 6H)

MS (m/z): MH$^+$ 396

Example 29

4R-[5-(4-Chloro-phenyl)-pyrazol-1-yl]-3S-hydroxy-2,2-dimethyl-chroman-6-carbonitrile (Compound #10)

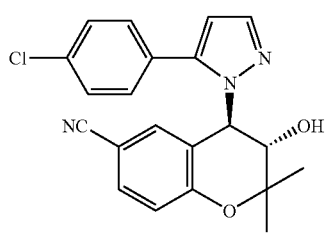

Following the procedure in Example 1, using (3S,4R)-2,2-dimethyl-1a,7b-dihydro-2H-1,3-dioxa-cyclopropa[a]naphthalene-6-carbonitrile and 5-(4-chloro-phenyl)-1H-pyrazole as starting material, the title compound was prepared as a pale yellow solid.

$^1$H NMR (CDCl$_3$) δ 8.00 (s, 1H), 7.70 (m, 2H), 7.55 (m, 1H), 7.50 (s, 1H), 7.30 (m, 2H), 7.10 (s, 1H), 7.00 (m, 1H), 5.30 (m, 1H), 4.00 (m, 1H), 1.50 (s, 3H), 1.30 (s, 3H)

MS (m/z): MH$^+$ 380

Example 30

4-(5-Chloro-benzothiazol-2-ylamino)-3-hydroxy-2,2-dimethyl-chroman-6-carbonitrile (Compound #1)

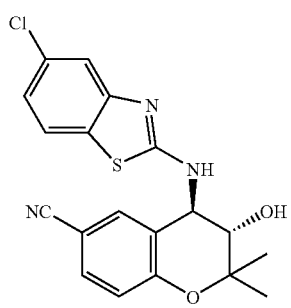

Following the procedure in Example 1, using (±)-2,2-dimethyl-1a,7b-dihydro-2H-1,3-dioxa-cyclopropa[a]naphthalene-6-carbonitrile and 5-chloro-benzothiazol-2-ylamine as starting material, the title compound was prepared as a white solid.

$^1$H NMR: (CDCl$_3$) δ 7.70 (s, 1H), 7.55-7.40 (m, 3H), 7.25 (m, 1H), 6.90 (m, 1H), 5.75 (br, 1H), 5.10 (m, 1H), 3.85 (m, 1H), 1.55 (s, 3H), 1.35 (s, 3H)

MS (m/z): MH$^+$ 386.

Example 31

4-(5-Chloro-benzooxazole-2-sulfonyl)-3-hydroxy-2,2-dimethyl-chroman-6-carbonitrile (Compound #17)

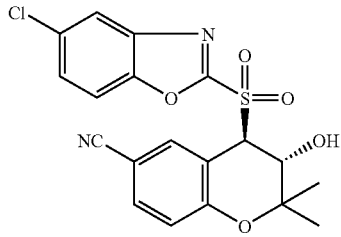

Following the procedure in Example 1, using (±)-2,2-dimethyl-1a,7b-dihydro-2H-1,3-dioxa-cyclopropa[a]naphthalene-6-carbonitrile and 5-chloro-benzooxazole-2-thiol as starting material, the title compound was prepared as a white solid.

$^1$H NMR: (CDCl$_3$) δ 7.91 (s, 1H), 7.48 (m, 1H), 7.11 (m, 3H), 6.90 (d, J=7.5 Hz, 1H), 4.15 (d, J=8.0 Hz, 1H), 3.71 (d, J=8.0 Hz, 1H), 1.52 (s, 3H), 1.40 (s, 3H)

MS (m/z): MH$^+$ 420.

Example 32

4-(5-Difluoromethoxy-1H-benzoimidazol-2-ylsulfanyl)-3-hydroxy-2,2-dimethyl-chroman-6-carbonitrile (Compound #16)

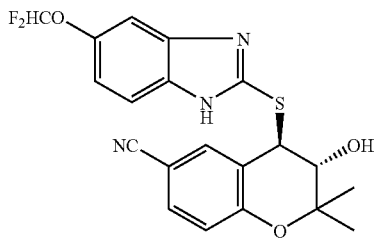

Following the procedure in Example 1, using (±)-2,2-dimethyl-1a,7b-dihydro-2H-1,3-dioxa-cyclopropa[a]naphthalene-6-carbonitrile and 5-difluoromethoxy-1H-benzoimidazole-2-thiol as starting material, the title compound was prepared as a white solid.

$^1$H NMR: (CDCl$_3$) δ 11.1 (br, s, 1H), 8.01 (s, 1H), 7.48 (d, J=7.5 Hz, 1H), 7.40 (br, s, 2H), 7.05 (d, J=7.5 Hz, 1H), 6.91 (d, J=8.1 Hz, 1H), 6.50 (s, 1H), 4.78 (d, J=8.5 Hz, 1H), 4.15 (d, J=8.5 Hz, 1H), 1.61 (s, 3H), 1.35 (s, 3H)

MS (m/z): MH$^+$ 418.

Example 33

4-(5-Chloro-benzooxazol-2-ylamino)-3-hydroxy-2,2-dimethyl-chroman-6-carbonitrile (Compound #2)

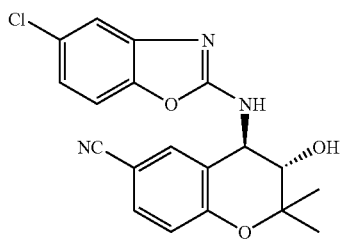

Following the procedure in Example 1, using (±)-2,2-dimethyl-1a,7b-dihydro-2H-1,3-dioxa-cyclopropa[a]naphthalene-6-carbonitrile and 5-chloro-benzooxazol-2-ylamine as starting material, the title compound was prepared as a white solid.

$^1$H NMR: (CDCl$_3$) δ 7.65 (s, 1H), 7.48 (d, J=7.5 Hz, 1H), 7.12 (d, J=8.0 Hz, 2H), 7.05 (d, J=6.5 Hz, 1H), 6.92 (d, =7.5 Hz, 1H), 6.42 (s, 1H), 5.05 (d, J=7.1 Hz, 1H), 3.82 (d, J=7.1 Hz, 1H), 1.55 (s, 3H), 1.35 (s, 3H)

MS (m/z): MH$^+$ 372.

Example 34

(3S,4R)-3-Hydroxy-2,2-dimethyl-4-(quinazolin-4-yloxy)-chroman-6-carbonitrile (Compound #40)

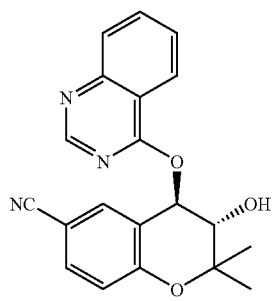

Following the procedure in Example 1, using (S,S)-2,2-dimethyl-1a,7b-dihydro-2H-1,3-dioxa-cyclopropa[a]naphthalene-6-carbonitrile and quinazolin-4-ol as starting material, the title compound was prepared as a white solid.

$^1$H NMR: (CDCl$_3$) δ 8.38 (d, J=8.5 Hz, 1H), 7.98~7.45 (m, 4H), 7.15 (s, 1H), 7.02 (d, J=7.5 Hz, 1H), 6.30 (d, J=7.8 Hz, 1H), 4.05 (m, 1H), 3.48 (d, J=6.5 Hz, 1H), 1.65 (s, 3H), 1.45 (s, 3H)

MS (m/z): MH$^+$ 348.

Example 35

4R-(3,4-Dihydro-isoquinolin-1-ylsulfanyl)-3S-hydroxy-2,2-dimethyl-chroman-6-carbonitrile (Compound #42)

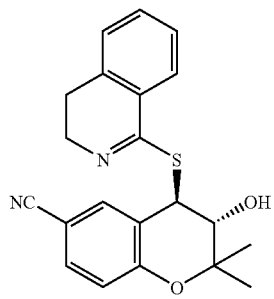

Following the procedure in Example 1, using (S,S)-2,2-dimethyl-1a,7b-dihydro-2H-1,3-dioxa-cyclopropa[a]naphthalene-6-carbonitrile and 3,4-dihydro-2H-isoquinoline-1-thione as starting material, the title compound was prepared as a white solid.

¹H NMR: (CDCl₃) δ 8.12 (d, J=7.8 Hz, 1H), 7.52~7.15 (m, 6H), 3.95 (m, 1H), 3.72 (m, 1H), 3.55 (m, 1H), 3.35 (m, 1H), 3.10 (d, J=7.5 Hz, 1H), 3.05 (m, 1H), 1.60 (s, 3H), 1.55 (s, 3H)

MS (m/z): MH⁺ 365.

Example 36

3S-Hydroxy-2,2-dimethyl-4R-(4-trifluoromethyl-pyrimidin-2-ylsulfanyl)-chroman-6-carbonitrile (Compound #43)

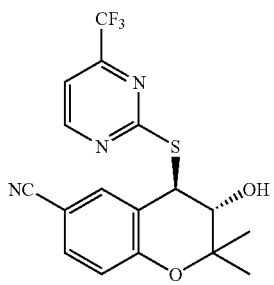

Following the procedure in Example 1, using (S,S)-2,2-dimethyl-1a,7b-dihydro-2H-1,3-dioxa-cyclopropa[a]naphthalene-6-carbonitrile and 4-trifluoromethyl-pyrimidine-2-thiol as starting material, the title compound was prepared as a white solid.

¹H NMR: (CDCl₃) δ 8.42 (s, 1H), 8.22 (d, J=7.5 Hz, 1H), 8.05 (s, 1H), 7.52 (m, 1H), 7.32 (d, J=8.5 Hz, 1H), 4.10 (d, J=7.8 Hz, 1H), 3.75 (m, 1H), 1.55 (s, 3H), 1.32 9s, 3H)

MS (m/z): MH⁺ 382.

Example 37

4-(Benzo[d]isothiazol-3-yloxy)-3-hydroxy-2,2-dimethyl-chroman-6-carbonitrile (Compound #20)

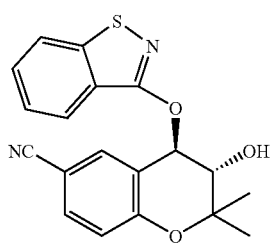

Following the procedure in Example 1, using (±)-2,2-dimethyl-1a,7b-dihydro-2H-1,3-dioxa-cyclopropa[a]naphthalene-6-carbonitrile and benzo[d]isothiazol-3-one as starting material, the title compound was prepared as a white solid.

¹H NMR: (CDCl₃) δ 7.98 (d, J=8.1 Hz, 1H), 7.82 (d, J=8.0 Hz, 1H), 7.72 (s, 1H), 7.61 (t, J=7.5 Hz, 1H), 7.53 (d, J=8.1 Hz, 1H), 7.45 (t, J=7.5 Hz, 1H), 6.98 (d, J=8.5 Hz, 1H), 6.12 (d, J=7.5 Hz, 1H), 4.82 (d, J=2.1 Hz, 1H0, 4.12 (d, J=7.5 Hz, 1H), 1.59 (s, 3H), 1.46 s, 3H)

MS (m/z): MH⁺ 353.

Example 38

4-(6-Chloro-benzo[d]isoxazole-3-sulfonyl)-3-hydroxy-2,2-dimethyl-chroman-6-carbonitrile (Compound #19)

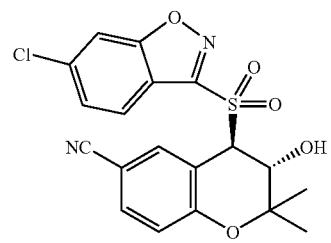

Following the procedure in Example 1, using (±)-2,2-dimethyl-1a,7b-dihydro-2H-1,3-dioxa-cyclopropa[a]naphthalene-6-carbonitrile and 6-chloro-benzo[d]isoxazole-3-thione as starting material, the title compound was prepared as a white solid.

¹H NMR: (CDCl₃) δ 8.10 (s, 1H), 7.90 (s, 1H), 7.70-7.50 (m, 2H), 6.95 (m, 1H), 5.80 (m, 1H), 4.05 (m, 1H), 3.68 (m, 1H), 1.55 (s, 3H), 1.20 (s, 3H)

MS (m/z): MH⁺ 420.

Example 39

(3S,4R)-4-(Benzo[d]isoxazol-3-yloxy)-3-hydroxy-2,2-dimethyl-chroman-6-carbonitrile (Compound #23)

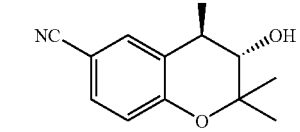

Following the procedure in Example 1, using (S,S)-2,2-dimethyl-1a,7b-dihydro-2H-1,3-dioxa-cyclopropa[a]naphthalene-6-carbonitrile and benzo[d]isoxazol-3-one as starting materials, the title compound was prepared as a white solid.

¹H NMR: (CDCl₃) δ 7.71 (s, 1H), 7.65-7.48 (m, 4H), 7.30 (m, 1H), 6.95 (d, J=5.1 Hz, 1H), 5.90 (d, J=5.1 Hz, 1H), 4.25 (m, 1H), 3.80 (d, J=2.0 Hz, 1H), 1.55 (s, 3H), 1.40 (s, 3H)

MS (m/z): MH⁺ 337

Example 40

(3S,4R)-4-(5-Fluoro-benzo[d]isoxazol-3-yloxy)-3-hydroxy-2,2-dimethyl-chroman-6-carbonitrile (Compound #70)

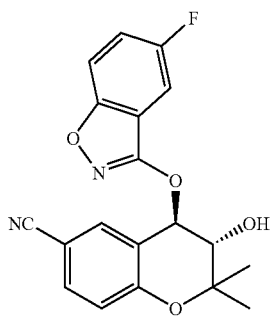

Following the procedure in Example 1, using (S,S)-2,2-dimethyl-1a,7b-dihydro-2H-1,3-dioxa-cyclopropa[a]naphthalene-6-carbonitrile and 5-fluoro-benzo[d]isoxazol-3-one as starting materials, the title compound was prepared as a white solid.

$^1$H NMR: (CDCl$_3$) δ 7.75 (s, 1H), 7.50-7.40 (m, 2H), 7.20 (m, 2H), 6.95 (m, 2H), 6.10 (br, 1H), 5.10 (m, 2H), 3.95 (m, 1H), 1.50 (s, 3H), 1.30 (s, 3H)

MS (m/z): MH$^+$ 379.

Example 41

(3S,4R)-4-(6-Chloro-benzo[d]isoxazol-3-ylamino)-3-hydroxy-2,2-dimethyl-chroman-6-carbonitrile (Compound #67)

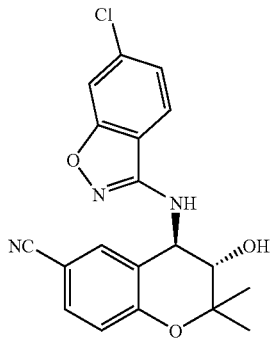

Following the procedure in Example 1, using (S,S)-2,2-dimethyl-1a,7b-dihydro-2H-1,3-dioxa-cyclopropa[a]naphthalene-6-carbonitrile and 6-chloro-benzo[d]isoxazol-3-ylamine (prepared by literature known method) as starting materials, the title compound was prepared as a white solid.

$^1$H NMR: (DMSO) δ 8.00 (s, 1H), 7.70 (s, 1H), 7.60-7.50 (m, 3H), 6.95 (m, 1H), 5.80 (m, 1H), 4.65 (m, 1H), 3.88 (m, 1H), 1.45 (s, 3H), 1.20 (s, 3H)

MS (m/z): MH$^+$ 370

Example 42

(3S,4R)-4-(5-Chloro-benzo[d]isoxazol-3-yloxy)-3-hydroxy-2,2-dimethyl-chroman-6-carbonitrile (Compound #38)

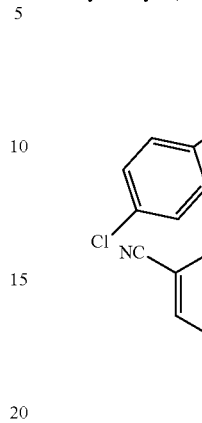

Following the procedure in Example 1, using (S,S)-2,2-dimethyl-1a,7b-dihydro-2H-1,3-dioxa-cyclopropa[a]naphthalene-6-carbonitrile and 5-chloro-benzo[d]isoxazol-3-one (prepared by literature known method) as starting materials, the title compound was prepared as a white solid.

$^1$H NMR: (CDCl$_3$) δ 7.65 (m, 1H), 7.55 (m, 1H), 7.35 (s, 1H), 7.20 (m, 2H), 6.95 (m, 1H), 5.62 (m, 1H), 4.40 (m, 1H), 4.20 (m, 1H), 1.60 (s, 3H), 1.35 (s, 3H)

MS (m/z): MNa$^+$ 393

Example 43

3S-Hydroxy-2,2-dimethyl-4R-(7-methyl-3-oxo-3H-benzo[d]isoxazol-2-yl)-chroman-6-carbonitrile (Compound #32)

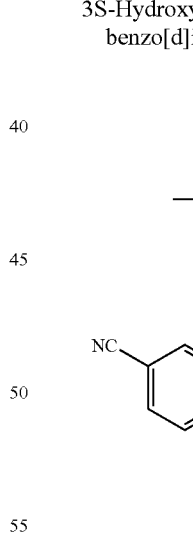

Following the procedure in Example 1, using (S,S)-2,2-dimethyl-1a,7b-dihydro-2H-1,3-dioxa-cyclopropa[a]naphthalene-6-carbonitrile and 7-methyl-benzo[d]isoxazol-3-one (prepared by literature known method) as starting materials, the title compound was prepared as a white solid.

$^1$H NMR: (CDCl$_3$) δ 7.75 (m, 1H), 7.55-7.45 (m 2H), 7.40 (d, J=4.4 Hz, 1H), 7.20 (d, J=4.4 Hz, 1H), 6.95 (d, J=5.0 Hz, 1H), 5.90 (d, J=5.0 Hz, 1H), 4.15 (m, 1H), 3.75 (m, 1H), 2.50 (s, 3H), 1.50 (s, 3H), 1.40 (s, 3H)

MS (m/z): MH$^+$ 351

Example 44

2-(6-Chloro-3-hydroxy-2,2-dimethyl-chroman-4R-yl)-benzo[d]isothiazol-3S-one (Compound #30)

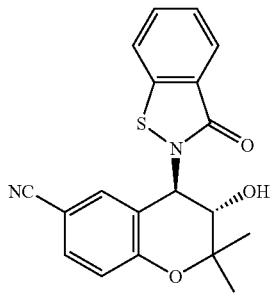

Following the procedure in Example 1, using (S,S)-2,2-dimethyl-1a,7b-dihydro-2H-1,3-dioxa-cyclopropa[a]naphthalene-6-carbonitrile and benzo[d]isothiazol-3-one as starting materials, the title compound was prepared white solid.

$^1$H NMR: (CDCl$_3$) δ 7.90 (m, 1H), 7.80 (m, 1H), 7.70 (s, 1H), 7.60-7.40 (m, 3H), 6.95 (m, 1H), 6.10 (m, 1H), 4.80 (m, 1H), 4.10 (m, 1H), 1.55 (s, 3H), 1.40 (s, 3H)

MS (m/z): MH$^+$ 351

Example 45

4R-(6-Chloro-benzo[d]isoxazol-3-yloxy)-3S-hydroxy-2,2-dimethyl-chroman-6-carbonitrile (Compound #22)

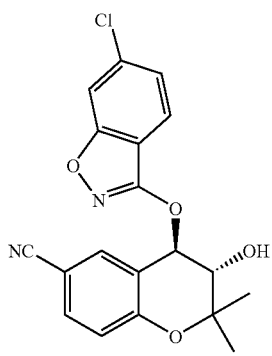

and 4R-(6-Chloro-3-oxo-3H-benzo[d]isoxazol-2-yl)-3S-hydroxy-2,2-dimethyl-chroman-6-carbonitrile (Compound #117)

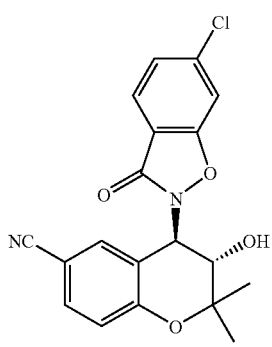

Following the procedure in Example 1, using (S,S)-2,2-dimethyl-1a,7b-dihydro-2H-1,3-dioxa-cyclopropa[a]naphthalene-6-carbonitrile and 6-chloro-benzo[d]isoxazol-3-one (prepared by literature known method) as starting materials, the title compounds were prepared as white solids.

Compound #33:
$^1$H NMR: (CDCl$_3$) δ 7.70 (s, 1H), 7.60-7.50 (m, 2H), 7.35-7.30 (m, 2H), 6.95 (d, J=8.2 Hz, 1H), 5.90 (d, J=6.0 Hz, 1H), 4.15 (m, 1H), 3.60 (d, J=2.0 Hz, 1H), 1.55 (s, 3H), 1.40 (s, 3H)

MS (m/z): MH$^+$ 371.

Compound #117:
$^1$H NMR: (CDCl$_3$) δ 7.70 (d, J=8.5 Hz, 1H), 7.50 (d, J=8.5 Hz, 2H), 7.30-7.25 (m, 3H), 6.95 (d, J=8.2 Hz, 1H), 5.62 (d, J=8.5 Hz, 1H), 4.20 (d, J=8.5 Hz, 1H), 3.20 (br, 1H), 1.55 (s, 3H), 1.35 (s, 3H)

MS (m/z): MH$^+$ 371.

Example 46

(3S,4R)-4-(5-Chloro-benzo[d]isoxazol-3-ylamino)-3-hydroxy-2,2-dimethyl-chroman-6-carbonitrile (Compound #39)

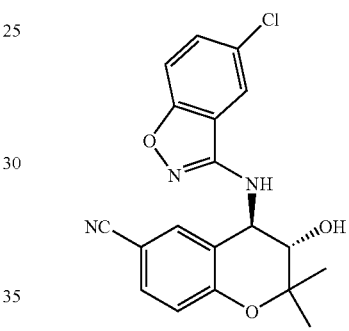

Following the procedure in Example 1, using (S,S)-2,2-dimethyl-1a,7b-dihydro-2H-1,3-dioxa-cyclopropa[a]naphthalene-6-carbonitrile and 5-chloro-benzo[d]isoxazol-3-ylamine as starting materials, the title compound was prepared as a white solid.

$^1$H NMR: (CDCl$_3$) δ$^1$H NMR (CDCl$_3$) δ 8.00 (s, 1H), 7.65 (s, 1H), 7.55 (m, 3H), 6.95 (m, 1H), 5.70 (m, 1H), 4.60 (m, 1H), 3.85 (m, 1H), 3.80 (s, 3H), 1.45 (s, 3H), 1.20 (s, 3H)

MS (m/z): MH$^+$ 370

Example 47

(3S,4R)-3-Hydroxy-4-(5-methoxy-benzo[d]isoxazol-3-yloxy)-2,2-dimethyl-chroman-6-carbonitrile (Compound #44)

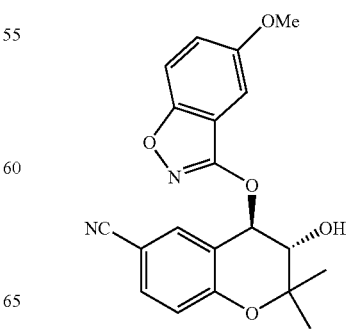

Following the procedure in Example 1, using (S,S)-2,2-dimethyl-1a,7b-dihydro-2H-1,3-dioxa-cyclopropa[a]naphthalene-6-carbonitrile and 5-methoxy-benzo[d]isoxazol-3-one as starting materials, the title compound was prepared as a white solid.

$^1$H NMR (CDCl$_3$) δ 8.20 (s, 1H), 7.50 (m, 1H), 7.00 (m, 2H), 6.90 (m, 2H), 4.90 (m, 1H), 3.85 (m, 1H), 3.80 (s, 3H), 1.55 (s, 3H), 1.25 (s, 3H)

MS (m/z): MH$^+$ 385

Example 48

3S-Hydroxy-2,2-dimethyl-4R-(6-nitro-benzo[d]isothiazol-3-yloxy)-chroman-6-carbonitrile (Compound #41)

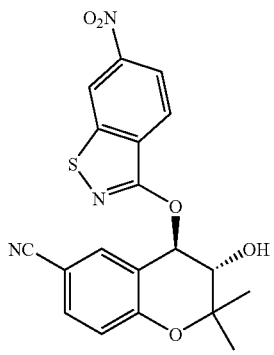

and (3S,4R)-2,2-Dimethyl-R-(6-nitro-benzo[d]isothiazol-3-yloxy)-2H-chromene-6-carbonitrile (Compound #69)

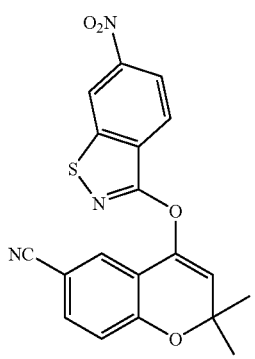

Following the procedure in Example 1, using (S,S)-2,2-dimethyl-1a,7b-dihydro-2H-1,3-dioxa-cyclopropa[a]naphthalene-6-carbonitrile and 6-nitro-benzo[d]isothiazol-3-one as starting materials, the title compounds were prepared as white solids.

Compound #41:
$^1$H NMR: (CDCl$_3$) δ 9.95 (br, s, 1H), 9.05 (s, 1H), 8.58 (d, J=8.5 Hz, 1H), 7.85 (d, J=8.0 Hz, 1H), 7.72 (d, J=8.5 hz, 1H), 7.61 (s, 1H), 7.08 (d, J=8.8 Hz, 1H), 4.56 (m, 1H), 3.02 (m, 1H), 1.65 (s, 3H), 1.45 (s, 3H)
MS (m/z): MH$^+$ 398.

Compound #69:
$^1$H NMR: (CDCl$_3$) δ 8.85 (s, 1H), 8.06 (d, J=7.5 Hz, 1H), 7.45 (d, J=7.0 Hz, 1H), 7.12 (d, J=7.5 hz, 1H), 7.00 (s, 1H), 6.21 (d, J=7.0 Hz, 1H), 5.56 (m, 1H), 1.65 (s, 3H), 1.45 (s, 3H)
MS (m/z): MH$^+$ 380.

Example 49

2,2-Dimethyl-6-phenylsulfanyl-2H-chromene

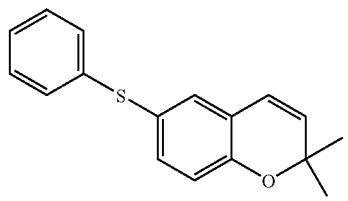

6-Bromo-2,2-dimethyl-2H-chromene (10 mmoL) in THF (20 mL) was treated with n-butyl lithium (15 mmoL) dropwise at −78° C. The resulting solution was stirred at −78° C. for 30 min. Benzene disulfide (10 mmoL) in THF (10 mL) was then added dropwise into the reaction over about 15 min. The reaction mixture was kept at −78° C. and slowly warmed to room temperature over 2 hrs. The solvent was removed and the residue was partitioned between diethyl ether and water. The combined organic layer was washed with brine, filtered, dried over anhydrous Na$_2$SO$_4$ and concentrated to yield crude material, which was purified by silica gel chromatography to yield the title compound as a white solid.

$^1$H NMR (CDCl$_3$) δ 7.95 (m, 3H), 7.80 (m, 1H), 7.50 (m, 3H), 6.85 (m, 1H), 3.95 (m, 1H), 3.55 (m, 1H), 1.55 (s, 3H), 1.25 (s, 3H)
MS (m/z): MH$^+$ 317

Example 50

(S,S)-6-Benzenesulfonyl-2,2-dimethyl-1a,7b-dihydro-2H-1,3-dioxa-cyclopropa[a]naphthalene

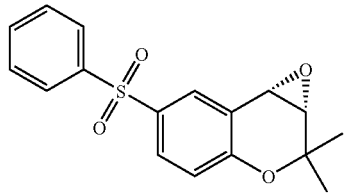

2,2-Dimethyl-6-phenylsulfanyl-2H-chromene (prepared as in Example 49) (2.0 g, 7.5 mmol) and Jacobson catalyst "S.S" in dichloromethane (5 ml) was added by bleach (pH=11-12, adjusted with NaOH/NaH$_2$PO$_4$) at 0° C. The reaction mixture was kept at 0° C. for 4 h and then quenched with saturated NH$_4$Cl. The aqueous layer was extracted with dichloromethane twice. The organic layer was combined, washed with brine, dried and concentrated to yield crude product. The crude product was purified on silica gel (Hexanes:ethyl acetate: 1:2, R$_f$=0.5) to yield the title compound as a colorless solid.

$^1$H NMR (CDCl$_3$) δ 7.95 (s, 1H), 7.90 (m, 2H), 7.80 (m, 1H), 7.50 (m, 3H), 6.85 (m, 1H), 3.90 (m, 1H), 3.50 (m, 1H), 1.55 (s, 3H), 1.25 (s, 3H).

Example 51

2-(6-Benzenesulfonyl-3S-hydroxy-2,2-dimethyl-chroman-4-yl)-6-chloro-4R-benzo[d]isoxazol-3-one (Compound 78)

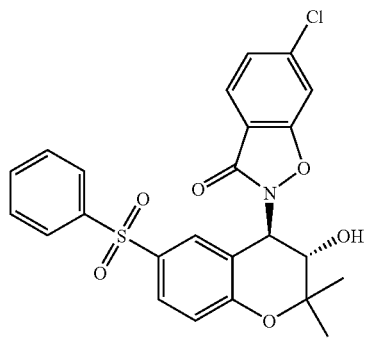

and 6-Benzenesulfonyl-4R-(6-chloro-benzo[d]isoxazol-3-yloxy)-2,2-dimethyl-chroman-3S-ol (Compound #77)

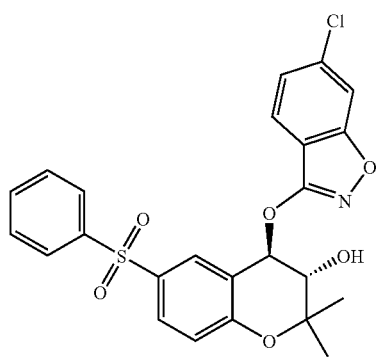

Example 52

2-(6-Benzenesulfonyl-3S-hydroxy-2,2-dimethyl-chroman-4-yl)-5-chloro-4R-benzo[d]isoxazol-3-one (Compound #76)

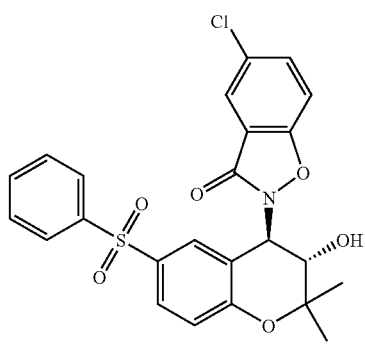

and (3S,4R)-6-Benzenesulfonyl-4R-(5-chloro-benzo[d]isoxazol-3-yloxy)-2,2-dimethyl-chroman-3S-ol (Compound #75)

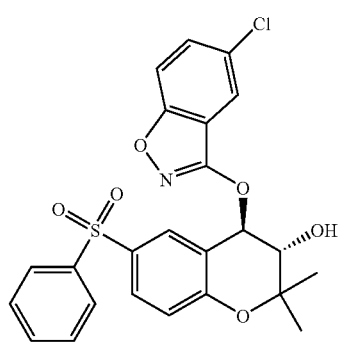

Following the procedure in Example 1, using (S,S)-6-benzenesulfonyl-2,2-dimethyl-1a,7b-dihydro-2H-1,3-dioxa-cyclopropa[a]naphthalene and 6-chloro-benzo[d]isoxazol-3-one as starting materials, the title compounds were prepared as white solids.

Compound #78:

$^1$H NMR: (CDCl$_3$) δ 7.75 (m, 3H), 7.60 (d, J=6.5 Hz, 1H), 7.55-7.35 (m, 4H), 7.20 (d, J=7.0 Hz, 1H), 7.10 (s, 1H), 6.90 (d, J=7.0 Hz, 1H), 5.60 (d, J=6.5 Hz, 1H), 4.15 (m, 1H), 4.00 (d, J=4.5 Hz, 1H), 1.55 (s, 3H), 1.30 (s, 3H)

MS (m/z): MH$^+$ 485.

Compound #77:

$^1$H NMR: (CDCl$_3$) δ 8.00 (s, 1H), 7.85 (d, J=6.5 Hz, 2H), 7.50 (d, J=6.5 Hz, 1H), 7.55-7.40 (m, 5H), 7.35 (d, J=6.0 Hz, 1H), 6.96 (d, J=6.0 Hz, 1H), 5.85 (d, J=4.5 Hz, 1H), 4.10 (m, 1H), 3.90 (m, 1H), 1.50 (s, 3H), 1.35 (s, 3H)

MS (m/z): MH$^+$ 486.

Following the procedure in Example 1, using (S,S)-6-benzenesulfonyl-2,2-dimethyl-1a,7b-dihydro-2H-1,3-dioxa-cyclopropa[a]naphthalene and 5-chloro-benzo[d]isoxazol-3-one as starting materials, the title compounds were prepared as white solids.

Compound #76:

$^1$H NMR: (CDCl$_3$) δ7.75 (m, 3H), 7.65 (s, 1H), 7.55-7.40 (m, 5H), 7.10 (d, J=6.0 Hz, 1H), 6.90 (d, J=6.0 Hz, 1H), 5.65 (d, J=6.5 Hz, 1H), 4.15 (m, 1H), 3.45 (m, 2H), 1.55 (s, 3H), 1.30 (s, 3H)

MS (m/z): MH$^+$ 485.

Compound #75:

$^1$H NMR: (CDCl$_3$) δ 7.95 (s, 1H), 7.85 (d, J=5.5 Hz, 2H), 7.80 (d, J=6.0 Hz, 1H), 7.55-7.40 (m, 6H), 6.96 (d, J=6.0 Hz, 1H), 5.85 (d, J=4.5 Hz, 1H), 4.10 (m, 1H), 3.90 (m, 1H), 1.50 (s, 3H), 1.40 (s, 3H)

MS (m/z): MH$^+$ 486.

Example 53

6-Benzenesulfonyl-4R-(5-chloro-benzo[d]isoxazol-3-ylamino)-2,2-dimethyl-chroman-3S-ol (Compound #74)

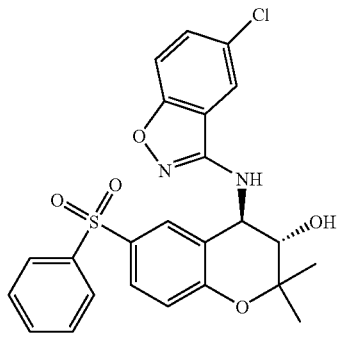

Following the procedure in Example 1, using (S,S)-6-benzenesulfonyl-2,2-dimethyl-1a,7b-dihydro-2H-1,3-dioxa-cyclopropa[a]naphthalene and 5-chloro-benzo[d]isoxazol-3-ylamine as starting materials, the title compound as prepared as a white solid.

$^1$H NMR: (CDCl$_3$) δ 7.90 (s, 1H), 7.75 (d, J=6.5 Hz, 2H), 7.60 (s, 1H), 7.55-7.30 (m, 5H), 7.20 (d, J=7.0 Hz, 1H), 6.70 (d, J=7.0 Hz, 1H), 5.70 (d, J=4.5 Hz, 1H), 4.90 (m, 1H), 4.15 (m, 1H), 3.90 (d, J=4.5 Hz, 1H), 1.45 (s, 3H), 1.25 (s, 3H)

MS (m/z): MH$^+$ 485.

Example 54

(3S,4R)-6-Benzenesulfonyl-4R-(7-chloro-benzo[d]isoxazol-3-ylamino)-2,2-dimethyl-chroman-3S-ol (Compound #87)

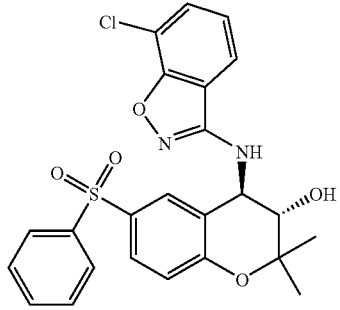

Following the procedure in Example 1, using (S,S)-6-benzenesulfonyl-2,2-dimethyl-1a,7b-dihydro-2H-1,3-dioxa-cyclopropa[a]naphthalene and 7-chloro-benzo[d]isoxazol-3-ylamine as starting materials, the title compound was prepared as a white solid.

$^1$H NMR: (CDCl$_3$) δ 7.90 (s, 1H), 7.66 (d, J=7.5 Hz, 2H), 7.55-7.45 (m, 4H), 7.40 (d, J=7.5 Hz, 2H), 7.00 (m, 1H), 6.70 (d, J=8.0 Hz, 1H), 5.70 (d, J=4.5 Hz, 1H), 4.90 (m, 1H), 3.95 (d, J=4.5 Hz, 1H), 1.50 (s, 3H), 1.25 (s, 3H)

MS (m/z): MH$^+$ 485.

Example 55

(3S,4R)-6-Benzenesulfonyl-4R-(6-chloro-benzo[d]isoxazol-3-ylamino)-2,2-dimethyl-chroman-3S-ol (Compound #73)

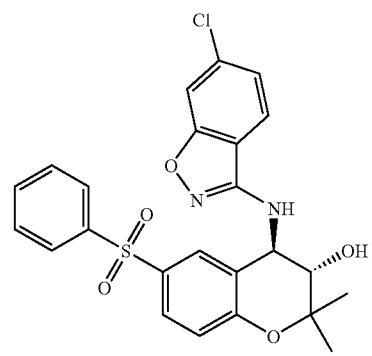

Following the procedure in Example 1, using (S,S)-6-benzenesulfonyl-2,2-dimethyl-1a,7b-dihydro-2H-1,3-dioxa-cyclopropa[a]naphthalene and 6-chloro-benzo[d]isoxazol-3-ylamine as starting materials, the title compound was prepared as a white solid.

$^1$H NMR: (CDCl$_3$) δ 7.90 (s, 1H), 7.75 (d, J=7.5 Hz, 2H), 7.60-7.40 (m, 5H), 7.30 (d, J=7.5 Hz, 1H), 7.05 (m, 1H), 6.80 (d, J=8.0 Hz, 1H), 5.70 (d, J=4.5 Hz, 1H), 4.90 (m, 1H), 3.90 (d, J=4.5 Hz, 1H), 1.50 (s, 3H), 1.25 (s, 3H)

MS (m/z): MH$^+$ 485.

Example 56

4R-(6-Chloro-benzo[d]isoxazol-3-yloxy)-2,2-dimethyl-6-(piperidine-1-sulfonyl)-chroman-3S-ol (Compound #83)

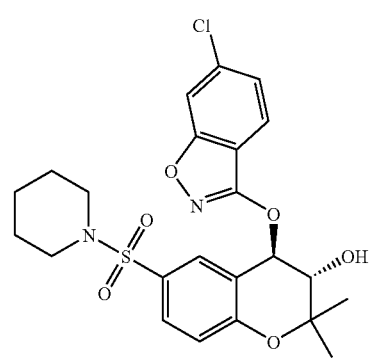

and 6-Chloro-2-[3S-hydroxy-2,2-dimethyl-6-(piperidine-1-sulfonyl)-chroman-4-yl]-R-benzo[d]isoxazol-3-one (Compound #84)

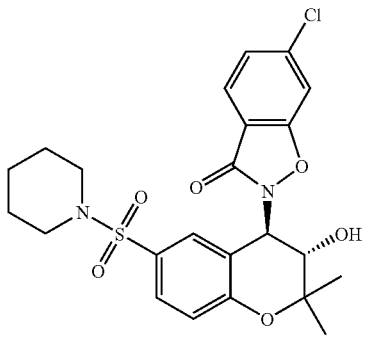

Following the procedure in Example 1, using (S,S)-6-piperidinylsulfonyl-2,2-dimethyl-1a,7b-dihydro-2H-1,3-dioxa-cyclopropa[a]naphthalene (literature known compound) and 6-chloro-benzo[d]isoxazol-3-one as starting materials, the title compounds were prepared as white solids.

Compound #83:
$^1$H NMR: (CDCl$_3$) δ 7.75 (s, 1H), 7.60 (d, J=5.5 Hz, 2H), 7.50 (m, 2H), 7.25 (d, J=5.5 Hz, 1H), 7.00 (d, J=6.0 Hz, 1H), 5.90 (d, J=4.5 Hz, 1H), 4.20 (m, 1H), 3.90 (s, 1H), 2.90 (t, J=2.5 Hz, 4H), 1.60 (m, 4H), 1.50 (s, 3H), 1.40 (m, 2H), 1.35 (s, 3H)

MS (m/z): MNa$^+$ 515.

Compound #84:
$^1$H NMR: (CDCl$_3$) δ 7.65 (d, J=6.0 Hz, 1H), 7.55 (d, J=6.5 Hz, 2H), 7.30 (s, 1H), 7.20 (d, J=6.5 Hz, 1H), 7.15 (s, 1H), 7.00 (d, J=6.5 Hz, 1H), 5.70 (d, J=7.0 Hz, 1H), 4.20 (m, 1H), 3.90 (d, J=4.5 Hz, 1H), 2.75 (t, J=1.5 Hz, 4H), 1.60 (s, 3H), 1.50 (m, 4H), 1.35 (m, 2H), 1.35 (s, 3H)

MS (m/z): MNa$^+$ 515.

Example 57

4R-(5-Chloro-benzo[d]isoxazol-3-ylamino)-2,2-dimethyl-6-(piperidine-1-sulfonyl)-chroman-3S-ol (Compound #88)

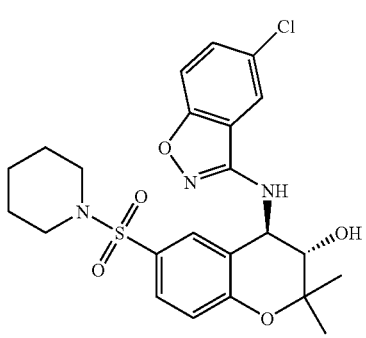

Following the procedure in Example 1, using (S,S)-6-piperidinylsulfonyl-2,2-dimethyl-1a,7b-dihydro-2H-1,3-dioxa-cyclopropa[a]naphthalene and 5-chloro-benzo[d]isoxazol-3-ylamine as starting materials, the title compound was prepared as a white solid.

$^1$H NMR: (CDCl$_3$) δ 7.75 (s, 1H), 7.55 (m, 2H), 7.45-7.30 (m, 2H), 6.90 (d, J=6.5 Hz, 1H), 5.80 (m, 1H), 5.10 (m, 1H), 4.60 (s, 1H), 2.80 (t, J=1.5 Hz, 4H), 1.55 (m, 4H), 1.35 (m, 2H), 1.35 (m, 6H)

MS (m/z): MH$^+$ 492

Example 58

4R-(6-Chloro-benzo[d]isoxazol-3-yloxy)-3S-hydroxy-2,2-dimethyl-chroman-6-sulfonic acid diethylamide (Compound #79)

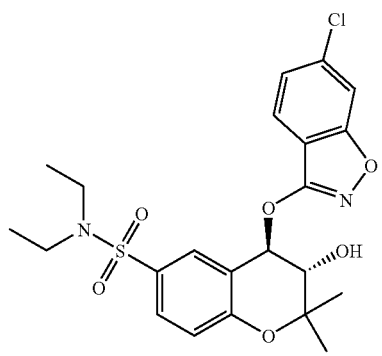

Following the procedure in Example 1, using (S,S)-6-diethylsulfonyl-2,2-dimethyl-1a,7b-dihydro-2H-1,3-dioxa-cyclopropa[a]naphthalene (literature known compound) and 6-chloro-benzo[d]isoxazol-3-oneas starting materials, the title compound was prepared as a white solid.

$^1$H NMR: (CDCl$_3$) δ 7.80 (s, 1H), 7.70 (d, J=5.5 Hz, 2H), 7.50 (m, 2H), 7.25 (m, 1H), 7.00 (d, J=6.0 Hz, 1H), 5.90 (d, J=4.5 Hz, 1H), 4.15 (m, 1H), 3.80 (d, J=3.0 Hz, 1H), 3.20 (m, 4H), 1.50 (s, 3H), 1.35 (s, 3H), 1.10 (t, J=4.5 Hz, 6H)

MS (m/z): MH$^+$ 481.

Example 59

4R-(5-Chloro-benzo[d]isoxazol-3-yloxy)-3S-hydroxy-2,2-dimethyl-chroman-6-sulfonic acid diethylamide (Compound #85)

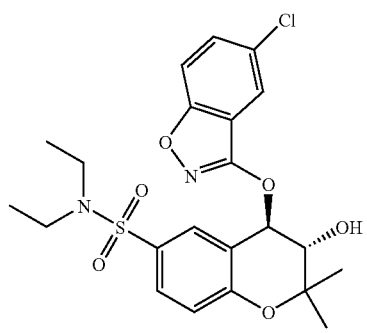

and 4R-(5-Chloro-3-oxo-3H-benzo[d]isoxazol-2-yl)-3S-hydroxy-2,2-dimethyl-chroman-6-sulfonic acid diethylamide (Compound #86)

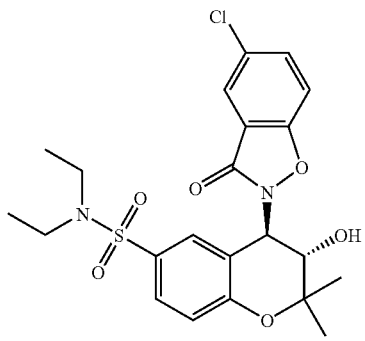

Following the procedure in Example 1, using (S,S)-6-diethylsulfonyl-2,2-dimethyl-1a,7b-dihydro-2H-1,3-dioxa-cyclopropa[a]naphthalene and 5-chloro-benzo[d]isoxazol-3-oneas starting materials, the title compounds were prepared as white solids.

Compound #85:
¹H NMR: (CDCl₃) δ 7.80 (s, 1H), 7.70 (d, J=5.5 Hz, 2H), 7.50 (m, 2H), 7.40 (m, 1H), 7.00 (d, J=5.0 Hz, 1H), 5.90 (d, J=4.5 Hz, 1H), 4.15 (m, 1H), 3.80 (d, J=2.0 Hz, 1H), 3.20 (m, 4H), 1.50 (s, 3H), 1.35 (s, 3H), 1.10 (t, J=4.5 Hz, 6H)
MS (m/z): MH⁺ 481.

Compound #86:
¹H NMR: (CDCl₃) δ 7.65 (m, 2H), 7.55 (d, J=6.5 Hz, 1H), 7.40 (s, 1H), 7.15 (d, J=6.5 Hz, 1H), 6.95 (d, J=6.5 Hz, 1H), 5.70 (d, J=7.0 Hz, 1H), 4.20 (m, 1H), 3.90 (m, 1H), 3.00 (m, 4H), 1.60 (s, 3H), 1.35 (s, 3H), 1.00 (t, J=4.5 Hz, 6H)
MS (m/z): MH⁺ 481.

Example 60

4R-(5-Chloro-benzo[d]isoxazol-3-ylamino)-3S-hydroxy-2,2-dimethyl-chroman-6-sulfonic acid diethylamide (Compound #80)

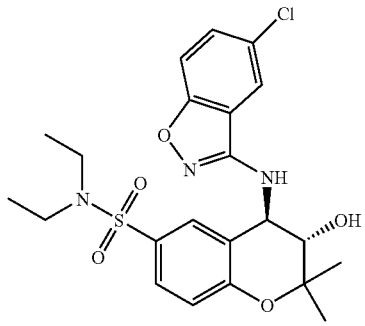

Following the procedure in Example 1, using 6-diethylsulfonyl-2,2-dimethyl-1a,7b-dihydro-2H-1,3-dioxa-cyclopropa[a]naphthalene and 5-chloro-benzo[d]isoxazol-3-ylamine as starting materials, the title compound was prepared as a white solid.

¹H NMR: (CDCl₃) δ 7.80 (s, 1H), 7.55-7.40 (m, 4H), 6.85 (d, J=5.0 Hz, 1H), 5.20 (d, J=5.0 Hz, 1H), 4.90 (m, 1H), 3.90 (m, 1H), 3.60 (d, J=1.0 Hz, 1H), 3.10 (m, 4H), 1.50 (s, 3H), 1.30 (s, 3H), 1.00 (t, J=4.5 Hz, 6H)
MS (m/z): MH⁺ 480

Example 61

4R-(7-Chloro-benzo[d]isoxazol-3-ylamino)-3S-hydroxy-2,2-dimethyl-chroman-6-sulfonic acid diethylamide (Compound #82)

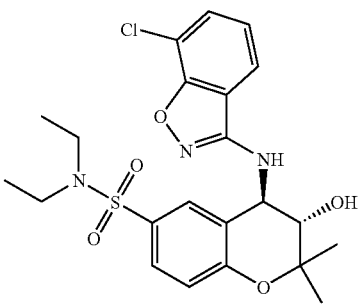

Following the procedure in Example 1, using (S,S)-6-diethylsulfonyl-2,2-dimethyl-1a,7b-dihydro-2H-1,3-dioxa-cyclopropa[a]naphthalene and 7-chloro-benzo[d]isoxazol-3-ylamine as starting materials, the title compound was prepared as a white solid.

¹H NMR: (CDCl₃) δ 7.75 (s, 1H), 7.50-7.40 (m, 3H), 7.00 (m, 1H), 6.80 (d, J=5.0 Hz, 1H), 5.50 (d, J=3.0 Hz, 1H), 4.90 (m, 1H), 3.90 (d, J=3.0 Hz, 1H), 3.60 (br, 1H), 3.05 (m, 4H), 1.50 (s, 3H), 1.25 (s, 3H), 1.00 (t, J=4.5 Hz, 6H)
MS (m/z): MH⁺ 480

Example 62

4R-(6-Chloro-benzo[d]isoxazol-3-ylamino)-3S-hydroxy-2,2-dimethyl-chroman-6-sulfonic acid diethylamide (Compound #81)

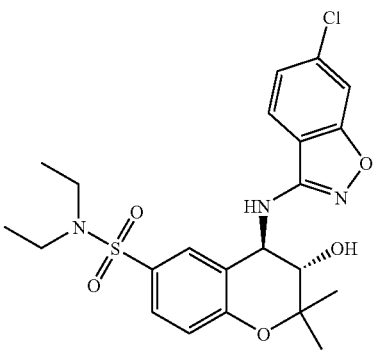

Following the procedure in Example 1, using (S,S)-6-diethylsulfonyl-2,2-dimethyl-1a,7b-dihydro-2H-1,3-dioxa-cyclopropa[a]naphthalene and 6-chloro-benzo[d]isoxazol-3-ylamine as starting materials, the title compound was prepared as a white solid.

¹H NMR: (CDCl₃) δ 7.80 (s, 1H), 7.55-7.40 (m, 4H), 6.85 (d, J=5.0 Hz, 1H), 5.20 (d, J=5.0 Hz, 1H), 4.90 (m, 1H), 3.90 (m, 1H), 3.60 (d, J=1.0 Hz, 1H), 3.10 (m, 4H), 1.50 (s, 3H), 1.30 (s, 3H), 1.00 (t, J=4.5 Hz, 6H)
MS (m/z): MH⁺ 480

Example 63

6-(3-Fluoro-phenylsulfanyl)-2,2-dimethyl-2H-chromene

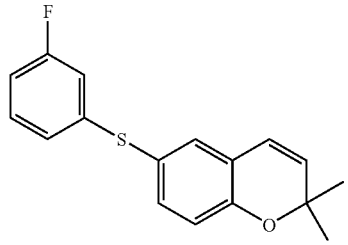

Following the procedure in Example 49, using bis(3-Fluoro-benzene)-sulfide as starting material, the title compound was prepared as a white solid.

$^1$H NMR (CDCl$_3$) δ 7.95 (m, 1H), 7.80 (m, 1H), 7.70 (m, 1H), 7.60 (m, 1H), 7.50 (m, 1H), 7.25 (m, 1H), 6.90 (m, 1H), 3.95 (m, 1H), 3.55 (m, 1H), 1.55 (s, 3H), 1.25 (s, 3H)

MS (m/z): MH$^+$ 335

Example 64

(S,S)-6-(3-Fluoro-benzenesulfonyl)-2,2-dimethyl-1a,7b-dihydro-2H-1,3-dioxa-cyclopropa[a]naphthalene

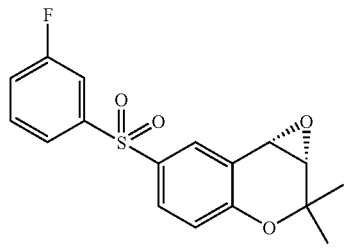

Following the procedure in Example 50, using 6-(3-fluoro-phenylsulfanyl)-2,2-dimethyl-2H-chromene (prepared as in Example 64) as starting material, the title compound was prepared as a white solid.

$^1$H NMR (CDCl$_3$) δ 7.95 (s, 1H), 7.80 (m, 1H), 7.70 (m, 1H), 7.60 (m, 1H), 7.50 (m, 1H), 7.25 (m, 1H), 6.90 (m, 1H), 3.95 (m, 1H), 3.55 (m, 1H), 1.55 (s, 3H), 1.25 (s, 3H)

MS (m/z): MH$^+$ 335.

Example 65

4R-(6-Chloro-benzo[d]isoxazol-3-yloxy)-6-(3-fluoro-benzenesulfonyl)-2,2-dimethyl-chroman-3S-ol (Compound #99)

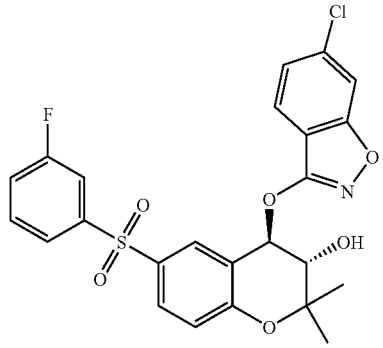

and 4R-6-Chloro-2-[6-(3-fluoro-benzenesulfonyl)-3S-hydroxy-2,2-dimethyl-chroman-4-yl]-R-benzo[d]isoxazol-3-one (Compound #100)

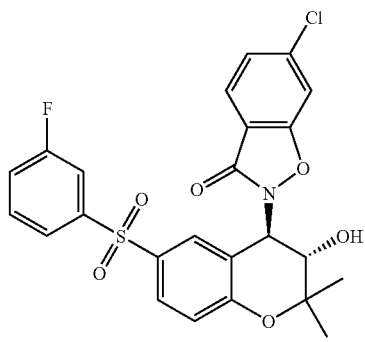

Following the procedure in Example 1, using (S,S)-6-(m-fluorobenzenesulfonyl)-2,2-dimethyl-1a,7b-dihydro-2H-1,3-dioxa-cyclopropa[a]naphthalene and 6-chloro-benzo[d]isoxazol-3-oneas starting materials, the title compounds were prepared as white solids.

Compound #99:

$^1$H NMR: (CDCl$_3$) δ 8.00 (s, 1H), 7.80 (d, J=5.5 Hz, 1H), 7.70 (d, J=5.0 Hz, 1H), 7.55 (d, J=5.0 Hz, 1H), 7.50 (m, 2H), 7.25 (m, 3H), 7.00 (d, J=5.5 Hz, 1H), 5.90 (d, J=4.5 Hz, 1H), 4.15 (m, 1H), 3.90 (m, 1H), 1.50 (s, 3H), 1.35 (s, 3H)

MS (m/z): MH$^+$ 504.

Compound #100:

$^1$H NMR: (CDCl$_3$) δ 7.75 (d, J=5.5 Hz, 1H), 7.65 (d, J=5.0 Hz, 1H), 7.5 (m, 2H), 7.45 (m, 2H), 7.20 (m, 2H), 7.10 (s, 1H), 7.00 (d, J=5.5 Hz, 1H), 5.60 (d, J=6.5 Hz, 1H), 4.15 (m, 1H), 1.50 (s, 3H), 1.35 (s, 3H)

MS (m/z): MH$^+$ 504.

Example 66

4R-(5-Chloro-benzo[d]isoxazol-3-ylamino)-6-(3-fluoro-benzenesulfonyl)-2,2-dimethyl-chroman-3S-ol (Compound #103)

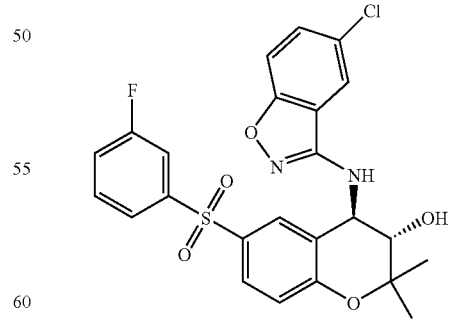

Following the procedure in Example 1, using (S,S)-6-(m-fluorobenzenesulfonyl)-2,2-dimethyl-1a,7b-dihydro-2H-1,3-dioxa-cyclopropa[a]naphthalene and 4-(2-chloro-propenyl)-isoxazol-3-ylamine as starting materials, the title compound was prepared as a white solid.

¹H NMR: (CDCl₃) δ 7.90 (s, 1H), 7.60-7.20 (m, 9H), 6.80 (d, J=5.5 Hz, 1H), 5.60 (d, J=5.5 Hz, 1H), 4.90 (m, 1H), 4.20 (br, 1H), 3.90 (d, J=5.5 Hz, 1H), 1.50 (s, 3H), 1.35 (s, 3H)
MS (m/z): MH⁺ 503.

Example 67

6-(4-Chloro-phenylsulfanyl)-2,2-dimethyl-2H-chromene

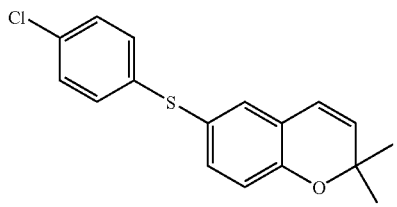

Following the procedure in Example 49, using bis(4-chloro-phenyl) sulfide as starting material, the title compound was prepared as a white solid.
MS (m/z): MH⁺ 304.

Example 68

(S,S)-6-(4-Chloro-benzenesulfonyl)-2,2-dimethyl-1a,7b-dihydro-2H-1,3-dioxa-cyclopropa[a]naphthalene

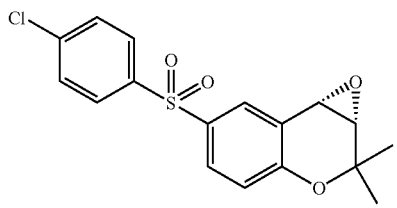

Following the procedure in Example 50, using 6-(4-chloro-phenylsulfanyl)-2,2-dimethyl-2H-chromene as starting material, the title compound was prepared as a white solid.
¹H NMR (CDCl₃) δ 7.95 (s, 1H), 7.85 (m, 2H), 7.80 (m, 1H), 7.50 (m, 2H), 6.85 (m, 1H), 3.95 (m, 1H), 3.55 (m, 1H), 1.55 (s, 3H), 1.25 (s, 3H)
MS (m/z): MH⁺ 351

Example 69

6-(4-Chloro-benzenesulfonyl)-4R-(6-chloro-benzo[d]isoxazol-3-yloxy)-2,2-dimethyl-chroman-3S-ol (Compound #101)

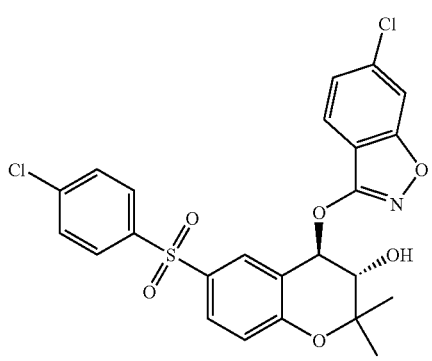

and 6-Chloro-2-[6-(4-chloro-benzenesulfonyl)-3S-hydroxy-2,2-dimethyl-chroman-4-yl]-R-benzo[d]isoxazol-3-one (Compound #102)

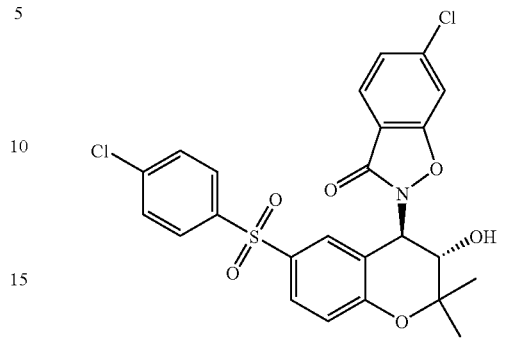

Following the procedure in Example 1, using (S,S)-6-(p-chlorobenzenesulfonyl)-2,2-dimethyl-1a,7b-dihydro-2H-1,3-dioxa-cyclopropa[a]naphthalene and 6-chloro-benzo[d]isoxazol-3-one as starting materials, the title compounds were prepared as white solid.
Compound #101:
¹H NMR: (CDCl₃) δ 8.00 (s, 1H), 7.80 (m, 3H), 7.50 (m, 4H), 7.30 (m, 1H), 7.00 (d, J=5.5 Hz, 1H), 5.90 (d, J=4.5 Hz, 1H), 4.15 (m, 1H), 3.80 (d, J=1.0 Hz, 1H), 1.50 (s, 3H), 1.35 (s, 3H)
MS (m/z): MH⁺ 521.
Compound #102:
¹H NMR: (CDCl₃) δ 7.70 (m, 4H), 7.55 (s, 1H), 7.35 (d, J=5.0 Hz, 2H), 7.20 (d, J=5.0 Hz, 1H), 7.10 (s, 1H), 7.00 (d, J=5.5 Hz, 1H), 5.60 (d, J=6.5 Hz, 1H), 4.15 (m, 1H), 4.00 (m, 1H), 1.55 (s, 3H), 1.30 (s, 3H)
MS (m/z): MH⁺ 504.

Example 70

6-(4-Methoxy-phenylsulfanyl)-2,2-dimethyl-2H-chromene

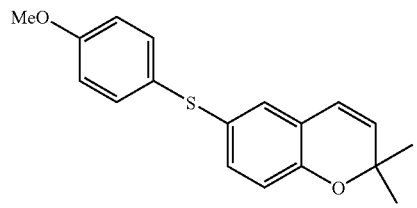

Following the procedure in Example 49, using bis(4-methoxy-phenyl) sulfide as starting material, the title compound was prepared as a white solid.
MS (m/z): MH⁺ 299.

Example 71

(S,S)-6-(4-Methoxy-benzenesulfonyl)-2,2-dimethyl-1a,7b-dihydro-2H-1,3-dioxa-cyclopropa[a]naphthalene

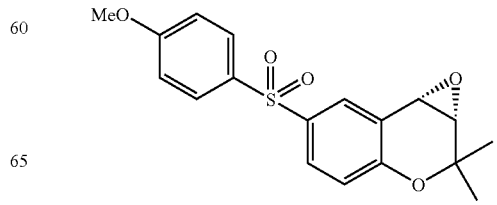

Following the procedure in Example 50, using 6-(4-methoxy-phenylsulfanyl)-2,2-dimethyl-2H-chromene as starting material, the title compound was prepared as a white solid.

¹H NMR (CDCl₃) δ 7.90 (s, 1H), 7.85 (m, 2H), 7.75 (m, 1H), 7.95 (m, 2H), 6.85 (m, 1H), 3.95 (m, 1H), 3.85 (s, 3H), 3.50 (m, 1H), 1.55 (s, 3H), 1.25 (s, 3H)

MS (m/z): MH⁺ 347

Example 72

4R-(6-Chloro-benzo[d]isoxazol-3-yloxy)-6-(4-methoxy-benzenesulfonyl)-2,2-dimethyl-chroman-3S-ol (Compound #97)

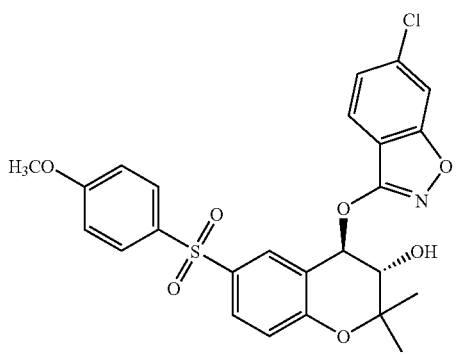

and 6-Chloro-2-[3S-hydroxy-6-(4-methoxy-benzenesulfonyl)-2,2-dimethyl-chroman-4-yl]-4R-benzo[d]isoxazol-3-one (Compound #98)

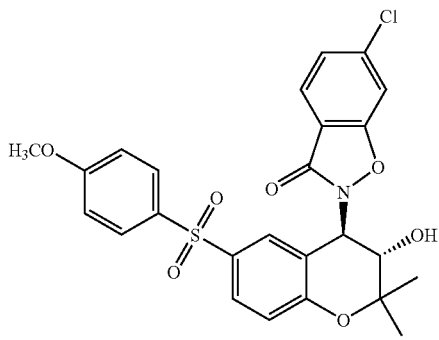

Following the procedure in Example 1, using (S,S)-6-(p-methoxybenzenesulfonyl)-2,2-dimethyl-1a,7b-dihydro-2H-1,3-dioxa-cyclopropa[a]naphthalene and 6-chloro-benzo[d]isoxazol-3-one as starting materials, the title compounds were prepared as white solids.

Compound #97:
¹H NMR: (CDCl₃) δ 7.90 (s, 1H), 7.80 (m, 3H), 7.50 (m, 2H), 7.30 (m, 1H), 6.90 (m, 3H), 5.85 (d, J=4.5 Hz, 1H), 4.15 (m, 1H), 3.85 (m, 1H), 3.80 (s, 3H), 1.50 (s, 3H), 1.35 (s, 3H)
MS (m/z): MH⁺ 516.

Compound #98:
¹H NMR: (CDCl₃) δ 7.70 (m, 4H), 7.50 (s, 1H), 7.20 (d, J=5.0 Hz, 1H), 7.10 (s, 1H), 6.90 (d, J=5.0 Hz, 1H), 6.85 (d, J=5.5 Hz, 2H), 5.60 (d, J=6.5 Hz, 1H), 4.15 (m, 1H), 3.80 (s, 3H), 1.55 (s, 3H), 1.30 (s, 3H)
MS (m/z): MH⁺ 516.

Example 73

4R-(5-Chloro-benzo[d]isoxazol-3-ylamino)-6-(4-methoxy-benzenesulfonyl)-2,2-dimethyl-chroman-3S-ol (Compound #104)

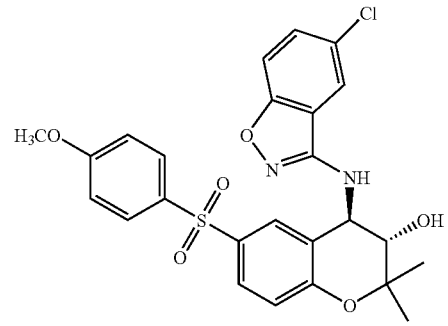

Following the procedure in Example 1, using (S,S)-6-(p-chlorobenzenesulfonyl)-2,2-dimethyl-1a,7b-dihydro-2H-1,3-dioxa-cyclopropa[a]naphthalene and 5-chloro-benzo[d]isoxazol-3-ylamine as starting materials, the title compound was prepared as a white solid.

¹H NMR: (CDCl₃) δ 7.90 (s, 1H), 7.75 (d, J=5.5 Hz, 2H), 7.60 (d, J=5.5 Hz, 1H), 7.50 (d, J=5.5 Hz, 1H), 7.40 (s, 1H), 7.18 (d, J=5.5 Hz, 1H), 6.90 (d, J=5.5 Hz, 2H), 6.85 (m, 1H), 5.60 (d, J=5.5 Hz, 1H), 4.90 (m, 1H), 3.90 (m, 1H), 3.80 (s, 3H), 3.70 (d, J=1.5 Hz, 1H), 1.50 (s, 3H), 1.35 (s, 3H)

MS (m/z): MH⁺ 515.

Example 74

1,2-Dichloro-4-(1,1-dimethyl-prop-2-ynyloxy)-benzene

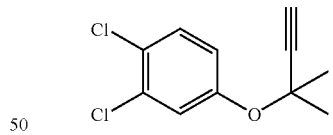

2-Methyl-but-3-yn-2-ol (1.68 g, 20 mmol) in acetonitrile (10 ml) was treated with DBU (20 mmol) and trifluoroacetic anhydride (20 mmol) at 0° C. The resulting mixture was stirred at 0° C. for 20 mins and then transferred to the solution of 3,4-dichlorophenol in acetonitrile (15 ml) with DBU (22 mmol) and CuCl₂.H₂O (10 mg) at the same temperature over a period of about 10 mins. The reaction mixture was stirred for 2 h and then quenched with H₂O. Ethyl acetate was added to extract the product twice. Organic layer was washed with brine, dried and concentrated to yield the title compound as a colorless liquid.

¹H NMR (CDCl₃) δ 7.32 (m, 2H), 7.05 (m, 1H), 1.62(s, 6H).

Example 75

6,7-Dichloro-2,2-dimethyl-2H-chromene

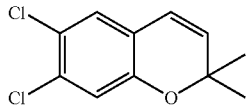

6,7-Dichloro-2,2-dimethyl-2H-chromene (4.0 g, 17.5 mmol) in N,N-diethylaniline (DEA, 30 ml) was heated to 180° C. for 2 h. The reaction mixture was cooled down to room temperature and then quenched with $H_2O$. Ethyl acetate was added to extract the product twice. The organic layer was washed with brine, dried and concentrated to yield the title compound as a colorless liquid.

$^1$H NMR (CDCl$_3$) δ 7.32 (m, 2H), 7.05 (m, 1H), 1.62(s, 6H).

Example 76

(S,S)-5,6-Dichloro-2,2-dimethyl-1a,7b-dihydro-2H-1,3-dioxa-cyclopropa[a]naphthalene

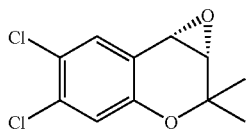

Following the procedure in Example 50, using 6,7-dichloro-2,2-dimethyl-2H-chromeneas starting material, the title compound was prepared as a white solid.

$^1$H NMR (CDCl$_3$) δ 7.30 (m, 1H), 6.70 (m, 1H), 4.49 (m, 1H), 3.50 (m, 1H), 1.60 (s, 3H), 1.25 (s, 3H)

MS (m/z): MH$^+$ 244.

Example 77

6,7-Dichloro-4R-(6-chloro-benzo[d]isoxazol-3-yloxy)-2,2-dimethyl-chroman-3S-ol (Compound #93)

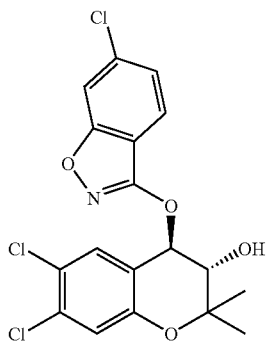

and 6-Chloro-2-(6,7-dichloro-3S-hydroxy-2,2-dimethyl-chroman-4-yl)-R-benzo[d]isoxazol-3-one (Compound # 94)

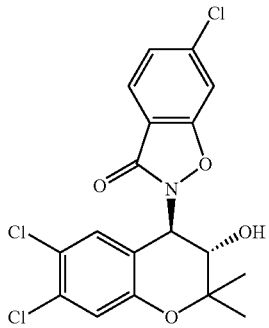

Following the procedure in Example 1, using (S,S)-5,6-dichloro-2,2-dimethyl-1a,7b-dihydro-2H-1,3-dioxa-cyclopropa[a]naphthalene and 6-chloro-benzo[d]isoxazol-3-one as starting materials, to yield the title compounds as white solids.

Compound #94:
$^1$H NMR: (CDCl$_3$) δ 7.50 (d, J=5.0 Hz, 1H), 7.35 (d, J=5.0 Hz, 1H), 7.15 (m, 2H), 6.80 (d, J=5.0 Hz, 1H), 5.65 (d, J=4.5 Hz, 1H), 4.80 (br, 1H), 4.20 (d, J=4.5 Hz, 1H), 1.55 (s, 3H), 1.35 (s, 3H)
MS (m/z): MH$^+$ 414.

Compound #93:
$^1$H NMR: (CDCl$_3$) δ 7.50 (d, J=4.0 Hz, 1H), 7.45 (s, 1H), 7.40 (d, J=4.0 Hz, 1H), 7.25 (m, 1H), 6.80 (d, J=5.0 Hz, 1H), 5.85 (d, J=1.0 Hz, 1H), 4.30 (m, 1H), 3.70 (d, J=2.0 Hz, 1H), 1.55 (s, 6H)
MS (m/z): MH$^+$ 414.

Example 78

6,7-Dichloro-4R-(5-chloro-benzo[d]isoxazol-3-ylamino)-2,2-dimethyl-chroman-3S-ol (Compound #91)

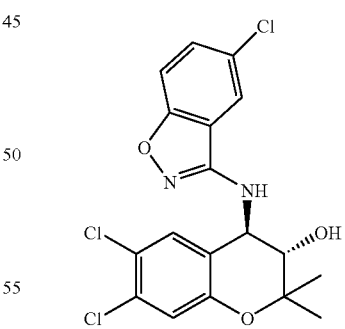

Following the procedure in Example 1, using (S,S)-5,6-dichloro-2,2-dimethyl-1a,7b-dihydro-2H-1,3-dioxa-cyclopropa[a]naphthalene and 5-chloro-benzo[d]isoxazol-3-ylamine as starting materials, the title compound was prepared as a white solids.

$^1$H NMR: (CDCl$_3$) δ 7.55 (s, 1H), 7.45 (d, J=4.5 Hz, 1H), 7.30 (d, J=4.5 Hz, 2H), 6.90 (d, J=4.5 Hz, 1H), 6.85 (m, 1H), 5.00 (m, 1H), 4.85 (m, 1H), 4.25 (m, 1H), 1.50 (s, 3H), 1.35 (s, 3H)
MS (m/z): MNa$^+$ 435.

Example 79

2,2-Dimethyl-2H-chromene-6-carboxylic acid diethylamide

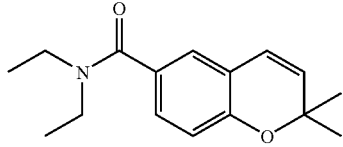

Following the procedure in Example 49, using 6-bromo-2,2-dimethyl-2H-chromene as starting material, the title compound was prepared as a white solid.

$^1$H NMR (CDCl$_3$) δ 7.10 (m, 1H), 7.05 (s, 1H), 6.75 (m, 1H), 6.30 (m, 1H), 5.65 (m, 1H), 3.40 (m, 4H), 1.45 (s, 6H), 1.15 (m, 6H)

MS (m/z): MH$^+$ 260

Example 80

(S,S)-2,2-Dimethyl-1a,7b-dihydro-2H-1,3-dioxa-cyclopropa[a]naphthalene-6-carboxylic acid diethylamide

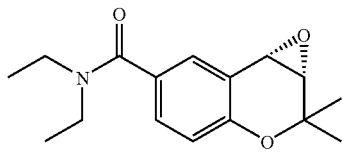

Following the procedure in Example 50, using 2,2-dimethyl-2H-chromene-6-carboxylic acid diethylamide (Example 79) as starting material, the title compound was prepared as a white solid.

$^1$H NMR (CDCl$_3$) δ 7.40 (m, 1H), 7.24 (m, 1H), 6.80 (m, 1H), 3.90 (m, 1H), 3.50 (m, 1H), 3.40 (m, 4H), 1.55 (s, 3H), 1.25 (s, 3H), 1.20 (m, 6H)

MS (m/z): MH$_2$O+294

Example 81

4R-(6-Chloro-benzo[d]isoxazol-3-yloxy)-3S-hydroxy-2,2-dimethyl-chroman-6-carboxylic acid diethylamide (Compound #90)

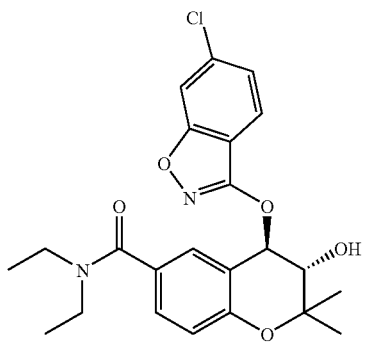

Following the procedure in Example 1, using (S,S)-2,2-dimethyl-1a,7b-dihydro-2H-1,3-dioxa-cyclopropa[a]naphthalene-6-carboxylic acid diethylamide and 6-chloro-benzo[d]isoxazol-3-one as starting materials, the title compound was prepared as a white solid.

$^1$H NMR: (CDCl$_3$) δ 7.55 (m, 2H), 7.50 (s, 1H), 7.30 (m, 2H), 6.90 (d, J=4.5 Hz, 1H), 6.15 (m, 1H), 4.40 (m, 1H), 3.40 (m, 4H), 3.20 (m, 1H), 1.55 (s, 3H), 1.40 (s, 3H), 1.20 (m, 6H)

MS (m/z): MH$^+$ 446.

Example 82

4R-(5-Chloro-benzo[d]isoxazol-3-ylamino)-3S-hydroxy-2,2-dimethyl-chroman-6-carboxylic acid diethylamide (Compound #89)

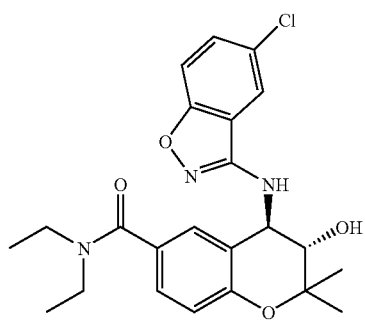

Following the procedure in Example 1, using (S,S)-2,2-dimethyl-1a,7b-dihydro-2H-1,3-dioxa-cyclopropa[a]naphthalene-6-carboxylic acid diethylamide and 5-chloro-benzo[d]isoxazol-3-ylamine as starting materials, the title compound was prepared as a white solid.

$^1$H NMR: (CDCl$_3$) δ 7.40 (m, 2H), 7.20 (m, 3H), 6.70 (d, J=4.5 Hz, 1H), 6.20 (d, J=4.5 Hz, 1H), 4.65 (m, 1H), 4.20 (m, 1H), 4.60-3.30 (m, 4H), 3.10 (m, 1H), 1.40 (s, 3H), 1.20 (s, 3H), 1.15 (m, 6H)

MS (m/z): MH$^+$ 444.

Example 83

(S,S)-(2,2-Dimethyl-1a,7b-dihydro-2H-1,3-dioxa-cyclopropa[a]naphthalen-6-yl)-phenyl-methanone

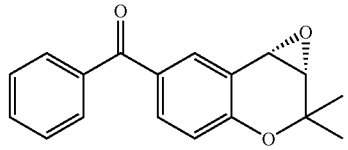

Following the procedure in Example 50, using (2,2-dimethyl-2H-chromen-6-yl)-phenyl-methanone as starting material, the title compound was prepared as a white solid.

$^1$H NMR (CDCl$_3$) δ 7.90 (s, 1H), 7.75 (m, 3H), 7.55 (m, 1H), 7.45 (m, 2H), 6.88 (m, 1H), 3.95 (m, 1H), 3.55 (m, 1H), 1.60 (m, 6H)

MS (m/z): MH$^+$ 299

Example 84

4R-(6-Chloro-benzo[d]isoxazol-3-yloxy)-3S-hydroxy-2,2-dimethyl-chroman-6-yl]-phenyl-methanone (Compound #95)

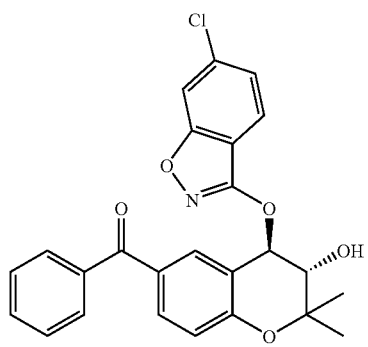

and 2-(6-Benzoyl-3S-hydroxy-2,2-dimethyl-chroman-4-yl)-6-chloro-4R-benzo[d]isoxazol-3-one (Compound #96)

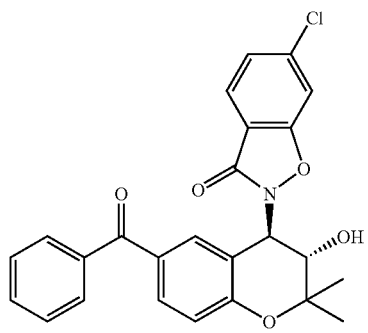

Following the procedure in Example 1, using (S,S)-(2,2-dimethyl-1a,7b-dihydro-2H-1,3-dioxa-cyclopropa[a]naphthalen-6-yl)-phenyl-methanone and 6-chloro-benzo[d]isoxazol-3-one as starting materials, the title compounds were prepared as white solids.

Compound #95:
$^1$H NMR: (CDCl$_3$) δ 8.05 (s, 1H), 7.75 (m, 3H), 7.60-7.40 (m, 5H), 7.30 (d, J=4.5 Hz, 1H), 6.95 (d, J=4.5 Hz, 1H), 6.15 (m, 1H), 4.45 (m, 1H), 2.30 (m, 1H), 1.60 (s, 3H), 1.40 (s, 3H)
MS (m/z): MH$^+$ 450.

Compound #96:
$^1$H NMR: (CDCl$_3$) δ 7.75 (m, 1H), 7.60 (m, 3H), 7.45 (m, 2H), 7.25 (m, 2H), 7.20 (m, 2H), 6.95 (d, J=4.5 Hz, 1H), 5.70 (m, 1H), 4.20 (d, J=5.0 Hz, 1H), 3.80 (br, 1H), 1.60 (s, 3H), 1.40 (s, 3H)
MS (m/z): MH$^+$ 450.

Example 85

[4R-(5-Chloro-benzo[d]isoxazol-3-ylamino)-3S-hydroxy-2,2-dimethyl-chroman-6-yl]-phenyl-methanone (Compound #92)

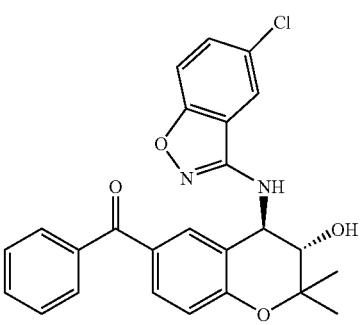

Following the procedure in Example 1, using (S,S)-(2,2-dimethyl-1a,7b-dihydro-2H-1,3-dioxa-cyclopropa[a]naphthalen-6-yl)-phenyl-methanone and 5-chloro-benzo[d]isoxazol-3-ylamine as starting materials, the title compound was prepared as a white solid.

$^1$H NMR: (CDCl$_3$) δ 7.90 (s, 1H), 7.70 (s, 1H), 7.50 (m, 4H), 7.30 (m, 3H), 7.25 (m, 1H), 6.75 (d, J=4.5 Hz, 1H), 5.65 (d, J=4.5 Hz, 1H), 5.00 (m, 1H), 4.20 (br, 1H), 3.70 (d, J=4.5 Hz, 1H), 1.45 (s, 3H), 1.30 (s, 3H)
MS (m/z): MH$^+$ 449.

Example 86

3-Hydroxy-2,2-dimethyl-4-(4-oxo-1,4-dihydro-quinazolin-2-ylamino)-chroman-6-carbonitrile (Compound #118)

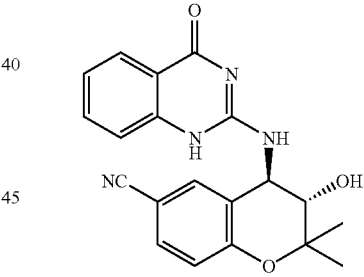

and 2,2-Dimethyl-4-(4-oxo-1,4-dihydro-quinazolin-2-ylamino)-2H-chromene-6-carbonitrile (Compound #46)

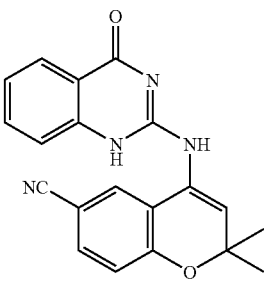

Following the procedure in Example 1, using 2,2-dimethyl-1a,7b-dihydro-2H-1,3-dioxa-cyclopropa[a]naphthalene-6-carbonitrile and 2-amino-1H-quinazolin-4-one as starting materials, the title compounds were prepared as white solids.

Compound #118:
$^1$H NMR: (CDCl$_3$) δ 6.95~7.85 (m, 7H), 5.20 (s, br, 1H), 5.05 (d, J=8.5 Hz, 1H), 4.10 (d, J=8.5 Hz, 1H), 1.55 (s, 3H), 1.41 (s, 3H)
MS (m/z): MH$^+$ 363.

Compound #46:
MS (m/z): MH$^+$ 345.

Example 87

4-(6-Chloro-4-oxo-1,4-dihydro-quinazolin-2-ylamino)-3-hydroxy-2,2-dimethyl-chroman-6-carbonitrile (Compound #7)

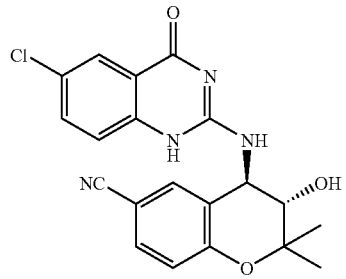

4-Amino-3-hydroxy-2,2-dimethyl-chroman-6-carbonitrile (5 mmoL) and 6-chloro-2-methoxy-1H-quinazolin-4-one (5 mmoL) in toluene (15 mL) in a sealed tube were heated at 150° C. for 4 hrs. The solvent was removed and the residue was purified by silica gel chromatography with hexanes and ethyl acetate to yield the title compound as white solid.

$^1$H NMR: (CDCl$_3$) δ 7.95 (s, 1H), 7.65 (m, 1H), 7.60 (d, J=7.5 Hz, 1H), 7.51 (s, 1H), 7.48 (d, J=8.0 Hz, 1H), 7.32 (d, J=8.0 Hz, 1H), 5.31 (d, J=4.0 Hz, 1H), 3.72 (d, J=7.5 Hz, 1H), 1.58 (s, 3H), 1.38 (s, 3H)
MS (m/z): MH$^+$ 398.

Example 88

(3S,4R)-4-(6-Chloro-4-oxo-1,4-dihydro-quinazolin-2-ylamino)-3-hydroxy-2,2-dimethyl-chroman-6-carbonitrile (Compound #64)

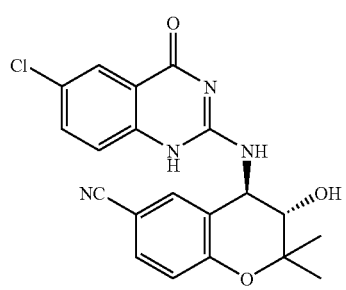

Following the procedure in Example 8, using (3S,4R)-4-amino-3-hydroxy-2,2-dimethyl-chroman-6-carbonitrile as starting material, the title compound was prepared as a solid. The $^1$H NMR for this product was the same as that of Example 87.

Example 89

4R-(1,3-Dioxo-1,3-dihydro-pyrrolo[3,4-c]pyridin-2-yl)-3S-hydroxy-2,2-dimethyl-chroman-6-carbonitrile (Compound #26)

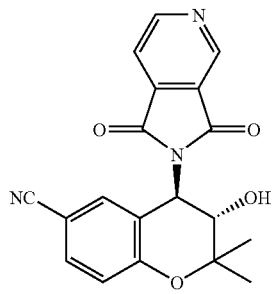

(3S,4R)-4-amino-3-hydroxy-2,2-dimethyl-chroman-6-carbonitrile (1 mmoL) and furo[3,4-c]pyridine-1,3-dione(1 mmoL) in toluene (5 mL) in a sealed tube were heated at 120° C. for 10 hrs. The reaction mixture was cooled down and the solvent was removed. The residue was purified by silica gel chromatography with hexanes:ethyl acetate 1:1 to yield the title compound as a yellow solid.

$^1$H NMR: (CDCl$_3$) δ 9.05 (d, J=6.0 Hz, 1H), 9.00~9.10 (br, s, 1H), 7.45 (d, J=7.5 Hz, 1H), 7.15 (s, 1H), 6.95 (d, J=7.5 Hz, 1H), 5.35 (d, J=8.2 Hz, 1H), 4.52 (dd, J=8.0, 5.8 Hz, 1H), 3.32 (s, 1H), 1.61 (s, 3H), 1.38 (s, 3H)
MS (m/z): MH$^+$ 350.

Example 90

4-(5-Chloro-1,3-dioxo-1,3-dihydro-isoindol-2-yl)-3-hydroxy-2,2-dimethyl-chroman-6-carbonitrile (Compound #115)

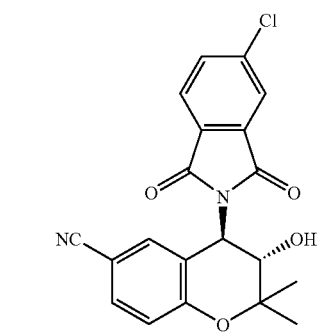

Following the procedure in Example 89, using (3S,4R)-4-amino-3-hydroxy-2,2-dimethyl-chroman-6-carbonitrile and 5-chloro-isobenzofuran-1,3-dione as starting materials, the title compound was prepared as a pale yellow solid.

$^1$H NMR: (CDCl$_3$) δ 7.80-7.70 (m, 3H), 7.40 (m, 1H), 7.15 (s, 1H), 6.90 (m, 1H), 5.30 (m, 1H), 4.45 (m, 1H), 4.35 (m, 1H), 1.55 (s, 3H), 1.30 (s, 3H)
MS (m/z): MH$^+$ 351

Example 91

4-[5-(4-Chloro-phenyl)-imidazol-1-yl]-2,2-dimethyl-3,4-dihydro-2H-pyrano[3,2-c]pyridin-3-ol (Compound #113)

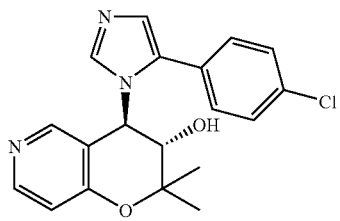

Following the procedure in Example 1, using (±)-2,2-dimethyl-1a,7b-dihydro-2H-1,3-dioxa-6-aza-cyclopropa[a]naphthalene (literature known compound) and 5-(4-chlorophenyl)-1H-imidazole as starting materials, the title compound was prepared as a pale yellow solid.

$^1$H NMR: (MeOD) δ 8.20 (d, J=1.5 Hz, 1H), 7.93 (s, 1H), 7.72 (d, J=3.0 Hz, 2H), 7.70 (s, 1H), 7.30 (d, J=3.0 Hz, 2H), 6.90 (d, J=1.5 Hz, 1H), 6.72 (s, 1H), 4.45 (d, J=3.3 Hz, 1H), 4.30 (d, J=3.3 Hz, 1H), 1.57 (s, 3H), 1.32 (s, 3H)

MS (m/z): MH$^+$ 356

Example 92

4-[2-(4-Chloro-phenyl)-imidazol-1-yl]-2,2-dimethyl-3,4-dihydro-2H-pyrano[3,2-c]pyridin-3-ol (Compound #111)

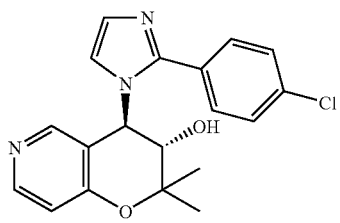

Following the procedure in Example 1, using (±)-2,2-dimethyl-1a,7b-dihydro-2H-1,3-dioxa-6-aza-cyclopropa[a]naphthalene and 2-(4-chlorophenyl)-1H-imidazole as starting materials, the title compound was prepared as a pale yellow solid.

$^1$H NMR: (CDCl$_3$) δ 8.20 (m, 1H), 7.70 (m, 2H), 7.55 (s, 1H), 7.30 (m, 2H), 6.80 (s, 1H), 6.70 (m, 1H), 6.65 (s, 1H), 6.55 (s, 1H), 5.45 (m, 1H), 4.00 (m, 1H), 1.60 (s, 3H), 1.25 (s, 3H)

MS (m/z): MH$^+$ 356

Example 93

4-[5-(4-Chloro-phenyl)-pyrazol-1-yl]-2,2-dimethyl-3,4-dihydro-2H-pyrano[3,2-c]pyridin-3-ol (Compound #108)

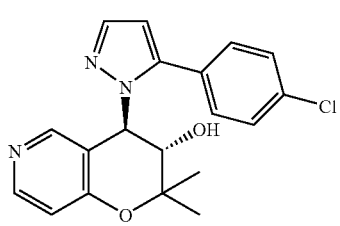

Following the procedure in Example 1, using (±)-2,2-dimethyl-1a,7b-dihydro-2H-1,3-dioxa-6-aza-cyclopropa[a]naphthalene and 5-(4-chloro-phenyl)-1H-pyrazole as starting materials, the title compound was prepared as a pale yellow solid.

$^1$H NMR: (CDCl$_3$) δ 8.20 (m, 1H), 7.70 (s, 2H), 7.60 (s, 1H), 7.32 (m, 2H), 7.22 (m, 2H), 6.70 (m, 2H), 5.00 (d, J=3.6 Hz, 1H), 3.72 (d, J=3.6 Hz, 1H), 1.60 (s, 3H), 1.30 (s, 3H)

MS (m/z): MH$^+$ 356

Example 94

2,2-Dimethyl-4-(2-phenyl-imidazol-1-yl)-3,4-dihydro-2H-pyrano[3,2-c]pyridin-3-ol (Compound #105)

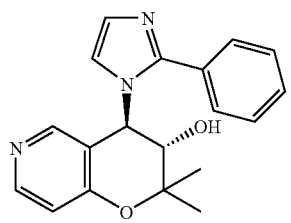

Following the procedure in Example 1, using (±)-2,2-dimethyl-1a,7b-dihydro-2H-1,3-dioxa-6-aza-cyclopropa[a]naphthalene and 2-phenyl-1H-imidazole as starting materials, the title compound was prepared as a pale yellow solid.

$^1$H NMR: (CDCl$_3$) δ 8.20 (m, 1H), 7.80 (m, 2H), 7.50 (s, 1H), 7.40 (m, 3H), 6.75 (m, 2H), 6.40 (s, 1H), 6.55 (s, 1H), 5.45 (m, 1H), 3.75 (m, 1H), 1.55 (s, 3H), 1.22 (s, 3H)

MS (m/z): MH$^+$ 356

Example 95

6-(4-Chloro-phenyl)-2-(3-hydroxy-2,2-dimethyl-3,4-dihydro-2H-pyrano[3,2-c]pyridin-4-yl)-2H-pyridazin-3-one (Compound #112)

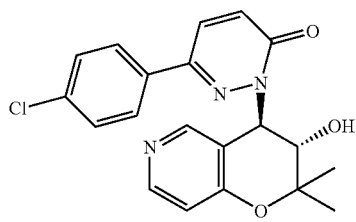

Following the procedure in Example 1, using (±)-2,2-dimethyl-1a,7b-dihydro-2H-1,3-dioxa-6-aza-cyclopropa[a]naphthalene and 6-(4-chloro-phenyl)-2H-pyridazin-3-one as starting materials, the title compound was prepared as a pale yellow solid.

$^1$H NMR (MeOD) δ 8.50 (s, 1H), 8.25 (m, 2H), 8.05 (m, 1H), 7.75 (m, 1H), 7.40 (m, 2H), 7.30 (s, 1H), 6.80 (m, 1H), 4.60 (m, 1H), 3.50 (m, 1H), 1.55 (s, 3H), 1.25 (s, 3H)

MS (m/z): MH$^+$ 384

Example 96

1-(4-Chloro-phenyl)-2-(3-hydroxy-2,2-dimethyl-3,4-dihydro-2H-pyrano[32-c]pyridin-4-yl)-1,2-dihydro-pyrazol-3-one (Compound #110)

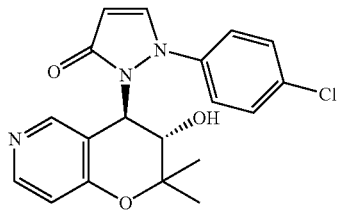

and 4-[1-(4-Chloro-phenyl)-1H-pyrazol-3-yloxy]-2,2-dimethyl-3,4-dihydro-2H-pyrano[3,2-c]pyridin-3-ol (Compound #109)

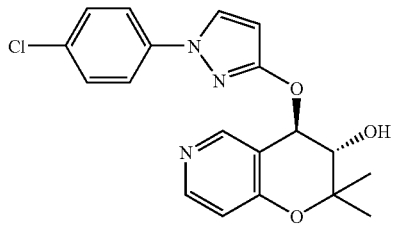

Following the procedure in Example 1, using (±)-2,2-dimethyl-1a,7b-dihydro-2H-1,3-dioxa-6-aza-cyclopropa[a]naphthalene and 1-(4-chloro-phenyl)-1,2-dihydro-pyrazol-3-one as starting materials, the title compounds were prepared as pale yellow solids.

Compound #110:
$^1$H NMR: (CDCl$_3$) δ 8.60 (s, 1H), 8.30 (d, J=1.5 Hz, 1H), 7.75 (s, 1H), 7.50 (d, J=2.5 Hz, 2H), 7.40 (d, J=2.5 Hz, 2H), 6.72 (d, J=1.5 Hz, 1H), 6.00 (s, 1H), 5.60 (d, J=2.0 Hz, 1H), 4.05 (d, J=2.0 Hz, 1H), 1.55 (s, 3H), 1.35 (s, 3H)
MS (m/z): MH$^+$ 356.

Compound #109:
MS (m/z): MH$^+$ 356.

Example 97

4-(5-Chloro-benzothiazol-2-ylamino)-2,2-dimethyl-3,4-dihydro-2H-pyrano[3,2-c]pyridin-3-ol (Compound #106)

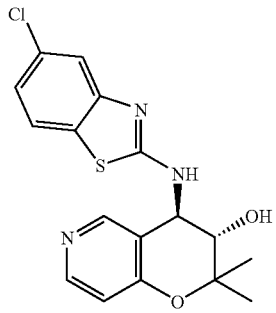

Following the procedure in Example 1, using (±)-2,2-dimethyl-1a,7b-dihydro-2H-1,3-dioxa-6-aza-cyclopropa[a]naphthalene and 5-chloro-benzothiazol-2-ylamine as starting materials, the title compound was prepared as a pale yellow solid.
$^1$H NMR: (CDCl$_3$) δ 7.50 (m, 2H), 7.00 (m, 2H), 6.85 (s, 1H), 6.75 (m, 1H), 5.05 (br, 1H), 1.60 (s, 6H)
MS (m/z): MH$^+$ 362

Example 98

4-(5-Chloro-benzoxazol-2-ylamino)-2,2-dimethyl-3,4-dihydro-2H-pyrano[3,2-c]pyridin-3-ol (Compound #107)

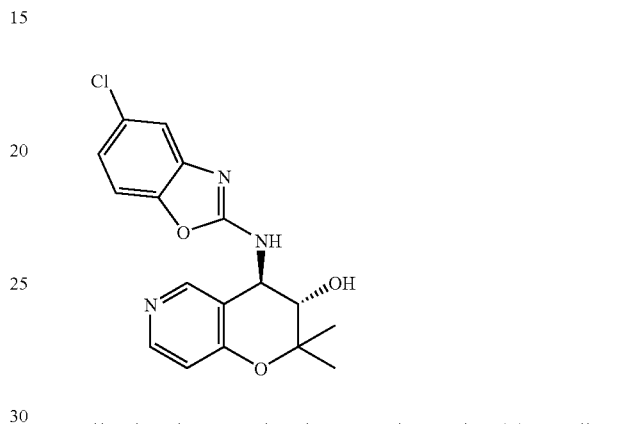

Following the procedure in Example 1, using (±)-2,2-dimethyl-1a,7b-dihydro-2H-1,3-dioxa-6-aza-cyclopropa[a]naphthalene and 5-chloro-benzooxazol-2-ylamine as starting materials, the title compound was prepared as a pale yellow solid.
$^1$H NMR: (CDCl$_3$) δ 8.40 (s, 1H), 8.15 (d, J=2.9 Hz, 1H), 7.15-7.00 (m, 3H), 6.65 (d, J=2.9 Hz, 1H), 5.00 (m, 1H), 3.80 (d, J=5.1 Hz, 1H), 3.20 (d, J=5.1 Hz, 1H), 1.50 (s, 3H), 1.35 (s, 3H)
MS (m/z): MH$^+$ 346.

Example 99

4-(2-Amino-5-chloro-benzoimidazol-1-yl)-2,2-dimethyl-2H-chromene-6-carbonitrile (Compound #45)

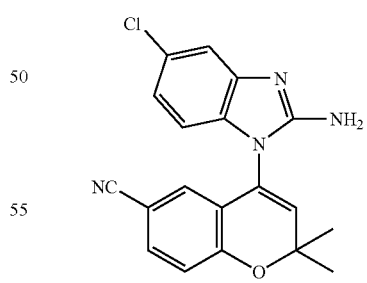

Following the procedure in Example 1, using (2,2-dimethyl-1a,7b-dihydro-2H-1,3-dioxa-cyclopropa[a]naphthalen-6-yl)-phenyl-methanone and 5-chloro-1H-benzoimidazol-2-ylamine as starting materials, the title compound was prepared as white solid.
$^1$H NMR: (CDCl$_3$) δ $^1$H NMR (CDCl$_3$) δ 7.50 (m, 1H), 7.40 (s, 1H), 7.00 (m, 2H), 6.80 (m, 1H), 6.75 (m, 1H), 6.00 (s, 1H), 5.00 (br, 2H), 1.65 (s, 6H)
MS (m/z): MH$^+$ 351.

Example 100

2,2-(tetrahydro-4-thiopyanyl)-4-oxo-6-bromo-chromane

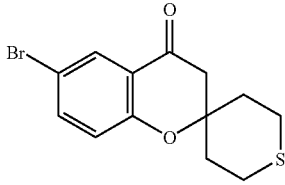

1-(5-Bromo-2-hydroxy-phenyl)-ethanone (43 mmoL) and tetrahydro-thiopyran-4-one (43 mmoL) were refluxed in a Dean-Stark flask with pyrrolidine (13 mmoL) in toluene (100 mL) overnight. After water was removed, the reaction mixture was washed with 1 N HCl, water, brine, dried over anhydrous $Na_2SO_4$, filtered and concentrated to yield the title compound as a colorless oil.

$^1$H NMR: ($CDCl_3$) δ 7.98 (s, 1H), 7.55 (d, J=7.5 Hz, 1H), 6.88 (d, J=7.5 Hz, 1H), 3.05 (t, J=8.0 Hz, 2H), 2.71 (s, 2H), 2.45 (d, J=7.8 Hz, 2H), 2.35 (d, J=7.8 Hz, 2H), 1.82 (t, J=8.0 Hz, 2H).

Example 101

6-Bromo-2,2-(tetrahydro-4-thiopyranyl)-2H-chromene

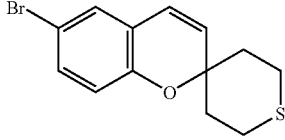

2,2-(tetrahydro-4-thiopyanyl)-4-oxo-6-bromo-chromane prepared as in Example 93 (5 mmoL) was treated with $NaBH_4$ in MeOH (10 mL) at −10° C. for 30 min. The reaction mixture was poured into ice and then the solvent was removed. The residue was extracted with DCM three times. The combined organic layer was dried over anhydrous $Na_2SO_4$, filtered and concentrated to yield a solid residue. Without further purification, the solid was refluxed in toluene (20 mL) with catalytic amount of pTSA (~50 mg) for 4 hrs. The reaction mixture was then washed with saturated $NaHCO_3$, brine, dried over anhydrous $Na_2SO_4$, filtered and concentrated to yield th crude product. The crude product was purified by silica gel chromatography with hexanes and ethyl acetate to yield the title compound as a colorless oil.

$^1$H NMR: ($CDCl_3$) δ 7.25 (d, J=7.8 Hz, 1H), 7.10 (s, 1H), 6.71 (d, J=7.8 z, 1H), 6.28 (d, J=8.5 z, 1H), 5.60 (d, J=8.5 Hz, 1H), 3.10 (t, J=8.8 Hz, 2H), 2.45 (d, J=7.5 Hz, 2H), 2.38 (d, J=7.5 Hz, 2H), 1.80 (t, J=8.8 Hz, 2H).

Example 102

6-Cyano-2,2-(tetrahydro-4-thiopyranyl)-2H-chromene

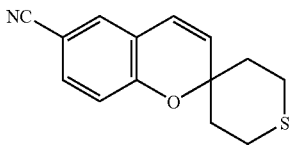

6-Bromo-2,2-(tetrahydro-4-thiopyranyl)-2H-chromene (14 mmoL) prepared as in Example 94 was treated with CuCN (28 mmoL) in DMF (50 mL) at 100° C. for 6 hrs. The cooled reaction mixture was filtered through a pad of Celite and the residue was partitioned between ethyl acetate and water. The organic layer was washed with brine, dried over anhydrous $Na_2SO_4$, filtered and concentrated to yield crude product. The crude product was purified by silica gel chromatography with hexanes and ethyl acetate to yield the title compound as a colorless oil.

$^1$H NMR: ($CDCl_3$) δ 7.40 (d, J=7.8 Hz, 1H), 6.85 (d, J=7.8 z, 1H), 6.34 (d, J=8.0 Hz, 1H), 5.65 (d, J=8.5 Hz, 1H), 3.10 (t, J=9.5 Hz, 2H), 2.45 (d, J=8.6 Hz, 2H), 2.25 (d, J=8.8 Hz, 2H), 1.85 (t, J=9.5 Hz, 2H).

Example 103

(S,S)-2,2-(tetrahydro-4-sulfonylpyranyl)-1a,7b-dihydro-2H-1,3-dioxa-cyclopropa[a]naphthalene-6-carbonitrile

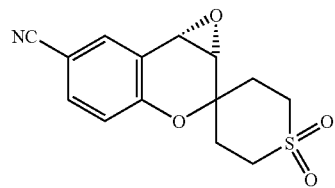

Following the procedure in Example 50, using 6-cyano-2,2-(tetrahydro-4-thiopyranyl)-2H-chromene as starting material, the title compound was prepared as a pale yellow solid.

$^1$H NMR: ($CDCl_3$) δ 7.72 (s, 1H), 7.60 (d, J=7.5 Hz, 1H), 6.98 (d, J=7.5 Hz, 1H), 3.98 (d, J=2.0 Hz, 1H), 3.62 (d, J=2.0 Hz, 1H), 3.2~2.10 (m, 8H)

MS (m/z): $MNa^+$ 314

Example 104

(3S,4R)-4-Amino-3-hydroxy-2,2-(tetrahydro-4-sulfonylpyranyl)-chroman-6-carbonitrile

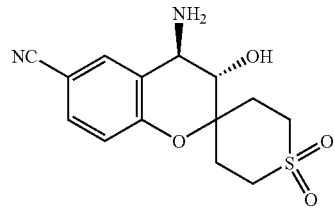

(S,S)-2,2-(tetrahydro-4-sulfonylpyranyl)-1a,7b-dihydro-2H-1,3-dioxa-cyclopropa[a]naphthalene-6-carbonitrile (10 mmoL) prepared as in Example 103 was treated with 7N $NH_3$ in MeOH (20 mL) at room temperature for 3 days. The solvent was removed and the residue was dried to yield the title compound as a pale yellow solid.

$^1$H NMR: ($CDCl_3$) δ 7.77 (s, 1H), 7.53 (d, J=7.8 Hz, 1H), 6.95 (d, J=7.8 Hz, 1H), 3.71 (d, J=9.0 Hz, 1H), 3.45 (d, J=9.0 Hz, 1H), 3.60~2.10 (m, 8H)

MS (m/z): $MH^+$ 314.

Example 105

(3S,4R)-3-Chloro-N-[6-cyano-3-hydroxy-2,2-(tetrahydro-4-sulfonylpyranyl)-chroman-4-yl]-benzamide (Compound #201)

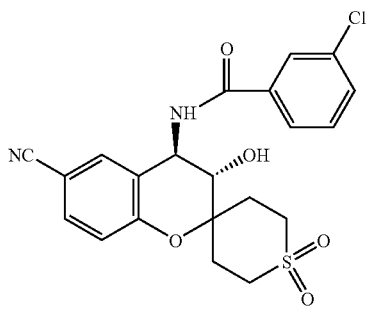

and (3S,4R)-3-Chloro-benzoic acid 4-(3-chloro-benzoylamino)-6-cyano-2,2-(tetrahydro-4-sulfonylpyranyl)-chroman-3-yl ester (Compound #202)

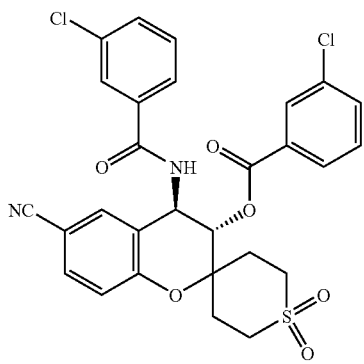

(3S,4R)-4-Amino-3-hydroxy-2,2-(tetrahydro-4-sulfonylpyranyl)-chroman-6-carbonitrile (2 mmoL) prepared as in Example 97 was treated with Et$_3$N (5 mmoL) followed by m-chlorobenzoyl chloride (4 mmoL) in DCM (10 mL) at 0° C. for 2 hrs. The reaction mixture was quenched with saturated NaHCO$_3$. The organic layer was washed with brine, dried over anhydrous Na$_2$SO$_4$, filtered and concentrated to yield crude product. The crude product was then purified by silica gel chromatography with hexanes and ethyl acetate to yield the title compounds as white solids.

Compound #201:
$^1$H NMR: (CDCl$_3$) δ 7.82 (s, 1H), 7.70 (d, J=6.5 Hz, 1H), 7.65 (s, 1H), 7.60 (t, J=6.0 Hz, 2H), 7.48 (t, J=6.0 Hz, 1H), 7.05 (d, J=7.5 Hz, 1H), 6.48 (d, J=2.5 Hz, 1H), 5.25 (t, J=8.5 Hz, 1H), 3.90 (d, J=7.8 Hz, 1H), 3.60 (m, 1H), 3.25~2.65 (m, 5H), 2.15 (m, 2H)
MS (m/z): MH$^-$ 445.

Compound #202:
$^1$H NMR: (CDCl$_3$) δ 7.98 (s, 1H), 7.90 (d, J=7.5 Hz, 1H), 7.70 (s, 1H), 7.62~7.43 (m, 6H), 7.10 (d, J=6.0 Hz, 1H), 6.53 (d, J=5.5 Hz, 1H), 5.78 (t, J=7.5 Hz, 1H), 5.55 (t, J=8.5 Hz, 1H), 3.95 (m, 1H), 3.70 (m, 1H), 3.35 (m, 1H), 3.10 (m, 1H), 2.75~2.00 (m, 5H)
MS (m/z): MH$^-$ 583.

Example 106

(3S,4R)-4-(6-Chloro-benzo[d]isoxazol-3-yloxy)-2,2-(tetrahydro-4-sulfonylpyranyl)-3-hydroxy-chroman-6-carbonitrile (Compound 200)

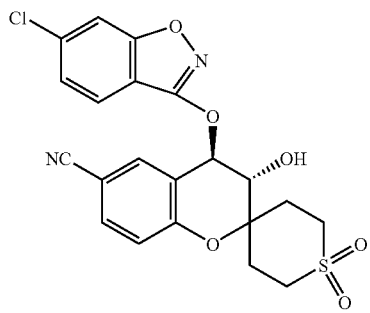

Following the procedure in Example 1, using (S,S)-2,2-(tetrahydro-4-sulfonylpyranyl)-1a,7b-dihydro-2H-1,3-dioxa-cyclopropa[a]naphthalene-6-carbonitrile prepared as in Example 103 and 6-chloro-benzo[d]isoxazol-3-one as starting materials, title compound was prepared as a pale yellow solid.

$^1$H NMR: (CDCl$_3$) δ 7.80 (s, 1H), 7.70 (t, J=8.0 Hz, 1H), 7.61 (d, J=7.8 Hz, 1H), 7.55 (s, 1H), 7.35 (d, J=7.5 Hz, 2H), 7.10 (d, J=8.0 Hz, 1H), 5.90 (d, J=7.8 Hz, 1H), 4.28 (d, J=7.8 Hz, 1H), 3.51~3.30 (m, 2H), 3.05 (m, 2H), 2.75~2.45 (m, 4H)
MS (m/z): MH$^+$ 461.

Example 107

(3S,4R)-3-Chloro-N-(6-cyano-3-hydroxy-2,2-dimethyl-chroman-4-yl)-benzenesulfonamide (Compound #66)

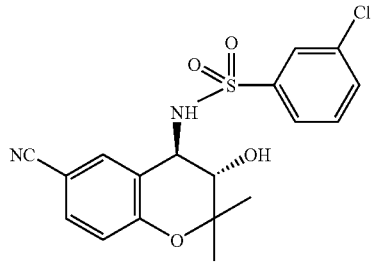

Following the procedure in Example 105, using (3S,4R)-4-amino-3-hydroxy-2,2-dimethyl-chroman-6-carbonitrile and 3-chloro-benzenesulfonyl chloride as starting materials, the title compound was prepared as a pale yellow solid.

$^1$H NMR: (CDCl$_3$) δ8.10 (s, 1H), 7.82 (d, J=7.5 Hz, 1H), 7.75 (m, 1H), 7.63 (t, J=8.5 Hz, 1H), 7.10 (d, J=8.5 Hz, 1H), 6.98 (d, J=7.5 Hz, 1H), 6.75 (m, 1H), 5.28 (t, J=7.0 Hz, 1H), 3.72 (d, J=7.0 Hz, 1H), 1.55 (s, 3H), 1.30 (s, 3H). MS (m/z): MH$^+$ 394.

Example 108

(3S,4R)-3-Chloro-N-(6-cyano-3-hydroxy-2,2-dimethyl-chroman-4-yl)-diphenylphosphinic amide (Compound #65)

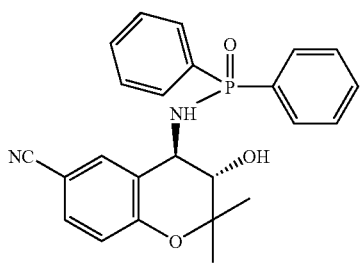

Following the procedure in Example 105, using (3S,4R)-4-amino-3-hydroxy-2,2-dimethyl-chroman-6-carbonitrile and diphenylphosphinic chloride as starting materials, the title compound was prepared as a pale yellow solid.

$^1$H NMR: (CDCl$_3$) δ 8.05 (m, 1H), 7.98 (m, 1H), 7.87 (s, 1H), 7.68~7.45 (m, 8H), 7.42 (d, J=7.8 Hz, 1H), 6.82 (d, J=8.0 Hz, 1H), 3.45 (s, 1H), 3.90 (m, 1H), 3.62 (d, J=7.8 Hz, 1H), 3.18 (m, 1H), 1.55 (s, 3H), 1.10 (s, 3H)

MS (m/z): MH$^+$ 419.

Example 109

(3S,4R)-3-Chloro-N-(6-cyano-3-hydroxy-2,2-dimethyl-chroman-4-yl)-methylphenylphosphinic amide (Compound #28)

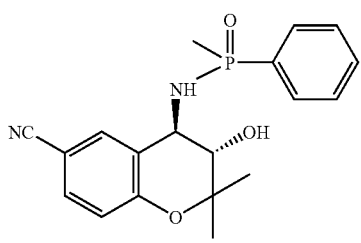

Following the procedure in Example 105, using (3S,4R)-4-amino-3-hydroxy-2,2-dimethyl-chroman-6-carbonitrile and methylphenylphosphinic chloride as starting materials, the title compound was prepared as a pale yellow solid.

$^1$H NMR: (CDCl$_3$) δ 8.15~7.52 (m, 5H), 7.10 (d, J=7.5 Hz, 1H), 6.62 9d, J=7.5 Hz, 1H), 6.08 (s, 1H), 4.23 (d, J=9.5 Hz, 1H), 3.15 (d, J=9.5 Hz, 1H), 1.55~1.42 (m, 9H).

Example 110

(3S,4R)-3-Chloro-N-(6-cyano-3-hydroxy-2,2-dimethyl-chroman-4-yl)-diphenylphosphinic ester (Compound #27)

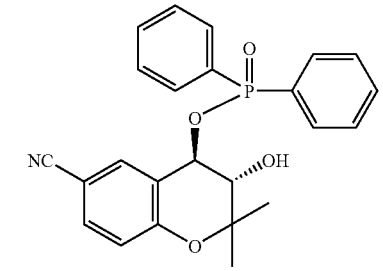

Following the procedure in Example 105, using (3S,4R)-Dihydroxy-2,2-dimethyl-chroman-6-carbonitrile and diphenylphosphinic chloride as starting materials, the title compound was prepared as a pale yellow solid.

$^1$H NMR (CDCl$_3$) δ 7.90 (m, 4H), 7.85 (m, 8H), 6.85 (m, 1H), 4.95 (m, 1H), 3.90 (m, 1H), 1.50 (s, 3H), 1.15 (s, 3H)

MS (m/z): MNa$^+$ 442

Example 111

Potassium Channel Assay

TE671 human medulloblastoma cells were obtained from ATCC and grown in Dulbecco's modified Eagle's medium (DMEM) supplemented with 10% fetal bovine serum, 100 U/ml penicillin and 100 U/ml streptomycin.

The day before testing, the cells were plated in black 96-well plates at 50 K/well. On the day of testing, the growth media was removed, then 100 μl of FLIPR buffer (20 mM HEPES, 120 mM NaCl, 2 mM KCl, 2 mM CaCl$_2$, 1 mM MgCl$_2$, 5 mM Glucose) and 100 μl of Membrane Potential Assay Dye (Molecular Devices) dissolved in FLIPR buffer were added to each well. The cells were incubated at room temperature for 15 to 30 min.

The effect of test compounds on K$_{ATP}$ channels were evaluated on a fluorometric imaging plate reader (FLIPR, Molecular Devices) at room temperature. After a baseline period, 50 μl of 5× stock solution of test compound prepared in FLIPR buffer was added and fluorescent change was monitored for 3 minutes. After this reading, glyburide, a K$_{ATP}$ channel blocker, was added to a final concentration of 5 μM to check the specificity of the test compound as a K$_{ATP}$ channel openers. Hyperpolarization resulting from K$_{ATP}$ channel opening was observed as a decrease in fluorescent intensity.

Representative compounds of the present invention were tested according to the procedure described above, with results as listed in Table 7, below.

TABLE 7

| ID No | EC$_{50}$ (μM) |
|---|---|
| 1 | 14.6 |
| 2 | 16.5 |
| 3 | 26.3 |
| 4 | 2.60 |
| 5 | 8.44 |
| 6 | 3.09 |

TABLE 7-continued

| ID No | EC$_{50}$ (μM) |
|---|---|
| 7 | 2.29 |
| 8 | 3.71 |
| 9 | >30 |
| 10 | 1.50 |
| 12 | 5.70 |
| 13 | 3.16 |
| 14 | >30 |
| 15 | 5.93 |
| 16 | >30 |
| 17 | 6.77 |
| 18 | 7.45 |
| 19 | 15.4 |
| 20 | 16.1 |
| 22 | 0.26 |
| 23 | 6.94 |
| 24 | 3.64 |
| 25 | 0.84 |
| 26 | 6.04 |
| 27 | >30 |
| 28 | 18.6 |
| 29 | 6.18 |
| 30 | 14.1 |
| 32 | 22.6 |
| 33 | 6.85 |
| 34 | 21.4 |
| 35 | 4.40 |
| 36 | 16.2 |
| 37 | 20.0 |
| 38 | 7.07 |
| 39 | 0.61 |
| 40 | 1.94 |
| 41 | 4.10 |
| 42 | >30 |
| 43 | >30 |
| 44 | 12.3 |
| 45 | >30 |
| 46 | 28.3 |
| 47 | >30 |
| 48 | 6.34 |
| 49 | >30 |
| 50 | >30 |
| 51 | >30 |
| 52 | 3.90 |
| 53 | 9.91 |
| 54 | 1.84 |
| 55 | 8.82 |
| 56 | >30 |
| 57 | 19.9 |
| 58 | 2.62 |
| 59 | 16.6 |
| 60 | >30 |
| 61 | >30 |
| 62 | 13.5 |
| 63 | 7.90 |
| 64 | 9.12 |
| 65 | >30 |
| 66 | 1.54 |
| 67 | 6.18 |
| 68 | 3.45 |
| 69 | >30 |
| 70 | 19.3 |
| 71 | >30 |
| 72 | 20.2 |
| 73 | 5.19 |
| 74 | 1.37 |
| 75 | >30 |
| 76 | 0.40 |
| 77 | >30 |
| 78 | 0.10 |
| 79 | >30 |
| 80 | >30 |
| 81 | 13.6 |

TABLE 7-continued

| ID No | EC$_{50}$ (μM) |
|---|---|
| 82 | 26.6 |
| 83 | >30 |
| 84 | 1.08 |
| 85 | >30 |
| 86 | >30 |
| 87 | >30 |
| 88 | >30 |
| 89 | >30 |
| 90 | >30 |
| 91 | 24.8 |
| 92 | 20.4 |
| 93 | 20.5 |
| 94 | 10.3 |
| 95 | 20.7 |
| 96 | 6.45 |
| 97 | >30 |
| 98 | 7.33 |
| 99 | 21.5 |
| 100 | 1.95 |
| 101 | >30 |
| 102 | 7.99 |
| 103 | 7.77 |
| 104 | 25.7 |
| 105 | >30 |
| 106 | 19.5 |
| 107 | >30 |
| 108 | 4.33 |
| 109 | 26.4 |
| 110 | >30 |
| 111 | >30 |
| 112 | 29.8 |
| 113 | 13.8 |
| 115 | 3.16 |
| 117 | >30 |
| 118 | 7.8 |
| 200 | 29.7 |
| 201 | >30 |
| 202 | >30 |
| 203 | 14.1 |

Example 112

As a specific embodiment of an oral composition, 100 mg of Compound #78 prepared as in Example 51 is formulated with sufficient finely divided lactose to provide a total amount of 580 to 590 mg to fill a size 0 hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

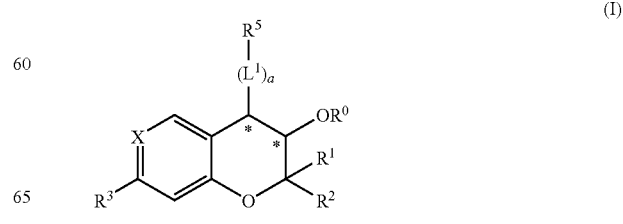

wherein
  $R^0$ is hydrogen;
  $R^1$ and $R^2$ are each methyl;
  $R^3$ is hydrogen;
  X is $CR^4$;
  $R^4$ is selected from the group consisting of cyano, phenylsulfonyl-, 1-piperidinyl-sulfonyl- and 3-fluorophenyl-sulfonyl-;
  a is 0;
  $L^1$ is selected from the group consisting of —O—, —S—, —NH— and —NH—$SO_2$—;
  $R^5$ is selected from the group consisting of 1-(5-(4-chlorophenyl)-imidazolyl), 2-(5-chloro-benzo[d]isoxazoly-3-one), and 2-(6-chloro-benzo[d]isoxazol-3-one);

provided that the -$(L^1)_a$—$R^5$ substituent group and the —$OR^0$ substituent group are in a trans orientation;

or a pharmaceutically acceptable salt thereof.

2. A pharmaceutical composition comprising a pharmaceutically acceptable carrier and a compound of claim 1.

3. A pharmaceutical composition made by mixing a compound of claim 1 and a pharmaceutically acceptable carrier.

4. A process for making a pharmaceutical composition comprising mixing a compound of claim 1 and a pharmaceutically acceptable carrier.

* * * * *